US 7,123,359 B2

(12) United States Patent
Armstrong et al.

(10) Patent No.: US 7,123,359 B2
(45) Date of Patent: *Oct. 17, 2006

(54) OPTICAL DEVICES AND METHODS EMPLOYING NANOPARTICLES, MICROCAVITIES, AND SEMICONTINUOUS METAL FILMS

(75) Inventors: Robert L. Armstrong, Las Cruces, NM (US); Vladimir M. Shalaev, West Lafayette, IN (US); Harold V. Smith, Las Cruces, NM (US); Andrey K. Sarychev, West Lafayette, IN (US); Z. Charles Ying, Boyds, MD (US)

(73) Assignee: Arrowhead Center, Inc., Las Cruces, NM (US)

( * ) Notice: Subject to any disclaimer, the term of this patent is extended or adjusted under 35 U.S.C. 154(b) by 403 days.

This patent is subject to a terminal disclaimer.

(21) Appl. No.: 10/661,319

(22) Filed: Sep. 12, 2003

(65) Prior Publication Data

US 2004/0150818 A1    Aug. 5, 2004

Related U.S. Application Data

(63) Continuation-in-part of application No. 09/797,609, filed on Mar. 1, 2001, now Pat. No. 6,781,690, which is a continuation-in-part of application No. 09/572,721, filed on May 16, 2000, now Pat. No. 6,608,716, said application No. 10/661,319 is a continuation-in-part of application No. 09/955,712, filed on Sep. 19, 2001, now abandoned.

(60) Provisional application No. 60/134,564, filed on May 17, 1999, provisional application No. 60/190,863, filed on Mar. 20, 2000, provisional application No. 60/233,804, filed on Sep. 19, 2000, provisional application No. 60/278,466, filed on Mar. 23, 2001.

(51) Int. Cl.
*G01J 3/44* (2006.01)
(52) U.S. Cl. .................................................. 356/301
(58) Field of Classification Search ................. 356/301
See application file for complete search history.

(56) References Cited

U.S. PATENT DOCUMENTS 4,781,458 A    11/1988    Angel et al.

(Continued)

FOREIGN PATENT DOCUMENTS

EP    0 527 551 A1    2/1994
WO    WO 91/20078 A1    12/1991

OTHER PUBLICATIONS

V. M. Shalaev, *Nonlinear Optics of Random Media: Fractal Composites and Metal-Dielectric Films*, Springer Tracts in Modern Physics, v.158, Springer, Berlin Heidelberg 2000.

(Continued)

*Primary Examiner*—Gregory J. Toatley, Jr.
*Assistant Examiner*—Kara Geisel
(74) *Attorney, Agent, or Firm*—Jeffrey D. Myers; Deborah A. Peacock; Philip D. Askenazy

(57) ABSTRACT

An optical sensing enhancing material (and corresponding method of making) comprising: a medium, the medium comprising a plurality of aggregated nanoparticles comprising fractals; and a microcavity, wherein the medium is located in a vicinity of the microcavity. Also an optical sensor and sensing method comprising: providing a doped medium, the medium comprising a plurality of aggregated nanoparticles comprising fractals, with the material; locating the doped medium in the vicinity of a microcavity; exciting the doped medium with a light source; and detecting light reflected from the doped medium. Also an optical sensing enhancing material comprising a medium, the medium comprising a semicontinuous metal film of randomly distributed metal particles and their clusters at approximately their percolation threshold. The medium preferably additionally comprises a microcavity/microresonator. Also devices and methods employing such material.

181 Claims, 16 Drawing Sheets

U.S. PATENT DOCUMENTS

| | | | |
|---|---|---|---|
| 4,828,758 | A | 5/1989 | Gillberg-LaForce et al. |
| 4,903,272 | A | 2/1990 | Simic-Glavaski |
| 4,913,845 | A | 4/1990 | Gillberg-LaForce et al. |
| 5,234,758 | A | 8/1993 | Olsen et al. |
| 5,249,195 | A | 9/1993 | Feldman et al. |
| 5,327,211 | A | 7/1994 | Carron et al. |
| 5,363,398 | A | 11/1994 | Glass et al. |
| 5,377,219 | A | 12/1994 | Geiger |
| 5,405,710 | A | 4/1995 | Dodabalapur et al. |
| 5,405,906 | A | 4/1995 | Olsen et al. |
| 5,469,018 | A | 11/1995 | Jacobsen et al. |
| 5,478,658 | A | 12/1995 | Dodabalapur et al. |
| 5,527,712 | A | 6/1996 | Sheeny |
| 5,616,986 | A | 4/1997 | Jacobsen et al. |
| 5,674,636 | A | 10/1997 | Dodabalapur et al. |
| 5,777,776 | A | 7/1998 | Hiraga et al. |
| 5,847,816 | A | 12/1998 | Zediker et al. |
| 5,853,464 | A | 12/1998 | Macpherson et al. |
| 5,952,665 | A | 9/1999 | Bhargava |
| 6,149,868 | A * | 11/2000 | Natan et al. .............. 356/301 |
| 6,538,794 | B1 | 3/2003 | D'Aguanno et al. |
| 6,597,492 | B1 | 7/2003 | Rosenman et al. |
| 6,791,736 | B1 | 9/2004 | Jain |
| 6,795,198 | B1 | 9/2004 | Fuchs et al. |

OTHER PUBLICATIONS

A. K. Sarychev and V. M. Shalaev, "Field Distribution, Anderson localization, and optical phenomena in random metal-dielectric films," Chapter in: *Optics of Nanostructured Materials*, Eds: V.A. Markel and T.F. George, Wiley, 2001.

V.M. Shalaev, "Surface-Enhanced Optical Phenomena in Nanostructured Fractal Materials," Chapter in: *Handbook of Nanostructured Materials and Nanotechnology*, vol. 4: Optical Properties, Edited by H. S. Nalwa, Academic Press, 2000.

V. M. Shalaev, V. P. Safonov, E.Y. Poliakov, V. A. Markel, and A. K. Sarychev, "Fractal Surface Enhanced Optical Nonlinearities", Chapter 8: *Nanostructured Materials: Clusters, Composites, and Thin Films*, Eds; V. M. Shalaev and M. Moskovits, ACS Symposium Series v. 679, ACS Books, 1997.

Local Field Distribution in Random Metal-Dielectric Films; Theory and Experiment, Dentcho A. Genov, Katyatani Seal, Mark A. Nelson, Andrey K. Sarychev, Z. Charles Ying, Vladimir M. Shalaev, Physica B 338, pp. 228-231 (2003).

Metal coverage dependence of local optical properties of semicontinuous metal films, K. Seal, M. A. Nelson, Z. C. Ying, D. A. Genov, A. K. Sarychev, and V. M. Shalaev, J. of Modern Optics 49, 2423-2435 (2002).

V. A. Podolskiy, A. K. Sarychev, V. M. Shalaev, "Temporal Dynamics of Local Optical Responses and Sub-fs Pulse Generation in Semicontinuous Metal Films," Laser Physics 12, 292 (2002).

M. Breit, V. A. Podolskiy, S. Gresillon, G. von Plessen, J. Feldmann, J. C. Rivoal, P. Gadenne, A. K. Sarychev, and Vladimir M. Shalaev, *Experimental observation of percolation-enhanced non-linear light scattering*, Phys. Rev. B 64, 125106 (2001).

V. A. Podolskiy, A. K. Sarychev, and Vladimir M. Shalaev, Percolation Composites: Localization of Surface Plasmons and Enhanced Optical Nonlinearities, in Photonic Crystals and Light Localization in the 21st Century, 567, ed. by C. M. Soukoulis (Kluwer Academic Publishers, 2001).

M. Gadenne, V. Podolskiy, P. Gadenne, P. Sheng and V. M. Shalaev, Plasmon-enhanced absorption by optical phonons in metal-dielectric composites, Europhys. Lett. 53, 364 (2001).

V. M. Shalaev and Z. C. Ying, Nonlinear Optics of Surfaces, Encyclopedia of Materials: Science and Technology, ed. by D. D. Nolte (Pergamon, Amsterdam 2000), article 6.8.13.

V. A. Shubin, A.K.Sarychev, J. P. Clerc, and V.M.Shalaev, *Local Electric And Magnetic Fields In Semicontinuous Metal Films*, Phys. Rev. B62, 11230 (2000).

A. K. Sarychev, V. A. Shubin, V. M. Shalaev, Anderson localization of surface plasmons and Kerr nonlinearity in semicontinuous metal Films, Physica B 279, 87 (2000).

A. K. Sarychev, P. C. McPhedran, and V. M. Shalaev, *Electrodynamics of metal-dielectric composites and electromagnetic crystals*, Phys. Rev. B 62, 8531 (2000).

S. Ducourtieux, S. Gresillon, A. C. Boccara, J. C. Rivoal, X. Quelin, P. Gadenne, V. P. Drachev, W. D. Bragg, V. P. Safonov, V. A. Podolskiy, Z. C. Ying, R. L. Armstrong, and Vladimir M. Shalaev, Percolation and Fractal Composites: Optical Studies, J. of Nonlinear Optical Physics and Materials 9, 105 (2000).

S. Gresillon, L. Aigouy, A. C. Boccara, J. C. Rivoal, X. Quelin, C. Desmarest, P. Gadenne, V. A. Shubin, A. K. Sarychev, and V. M. Shalaev, Experimental Observation of Localized Optical Excitations in Random Metal-Dielctric Films, Phys. Rev. Lett. 82, 4520 (1999).

W. Kim,V. P. Safonov,V. M. Shalaev,R. L. Armstrong, Fractals in Microcavities: Giant Coupled Multiplicative Enhancement of Optical Responses, Phys. Rev. Lett. 82, 4811 (1999).

A. K. Sarychev, V. A. Shubin, and Vladimir M. Shalaev, Anderson localization of surface plasmons and nonlinear optics of metal-dielectric composites, Phys. Rev. B 60, 16389 (1999).

V. A. Shubin, W. Kim, V. P. Safonov, A. K. Saruchev, R. L. Armstrong, and Vladimir M. Shalaev, Surface-Plasmon-Enhanced Radiation Effects in Confined Photonic Systems, J. of Lightwave Technology 17, 2183 (1999).

E. Poliakov, V. M. Shalaev, V. Shubin, V. A. Markel, Enhancement of nonlinear processes near rough nanometer-structured surfaces obtained by deposition of fractal colloidal aggregates on a plain substrate, Phys. Rev. B 60, 10739 (1999).

N. N. Lepeshkin, W. Kim,V. P. Safonov,J. G. Zhu,R. L. Armstrong,C. W. White,R. A. Zuhr, and V. M. Shalaev, Optical Nonlinearities of Metal-Dilectric Composites, J. of Nonlinear Optical Physics and Materials 8, 191 (1999).

Vladimir M. Shalaev and Andrey K. Sarychev, Nonlinear optics of random metal-dielectric films, Phys. Rev. B 57, 13265 (1998).

Kneipp K., et al., "Surface-Enhanced Raman Scattering: A New Tool for Biomedical Spectroscopy," *Current Science*, vol. 77, No. 7, pp. 915-924 (Oct. 10, 1999).

S. I. Bozhevolnyi, V. A. Markel, V. Coello, W. Kim, and V. M. Shalaev, Direct Observation of Localized Excitations on Rough Nanostructured Surfaces, Phys. Rev. B 58, 11441 (1998).

V. M. Shalaev, V. A. Markel,E.Y.Poliakov, R. L. Armstrong, V. P. Safonov,A. K. Sarychev, Nonlinear Optical Phenomena in Nanostructured Fractal Materials, J. Nonlinear Optic. Phys. and Materials, v. 7, 131 (1998).

V. M. Shalaev, E. Y. Poliakov, V. A. Markel, R. Botet, Nonlinear optics of fractal nanomaterials: Small-particle composites and self-affine thin Films, Physica A 241, 249 (1997).

V. M. Shalaev, E. Y. Poliakov, V.A.Markel, R. Botet,E. B. Stechel, Optical properties of self-affine surfaces, in: Fractal Frontiers, Eds: M. M. Novak and T. G. Dewey, World Scientific, Singapore, 1997; p. 421.

V. M. Shalaev,E. Y. Poliakov, V.A.Markel,V. P. Safonov,A. K. Sarychev,Surface-Enhanced Optical Nonlinearities of Nanostructured Fractal Materials, Fractals, 5 (suppl.), 63 (1997). No copy available.

F. Brouers, S. Blacher,A.N. Lagarkov,A.K.Sarychev,P. Gadenne, V.M. Shalaev, Theory of giant Raman scattering from semicontinuous fims, Phys. Rev. B 55, 13234 (1997).

Vladimir M. Shalaev, E.Y. Poliakov, V.A. Markel, and R. Botet, Nonlinear Optics of Fractal Nanocomposites and Self-Affine Thin Films, Physica A 241, 249 (1997).

Vadim A. Markel, Vladimir M. Shalaev, Evgeni Y. Poliakov, Thomas F. George, Fluctuations of light scattered by fractal clusters, J.Opt.Soc.Amer., 14, 60 (1997).

Evgeni Y. Poliakov, Vladimir M. Shalaev, Vadim A. Markel, Robert Botet, Enhanced Raman scattering from self-affine thin films, Opt.Lett., 21, 1628 (1996).

Vladimir M. Shalaev, R. Botet, J. Mercer, and E.B. Stechel, Optical properties of self-affine thin films, Phys. Rev. B 54, 8235 (1996).

Vladimir M. Shalaev, Mark I. Stockman, and R.Botet, Resonant excitations and nonlinear optics of fractals, Physica A 185, 181 (1992).

Vladimir M. Shalaev, R. Botet, and R. Jullien, Erratum: Resonant light scattering by fractal clusters, Phys. Rev. B 45, 7592 (1992).

Vladimir M. Shalaev, R. Botet, and R. Jullien, Resonant light scattering by fractal clusters, Phys. Rev. B44, 12216 (1991).

A.V. Butenko, P.A. Chubakov, Yu.E. Danilova, S.V. Karpov, A.K. Popov, S.G. Rautian, V.P. Safonov, V.V. Slabko, V.M. Shalaev, and M.I.Stockman, Nonlinear optics of metal fractal clusters, Z.Phys.D- Atoms, Molecules, and Clusters 17, 283 (1990).

P. Gadenne, B. Berini, S. Buil, X. Quelin, S. Gresillon, S. Ducourtieux, J. C. Rivoal, A. K. Sarychev, V. M. Shalaev, Localized plasmon-enhanced optical response: harmonic generation and polarization effects, Proceeding of SPIE's 46 Annual Meeting v. 4467, 288 (2001).

S. Gresillon, S. Ducourtieux, L. Aigouy, A. C. Boccara, J. C. Rivoal, P. Gadenne, X. Quelin, V. M. Shalaev, V. A. Shubin, Optical excitations of semicontinuous metal films, COLOQ6, Sep. 7-9, Bordeaux, France.

Vladimir M. Shalaev, Nonlinear Optics of Random Nanostructured Materials: Composites, Clusters, and Thin Films, XVI International Conference on Coherent and Nonlinear Optics (Moscow, Russia, Jun. 29-Jul. 3, 1998), ICONO.98 Technical Digest, URSS Publishers, p. 100 (1998).

V. M. Shalaev and A. K. Sarychev, Nonlinear Optics of Random Metal-Dielectric Films, in Nonlinear Optics.98. Materials, Fundamentals and Applications, Topical Meeting. Kauai, Hawaii, Aug. 10-14, 1998 IEEE Catalog No. 98CH36244, p. 22 (1998).

V. M. Shalaev, Fractal-surface-enhanced optical nonlinearities, Technical Digest of the Quantum Electronics and Laser Science Conference, QELS.97, Baltimore, May 18-23, 1997, 1997 OSA Technical Digest Series, v. 12, p. 88.

E. Poliakov, V. M. Shalaev, Nonlinear Optical Effects in Fractal Nanostructured Materials such as Nanocomposites and Self-Affine Surfaces, Chemistry and Physics of Small-Scale structures, Technical Digest Series, v. 2, Santa Fe, Feb. 9-11, 1997; p. 49.

R. L. Armstrong, V. P. Safonov, N. N. Lepeshkin, W. Kim, and V. M. Shalaev, Giant optical nonlinearities of fractal colloid aggregates, SPIE, San Diego, p. 107, 1997.

Vladimir M. Shalaev, Giant Optical Nonlinearities in Fractal Nanostructured Composites, Technical Digest, XX International Quantum Electronics Conference, Sydney (1996).

Vladimir M. Shalaev, J. Mercer, V.P. Safonov, and R. Botet, Nonlinear Optics of Fractal Nanocomposites and Self-Alline Surfaces, Technical Digest of Summer Topical Meeting, Nonlinear Optics: Materials, Fundamentals, and Applications, Maui, Hawaii, (1996).

V.A. Markel, E. B. Stechel, W. Kim, R. Armstrong, and Vladimir Shalaev, Optical Properties of fractal nanocomposites, Mat.Res.Soc Symp.Proc. vol. 367, 417 (1995).

Vladimir Shalaev, R. Botet, M. Moskovits, Subwavelength localization of optical modes in fractals, In: Molecular Designed Ultraþne Nanostructured Materials, Mat.Res.Soc Symp.Proc. vol. 351, 449 (1994).

A.V. Butenko, V.A. Markel, L.S. Muratov, V.M. Shalaev, and M.I. Stockman, Theory and Numerical Simulations of Optical Properties and Selective Photomodiþcation of Fractal Clusters, Proc. X International Vavilov Conference on Nonlinear Optics; in: Nonlinear Optics, edited by S.G. Rautian, Nova Science Publishers, 275 (1992).

Yu.E. Danilova, S.V. Karpov, A.K. Popov, S.G. Rautian, V.P. Safonov, V.V. Slabko, V.M. Shalaev, and M.I. Stockman, Experimental Investigation of Optical Nonlinearities of Silver Fractal Clusters, Proc. X International Vavilov Conference on Nonlinear Optics; in: Nonlinear Optics, edited by S.G. Rautian, Nova Science Publishers, 295 (1992).

A.V. Butenko, P.A. Chubakov, Yu.E. Danilova, S.V. Karpov, A.K. Popov, S.G. Rautian, V.P. Safonov, V.V. Slabko, V.M. Shalaev, M.I. Stockman, Nonlinear Optics of Metal Fractal Clusters, in: Proc. International School on Lasers and Applications, Sayanogorsk, Eastern Siberia, USSR; Published by Institute for Physics, USSR Academy of Sci., Krasnoyarsk, 78 (1991).

V.M. Shalaev, M.I. Stockman, Optical properties of fractal clusters, Proc. 3-rd Int. Conf.Trends in Quantum Electronics., Romania, 201 (1988).

Biswas, A., et al., "Time-Resolved Spectroscopy of Laser Emission from Dye-doped Droplets," *Optics Letters*, vol. 14, No. 4, pp. 214-216 (Feb. 15, 1989).

Boyd, R.W., et al., "Nonlinear Optical Properties of Nanocomposite Materials," *Pure Appl. Opt.*, vol. 5, pp. 505-512 (1996).

Chang, R.K., et al., TEXTBOOK: "Optical Processes in Microcavities," *World Scientific*, Singapore-New Jersey-London-Hong Kong (1996) Table of Contents for reference.

Chang. R.K., et al. TEXTBOOK: "Surface Enhanced Raman Scattering," *Plenum Press*, New York—London (1982) Table of Contents for reference.

Chinn, S.R., "Analysis of Counter-Pumped Small-Signal Fiber Raman Amplifiers," *Electronics Letters*, vol. 33, No. 7, pp. 607-608 (Mar. 27, 1997).

Kerker, M., et al., "Surface Enhanced Raman Scattering (SERS) of Citrate Ion Adsorbed on a Colloidal Silver," *Applied Optics*, vol. 19, No. 19, pp. 3253-3255 (Oct. 1, 1980).

Kneipp, K., et al., "Single Molecule Detection Using Surface-Enhanced Raman Scattering (SERS)", *Physical Review Letters*, vol. 78, No. 9, pp. 1667-1970, (Mar. 3, 1997).

Lee, P.C., et al., "Adsorption and Surface-Enhanced Raman of Dyes on Silver and Gold Sols," *J. Phys. Chem.*, vol. 86, pp. 3391-3395 (1982).

Lin, H.B., et al., "cw Nonlinear Optics in Droplet Microcavities Displaying Enhanced Gain," *Phys. Rev. Letters*, vol. 73, No. 18, pp. 2440-2443 (Oct. 31, 1994).

Markel, V.A., et al., "Small-Particle Composites. I. Linear Optical Properties," *Phys. Review B*, vol. 53, No. 5, pp. 2425-2436 (Feb. 1, 1996).

Markel, V.A., "Theory and Numerical Simulation of Optical Properties of Fractal Clusters," *Phys. Rev. B*, vol. 43, No. 10, pp. 8183-8195 (Apr. 1, 1991).

Moskovits, M., "Surface-Enhanced Spectroscopy," *Rev. Mod. Phys.*, vol. 57, No. 3, Part I, pp. 783-826 (Jul. 1985).

Nie, S., et al., "Probing Single Molecules and single Nanoparticles by Surface-Enhanced Raman Scattering," *Science*, vol. 275, pp. 1102-1106 (Feb. 21, 1997).

Owen, J.F., et al., "Enhancement of Fluorescense Induced by Microstructured Resonances of a Dielectric Fiber," *Phys. Rev. Letters*, vol. 47, No. 15, pp. 1975-1078 (Oct. 12, 1981).

Prasler, M.A., et al., TEXTBOOK: "Near-Field Optics: Theory, Instrumentation, and Applications," *Wiley-Interscience Publication*, John Wiley & Sons, Inc., New York (1996) Table of Contents for reference.

Rautian, S.G., et al., "Surface-Enhanced Parametric Scattering of Light by Silver clusters," *JETP Lett.*, vol. 47, No. 4, pp. 243-246 (Feb. 25, 1988).

Ritchie, G., et al., "Luminescence of Dye Molecules Adsorbed at a Ag Surface," *Phys. Rrev. B*, vol. 24, No. 8, pp. 4843-4846 (Oct. 15, 1981).

Safonov, V.P., et al., Spectral Dependence of Selective Photomodification in Fractal Aggregates of Colloidal Particles, *Phys. Rev. Lett.*, vol. 80, No. 5, pp. 1102-1105 (Feb. 2, 1998).

Shalaev, V.M., et al., "Optical Properties of Fractal Clusters (susceptibility, Surfae Enhanced Raman Scattering by Impurities," *Sov. Phys. JETP*, vol. 65, No. 2, pp. 287-294 (Feb. 1987).

Shalaev, V.M., et al., "Electromagnetic Properties of Small-Particle Composites," *Phys. Reports*, vol. 272, pp. 61-137 (1996).

Shalaev, V.M., "Nonlinear Optical Phenomena in Nanostructured Fractal Materials," *J. Nonlinear Op. Phys. & Mat.*, vol. 7, No.1, pp. 131-152 (1998).

Shalaev, V.M., et al., "Small Particle Composites. II Nonlinear Optical Properties," *Phys. Rev. B*, vol. 53, No. 5, pp. 2437-2449 (Feb. 1, 1996).

Silman, O., et al., "Surface-Enhanced Raman Scattering by Citrate on Colloidal Silver," *J. Phys. Chem.*, vol. 87, pp. 1014-1023 (1983).

Stockman. M.I., "Chaos and spatial Correlations for Dipolar Eigenproblems," *Phys. Rev. Lett.*, vol. 79, No. 23, pp. 4562-4565 (Dec. 8, 1997).

Tzeng, H.M., et al., "Laser emission from Individual Droplets at Wavelengths Corresponding to Morphology-Dependent Resonances," *Optics Lett.*, vol. 9, No. 11, pp. 499-501 (Nov. 1984).

Yariv, A., TEXTBOOK: "Quantum Electronics", Third Edition, *John Wiley & Sons*, New York, pp. 466-467 and Table of Contents for reference.

Xu, X-H, et al., "Direct Measurement of single-Molecule Diffusion and Photodecomposition in Free Solution," *Science*, vol. 275, pp. 1106-1109 (Feb. 21, 1997).

Berger, A.J., et al., "Feasibility of Measuring Blood Glucose Concentration by Near-Infrared Raman Spectroscopy," *Spectrochimca Acta Part A* vol. 53, pp. 287-292 (1997).

Carey, P.R., "Raman Spectroscopy, the Sleeping Giant in Structural Biology, Awakes," *J Biol. Chem*, vol. 274, No. 38, pp. 26625-26628 (Sep. 17, 1999).

Andrews, M.P., et al., "Integrated Optics Waveguide Spectroscopy of Self-Organizing Polymers and Fractal Composites," *Proc of SPIE*, vol. 2042, pp. 366-376 (1994).

McNichols R.J., et al., *J of Biomedical Optics*, vol. 5(#1), pp. 3-16 (Jan. 2000) (internet printout provided).

McMakin, A., "Infrared Fruit-Tester Bounces Bad Apples," *Northwest Sci & Tech*, pp. 29-3- (Winter 2001).

Pappas, D., et al., "Raman Spectroscopy in Bioanalysis," *Talanta*, vol. 51, pp. 131-144 (2000).

Pelletier, M., et al., "Keep Your Process in Control," *Photonics Spectra*, pp. 92-96 (Sep. 2000).

Storrie-Lombardi, M., et al., "Determining Glucose Levels from NIR Raman Spectra of Eyes," *NASA JPL New Technology Report NPO-204-14* p. 1 and 1a-9a (Apr. 2000).

Sulk R., et al., "Surface-Enhanced Raman Assays (SERA): Measurement of Bilirubin and Salicylate," *J. Raman Spectrosc.*, vol. 30 pp. 853-859 (1999).

Thomas, G.A., et al., "Physics in the Whirlwind of Optical Communications," *Physics Today*, pp. 30-33 (Sep. 2000).

Texas A & M U., "Raman Spectroscopy for Analyte Detection" from http://biomed.tamu.edu/obsl/rs-analyte.htm (Aug. 28, 2000).

Weber, W.H., "Raman Scattering Becomes More Accessible," *Amer Inst of Phys*.pp. 12/14 (Oct. 2000).

Burstein, E., et al., Editors, Confined Electrons and Photons, Textbook published by Plenum Press (NY and London), from Proceedings of a NATO Advanced Study Institute on Confined Electrons and Photons: New Physics and Applications, held Jul. 13-26, 1993, Erice, Italy (1995 Plenum Press New York).

Armstrong, R.L., "Nonlinear Optical Effects in Microcylinders and Microdroplets," TEXTBOOK, r.k. Chang and A.J. Campillo (eds); Opticdal Processes in Microcavities (1996) World Scientific, Singapore pp. 257-283.

Shibata, S., et al., "Preparation of Silica Microspheres Containing AG Nanoparticles," *J of Sol-Gel Sci and Tech*, Kluwer Academic Publ, Dordrecht, NL vol. 11, No. 3 pp. 279-287 (Aug. 1, 1998).

Wang, H.Z., et al., "Low-Threshold Lasing of A. Rhodamine Dye Solution Embedded with Nanoparticles Fractal Agreegates," *Optics Letters*, Optical Society of America, Washington US, vol. 23, No. 10, pp. 777-779 (May 15, 1998).

Kurokawa Y., et al., "Surface-Enhanced Raman Spectroscopic Detection of Carbonate, Sulfite, and Nucleic Acid Bases Using Polyvinyl Alcohol Film Doped with Silver Fine Particles," *Analytical Biochemistry*, vol. 209, No. 2, pp. 247-250 (1993).

Kim, W., et al., "Fractals in Microcavities: Giant Coupled, Multiplicative Enhancement of Optical Responses," *Phys. Review Letters*, Jun. 14, 1999, PAS, USA, vol. 82, No. 24, pp. 4811-4814.

Shubin, V.A., et al., "Surface-Plasmon-Enhanced Radiation Effectts in Confined Photonic Systems," *J of Lightwave Technology, IEEE*, New York US, vol. 17, No. 11 (pp 2183-2190 (Nov. 1999).

Rahm, S., "Performance of an Optical Detector Preamplifier," *Optics Letters*, vol. 18, No. 18, Sep. 15, 1993.

Purcell, E.M., "Spontaneous Emission Probabilities at Radio Frequencies," *Physical Review*, vol. 69, No. 11-12 p. 681 and whole document (Jun. 1-5, 1946).

Arnold, S., et al., "Room-Temperature Microparticle-Based Persistent Spectral Hole Burning Memory," *Optics Letters*, vol. 16, No. 6 pp. 420-422 (Mar. 16, 1991).

Emory, S.R., et al., "Near-Field Surface-Enhanced Raman Spectroscopy on Single Silver Nanoparticles," *Anal. Chem.*, vol. 69, pp. 2631-2635 (1997).

Okamoto, S., et al.,"Persistent Spectral Hole-Burning in CuCl Nanocrystals: Demonstration of Optical Data Storage," *Japanese J. Appl. Phys.*, vol. 34, pp. 128-130, Suppl 34-1 (1995).

Sharp, S.L., et al.., "spectroscopy and Imaging Using the Photon Scanning-Tunneling Microscope," *Acc. Chem. Res.*, vol. 26, p. 377-382 (1993).

Tsai, D.P., et al., "Photon Scanning Tunneling Microscopy Images of Optical Excitations of Fractal Metal Colloid Clusters," *Phys. Rev. Letters*, vol. 72, No. 26, pp. 4149-4152 (Jun. 27, 1994).

Vo-Dinh, T., et al., "Surface-Enhanced Raman Optical Data Storage: A New Optical Memory with Three-Dimensional Data Storage," *Rev. of Sci Instr.*, vol. 65, No. 12, pp. 3766-3770) Dec. 1994).

Vo-Dinh, T., "Surface-Enhanced Raman Spectroscopy Using Metallic Nanostructures," *Trends in Analytical Chemistry*, vol. 17, Nos.8+9, pp. 557-582 (1998).

Zeisel, D., et al., "Near-Field Surface-Enhanced Raman Spectroscopy of Dye Molecules Adsorbed on Silver Island Films," *Chem. Phys. Letters*, vol. 283, pp. 381-385 (Feb. 13, 1998).

* cited by examiner

OPTICAL DEVICES AND METHODS EMPLOYING NANOPARTICLES, MICROCAVITIES, AND SEMICONTINUOUS METAL FILMS

CROSS-REFERENCE TO RELATED APPLICATIONS

This application is a continuation-in-part of U.S. patent application Ser. No. 09/797,609, entitled "Sensors Employing Nanoparticles and Microcavities", filed on Mar. 1, 2001, now U.S. Pat No. 6,781,690 which is a continuation-in-part application of U.S. patent application Ser. No. 09/572,721, entitled "Optical Enhancement with Nanoparticles and Microcavities", filed on May 16, 2000 and issued as U.S. Pat. No. 6,608,716 on Aug. 19, 2003, which claims the benefit of the filing of U.S. Provisional patent application Ser. No. 60/134,564, entitled "Fractals in Microcavities: Giant Coupled, Multiplicative Enhancement of Optical Responses," filed on May 17, 1999, and of U.S. Provisional patent application Ser. No. 60/190,863, entitled "Microcavity Enhanced Optical Processes and Fractal Enhanced Optical Processes," filed on Mar. 20, 2000, and the specifications thereof are incorporated herein by reference.

This application is also a continuation-in-part of U.S. patent application Ser. No. 09/955,712, entitled "Optical Structures Employing Semicontinuous Metal Films", filed on Sep. 19, 2001 now abandoned, which claims the benefit of the filing of U.S. Provisional Patent Application Ser. No. 60/233,804, entitled "Optical Recording and Limiting, Enhanced Photochemistry, Photobiology, Super-Sensitive Spectroscopy, Microlasers, Optical Switches and Amplifiers Using Semicontinuous Metal Films and Microresonators," filed on Sep. 19, 2000, and of U.S. Provisional Patent Application Ser. No. 60/278,466, entitled "Identification of Enantiomers Using Semicontinuous Metal Films," filed on Mar. 23, 2001, and the specifications thereof are incorporated herein by reference.

GOVERNMENT RIGHTS

The U.S. Government has a paid-up license in this invention and the right in limited circumstances to require the patent owner to license others on reasonable terms as provided for by the terms of National Science Foundation Contract Nos. DMR-9623663 and DMR-9810183, Contract No. NAG8-1710 awarded by the U.S. National Aeronautics and Space Administration (NASA), by ARO under grant DAAG55-98-1-0425 awarded by the U.S. Army, and under New Mexico Universities Collaborative Research (NUCOR) Program grant numbers 9882 and 9964.

BACKGROUND OF THE INVENTION

1. Field of the Invention (Technical Field)

The present invention relates to enhancing linear and nonlinear optical emission using nanoparticles, wherein the nanoparticles are either non-aggregated or aggregated, and microcavities. The aggregrated nanoparticles comprise fractals. Microcavities are used in combination with nanoparticles for greatly enhanced optical emission.

The present invention also relates to optical methods and structures employing semicontinuous metal films and microresonator/semicontinuous-metal-film composites.

2. Background Art

Recently, fractal aggregates of gold, silver, and other noble metals have received attention in the field of linear and nonlinear optical research. Fractals comprise aggregates of particles in colloidal solutions, sols and gels, and soot and smoke. Also, most macromolecules exist in the form of fractals. A fractal aggregate is a system of interacting particles, with special scale-invariant geometry. Scale-invariance in particle aggregates manifests itself in spacial scales larger than the sizes of particles forming the cluster and smaller than the size of the whole cluster; therefore, to track the fractal geometry in a single aggregate it must be relatively large. However, an ensemble of small aggregates of particles, with the number of particles on the order of only ten or more, can also manifest the fractal geometry statistically, on average, despite the fact that single clusters do not manifest the fractal geometry when considered individually. Thus, the term fractals comprises an ensemble of large aggregates (the ensemble can be small and consist of few, or even one, cluster), or a large ensemble of small aggregates of particles, which statistically show the fractal (scale-invariant) geometry with some interval of sizes.

Enhanced optical response in metal nanocomposites characterized by fractal geometry and thin metallic films containing nanoscale surface features has been intensively studied. R. K. Chang and T. E. Furtak, Ed., *Surface Enhanced Raman Scattering* (Plenum Pres, NY, 1982); M. Moskovits, Rev. Mod. Phys. 57, 783 (1985); R. W. Boyd, et al., Pure Appl. Opt. 5, 505 (1996); V. M. Shalaev and M. I. Stockman, Sov. Phys. JETP 65, 287 (1987); V. A. Markel, et al., Phys. Rev. B 43, 8183 (1991); V. M. Shalaev, Phys. Reports 272, 61 (1996); V. A. Markel, et al., Phys. Rev. B 53, 2425 (1996); V. M. Shalaev, et al., Phys. Rev. B 53, 2437 (1996); M. I. Stockman, Phys. Rev. Lett. 79, 4562 (1997); S. G. Rautian, et al., JETP Lett. 47, 243 (1988); V. P. Safonov et al., Phys. Rev. Lett 80, 1102 (1998); V. M. Shalaev et al., J. Nonlinear Optical Physics and Materials 7, 131 (1998). Enhancement in the optical response is associated with the excitation of surface plasmons, collective electromagnetic modes whose characteristics are strongly dependent on the geometrical structure of the metallic component of the medium. Collective optical excitations, such as surface plasmons, are often spatially localized in fractals. This localization leads to the presence of nanometer-scale spatial regions of high local electric fields, "hot spots", and accordingly, to significant enhancement for a variety of optical processes, such as Raman scattering, four-wave mixing, and nonlinear absorption and refraction. In some cases, the local enhancement at a hot spot can be $10^9$ greater than the average enhancement resulting from the fractal itself, averaged over the entire surface of the fractal.

Fractals also have another important property—they are subject to surface enhanced Raman scattering (SERS) by adsorbed molecules. Suitable substrates known to exhibit SERS include colloidal metal particles, vacuum deposited films, single crystals, and matrix isolated metal clusters. O. Silman, et al., J. Phys. Chem. 87, 1014–23 (1983). Also, adsorption of dye molecules, e.g., Rhodamine 6G (R6G), on colloidal Ag or Au is known. P. C. Lee and D. Melsel, J. Phys. Chem. 86, 3391–95 (1982). Once adsorbed onto the colloidal particle, the adsorbed molecules may exhibit strong surface enhanced Raman scattering.

Fractal aggregates of metal nano-sized particles can provide dramatic enhancement for various linear and nonlinear optical responses, including Raman Scattering (RS) and Hyper-Raman Scattering (HRS). This occurs because of localization of optical plasmon excitations within small parts of a fractal aggregate, hot spots, smaller than the size of the fractal and often smaller than the wavelength. When sufficiently concentrated, the large electromagnetic fields in the hot spots can result in very large enhancement of optical responses. The small areas, where the fractal optical excitations are localized, have very different local structures and, therefore, they are characterized by different resonant frequencies. Because of the large variety in local geometries of fractal hot spots, the normal modes of a fractal aggregate cover a huge spectral range, from the near ultra-violet to the far-infrared, leading to giant enhancement of optical responses within this large spectral range. Furthermore, since the dielectric constant of metal is negative and increases in magnitude toward the longer wavelengths, the enhancement for optical processes becomes progressively larger toward infrared (IR) wavelengths.

The various nano-scale areas, where the resonant fractal excitations are localized, can be thought of as a set of different optical "nano-resonators", each having different resonance frequencies resonating in the visible and IR spectral ranges. These fractal nano-resonators have large resonance quality-factors (Q), representing the local-field enhancement, that increase from the visible to the IR region of the spectrum.

Large enhancement for SERS can also be obtained in compact structures, such as nano-sized spheroids or small chain-like aggregates of particles. However, a compact structure of a given geometry has very few normal modes, for example, one, in a sphere, and three, in a spheroid, and thus provide enhancement at only a few selected frequencies. In contrast, in random fractals, there are always such configurations of particles (nano-resonators) that resonate at any given wavelength. Thus, the inherent properties of random fractals provide localization of optical excitations which become sensitive to the local structures. In addition, the fractals exist as a large variety of resonating local structures, which leads to a very broad enhancement band from the near ultra-violet to the far-infrared region of the spectrum.

An alternative approach for achieving large enhancement of the optical response involves the excitation of morphology-dependent resonances (MDRs) in dielectric microcavities. R. K. Chang and A. J. Campillo, Ed., *Optical Processes in Microcavities*, World Scientific, Singapore-NewJersey-London-Hong Kong (1996). These resonances, which may have very high quality factors, Q on the order of $10^5$ to $10^9$, result from confinement of the radiation within the microcavity by total internal reflection. Light emitted or scattered in the microcavity may couple to the high-Q MDRs lying within its spectral bandwidth, leading to enhancement of both spontaneous and stimulated optical emissions. For example, enhanced fluorescence emission from a dye-doped cylindrical or spherical microcavity occurs when either the laser pump or the fluorescence, or both, couple to microcavity MDRs. J. F. Owen, Phys. Rev. Lett. 47, 1075 (1981). Moreover, the increased feedback produced by MDRs is sufficient to obtain laser emission from a dye-doped microdroplet under both a continuous wave (CW) and pulsed laser excitation. H. M. Tzeng, et al., Opt. Lett. 9, 499 (1984); A. Biswas, et al., Opt. Lett. 14, 214 (1988). The existence of high-Q microcavity modes is also responsible for numerous stimulated nonlinear effects including stimulated Raman and Rayleigh-wing scattering and four-wave parametric oscillation under moderate intensity CW excitation. M. B. Lin and A. J. Campillo, Phys. Rev. Lett. 73, 2440 (1994).

Optical microcavities are resonators that have at least one dimension, on the order of a single or at most a small integral number of optical wavelengths. See Dodabalapur, et al., U.S. Pat. No. 5,405,710, entitled "Article Comprising Microcavity Light Sources." The specific geometry of the microcavity and the boundary conditions on the interface of the dielectric-to-air impose selective normal modes on the optical microcavity. Typical microcavities have diameters of 100 microns or less. Such microcavities have shown technological promise for constructing novel light emitting devices. Possible applications of microcavities devices include flat panel displays, optical interconnects, optical fiber communications, and light emitting diode (LED) printing. For example, in a display application, a device may consist of three microcavities, each microcavity emitting in the blue, green, and red regions of the visible spectrum. Further, resonant microcavities have the advantage of emitting light in a highly directional manner as a result of their inherent geometry.

As described briefly above fractal aggregates and resonating microcavities are known to cause large enhancements of optical emissions. The present invention uses the properties of nanoparticles, fractals, and microcavities to enhance optical emissions for a variety of apparatuses and methods. The present invention further combines the properties of these optical enhancement processes by placing nanoparticles and/or fractal aggregates within a high-Q microcavity. Overall, the observed optical enhancement of the invention is multiplicative rather than additive of the two processes. Results demonstrate the unique potential of such devices in the development of ultra-low threshold microlasers, nonlinear-optical devices for photonics, as well as new opportunities of micro-analysis, including spectroscopy of single molecules, quantum wells and nanocrystals.

For purposes of the specification and claims, a semicontinuous metal film, also called a random metal-dielectric film, is a thin film comprising randomly distributed metal particles and their clusters at or near the percolation (conductivity) threshold. The percolation threshold is defined as the metal filling factor $p_c$ at which the metal-dielectric film experiences a transition from an insulator to a conductor, with respect to the DC electric current. Semicontinuous metal films can be grown on top of a dielectric or semiconductor substrate. A metal film reaches its percolation threshold where there exists a continuous conducting path between two opposite ends of the film. A metal film developed at or near its percolation threshold is semicontinuous, in contrast to discontinuous films at much lower metal-filling factors and continuous films at much higher metal-filling factors.

Surface-plasmon excitations in a semicontinuous metal film are localized in small nanometer-scale volumes, called hot spots. V. M. Shalaev, *Nonlinear Optics Of Random Media: Fractal Composites and Metal-Dielectric Films* (Springer Verlag, Berlin, December 1999); A. K. Sarychev and V. M. Shalaev, Physics Reports 335, p. 275 (September 2000); S. Grésillon, et al., Phys. Rev. Lett. 82, p.4520 (May 1999); A. K. Sarychev, et al., Phys. Rev. B 60, p. 16389 (December 1999); V. M. Shalaev, et al., Phys. Rev. B 57, p. 13265 (May 1998); A. K. Sarychev, et al., Phys. Rev. E 59, p. 7239 (June 1999). The electromagnetic energy is concentrated in the hot spots, leading to the local optical intensity that can exceed the intensity of the incident light beam by four to five orders of magnitude, i.e., by a factor up to 100,000. The very intense local fields in the hot spots, with dimensions of approximately 10 nm, result in dramatically enhanced linear and, especially, nonlinear optical responses. While a linear optical response is proportional to light intensity, a nonlinear optical response is scaled with the square, cube or even higher power of light intensity and, therefore experiences a larger enhancement.

A semicontinuous metal film provides enhanced linear and nonlinear optical responses as long as its metal-filling factor p satisfies the condition of $|p-p_c| \leq (\epsilon_{dielectric}/|\epsilon_{metal}|)^{1/(t+s)}$, where $p_c$ is the metal-filling factor at the percolation threshold, $\epsilon_{dielectric}$ is the dielectric function (i.e., permittivity) of the dielectric component of the semicontinuous metal film, and $\epsilon_{metal}$ is the dielectric function of the metal component of the film. For a three-dimensionally semicontinuous metal film, t=2.05 and s=0.76 so that the exponent 1/(t+s)=0.356. For a very thin semicontinuous metal film, which can be viewed approximately as two dimensional, t=s=4/3 so that the exponent 1/(t+s)=0.375, which is quite close to the three-dimensional value of 0.356. For the purpose of defining the applicable range of a semicontinuous metal film for enhancing optical responses, the metal-filling factor p of the film should be within a range between $p_c-(\epsilon_{dielectric}/|\epsilon_{metal}|)^{0.36}$ and $p_c+(\epsilon_{dielectric}/|\epsilon_{metal}|)^{0.36}$.

The following patents are illustrative of the prior art, albeit not disclosing use of semicontinuous metal films: U.S. Pat. No. 6,017,630 discloses forming ultrafine particles on a substrate by directing a slanting high energy irradiating beam against side walls of a plurality of pores in a target material. U.S. Pat. Nos. 5,817,410, 4,448,485, 5,401,569, 5,472,777, and 5,113,473 relate to isolated (i.e., independent) particles. U.S. Pat. Nos. 4,583,818, 6,122,091, 5,991,488, 5,067,788, 6,034,809, and 5,858,799 relate to continuous films. Additionally, periodic arrangements, different from random distribution of metal clusters in semicontinuous metal films, are disclosed in U.S. Pat. Nos. 4,583,818, 4,448,485, and 5,113,473.

SUMMARY OF THE INVENTION
(DISCLOSURE OF THE INVENTION)

The present invention is a light emitting apparatus that is comprised of at least one light source, such as a laser, and a medium that is made up of nanoparticles. These nanoparticles can either be non-aggregated nanoparticles and/or aggregated nanoparticles, wherein the aggregated nanoparticles comprise fractals. Preferably, each fractal comprises at least ten aggregated nanoparticles, and furthermore each fractal comprises a dimension less than that of the embedding space. The apparatus can further comprise a microcavity. The medium is then located in the vicinity of the microcavity in order to enhance the optical emission. To be in the vicinity of the microcavity, the medium is located within a light wavelength of the surface of the microcavity or within the boundaries of the microcavity. The microcavity can be either solid or hollow. When the microcavity is solid, the medium can either be located on a surface of the microcavity or embedded within the microcavity. When the microcavity is hollow, the medium can either be located within the hollow microcavity or on a surface of the hollow microcavity. The microcavity can be either cylindrical, spherical, spheroidal, polyhedral, or an optical wave guide microcavity. The exterior dimension of the microcavity is preferably at least twice that of the optical wavelength of interest.

The medium can further be contained within a liquid suspension, gel matrix, or solid matrix. The medium itself can be of metal, semi-metal, and/or a semiconductor. Metals that can be used for the medium can be either silver, gold, platinum, copper, aluminum, or magnesium. The semi-metal can be graphite. Any of Group IV, Group III-V, or Group II-VI semiconductors can be used.

Preferably the average diameter of each individual nanoparticle is less than that of the optical wavelength of interest. The light source, such as a pump laser, for the present invention preferably emits light of wavelengths between approximately 200 and 100,000 nanometers, more preferably between approximately 300 and 2,000 nanometers. The light source also emits light, having between approximately 1 nanowatt and 100 watts of power.

Optionally, at least one optically active organic and/or inorganic molecule is adsorbed on a surface of the nanoparticles. For example, laser dye or sodium citrate molecules can be adsorbed on a surface of the nanoparticles. The laser dye can be a xanthene, coumarin, pyrromethene, styryl, cyanine, carbon-bridged, naphthofluorescein-type, acridone, quinalone derivative, p-terphenyl, p-quaterphenyl, or a 9-aminoacridine hydrochloride dye. In the alternative, at least one optically active organic and/or inorganic molecule is located within the light wavelength of the surface of the nanoparticles. Again, such a molecule can be either a laser dye or sodium citrate molecules.

The present invention is also a method of enhancing the optical emission of a material and comprises the steps of doping a medium, wherein the medium comprises a plurality of nanoparticles, either non-aggregated nanoparticles and/or aggregated nanoparticles, and exciting the doped medium with at least one light source. The aggregated nanoparticles are fractals. The medium can be doped with at least one material from the materials including a single molecule, a plurality of molecules, a nanocrystal, a solid matrix, DNA, DNA fragments, amino acids, antigen, antibodies, bacteria, bacterial spores, and viruses. The method can further include the step of locating the doped medium in the vicinity of a microcavity. Locating can comprise locating the medium on a surface of a solid microcavity or embedding the medium within a solid microcavity. Alternatively, the locating step can comprise locating the medium within a hollow microcavity, or alternatively locating the medium on a surface of a hollow microcavity.

When exciting the medium, the exciting step can comprise exciting the doped medium to result in at least one type of optical process, such as photoluminescence, Raman scattering, hyper-Raman scattering, Brouillon scattering, harmonic generation, sum frequency generation, difference frequency generation, optical parametric processes, multiphoton absorption, optical Kerr effect, four-wave mixing, and phase conjugation. Optionally, the method further comprises containing the medium within a substance such as a liquid suspension, a gel matrix, or a solid matrix. The doped medium can comprise metal, semi-metal, and/or a semiconductor. Examples of metals include silver, gold, platinum, copper, aluminum, and magnesium. The semi-metal can comprise graphite, and the semiconductor can be any of either Group IV, Group III-V, or Group II-VI semiconductors.

The exciting step preferably comprises emitting light of wavelengths between approximately 200 and 100,000 nanometers, more preferably between 300 and 2,000 nanometers, and wherein the light emitted has between anywhere from approximately 1 nanowatt to 100 watts of power.

The doping step can further comprise doping with at least one optically active organic and/or inorganic molecule located within the light wavelengths of the surface of the medium. These molecules can be, for example, laser dye or sodium citrate molecules.

Furthermore, the present invention provides a wavelength translation apparatus, wherein the apparatus comprises at least one light source and a medium made up of a plurality of nanoparticles, wherein the nanoparticles are either non-aggregated nanoparticles and/or fractals comprised of aggregated nanoparticles. The wavelength translation apparatus can further include a microcavity and a medium, wherein the medium is located in the vicinity of the microcavity to enhance optical emission. The methodology for wavelength translation comprises the steps of providing the medium having a plurality of nanoparticles, be it either non-aggregated and/or aggregated nanoparticles, and exciting the medium with a light source, such as a laser. The method can further include the step of locating the medium in the vicinity of a microcavity to amplify optical emission. Locating the medium in the vicinity of a microcavity to amplify optical emission further comprises amplifying the optical emission via at least one of the following processes: stimulated emission of photons, stimulated Raman scattering, stimulated hyper-Raman scattering, stimulated Brouillon scattering, optical parametric amplification, multi-photon emission, four-wave mixing, and phase conjugation.

The present invention further provides an amplifying apparatus having a gain greater than 1.2 and consists of at least one light source, a microcavity, and a medium made up of a plurality of nanoparticles, being either non-aggregated and/or aggregated nanoparticles, and wherein the medium is located in the vicinity of the microcavity to enhance optical emission. The method of amplification comprises providing the medium and locating it within the vicinity of a microcavity to amplify the optical emission, as well as exciting the medium with at least one light source, such as a laser.

The present invention further provides for an optical parametric oscillator comprising at least one light source, a cavity, and a medium wherein the medium comprises a plurality of nanoparticles. The nanoparticles can be non-aggregated nanoparticles and/or aggregated nanoparticles. The aggregated nanoparticles comprise fractals. The medium is located in the vicinity of the cavity to enhance optical emission. Preferably the cavity comprises a microcavity.

The present invention further provides for a light detection and ranging system comprising a transmitter light source; a receiver to receive light produced from the interaction of the transmitter light with constituents; and a medium. The medium comprises a plurality of nanoparticles and the nanoparticles can be non-aggregated and/or aggregated nanoparticles. The light detection and ranging system further comprises a microcavity to receive light from the receiver, wherein the medium is located in the vicinity of the microcavity to amplify the received light.

The present invention still further provides a method of optical data storage and comprises the steps of providing a medium, wherein the medium comprises a plurality of nanoparticles. The nanoparticles can be non-aggregated nanoparticles and/or aggregated nanoparticles. The method further includes the steps of irradiating the medium with polychromatic light and generating hot spots in the medium due to intensity differences of different wavelengths, and spectral hole burning the medium due to photomodification, thereby creating high density storage capabilities. The method for optical data storage can further comprise the step of locating the medium in the vicinity of a microcavity to amplify optical emission.

The present invention still further provides for near-field optical spectroscopy. This method provides for spatial resolution on the order of 1 nanometer. One method for detecting materials with near-field optics comprises locating the material within a distance shorter than the light wavelength from a tapered end of an optical fiber and detecting the light emitted from the material through the optical fiber. A second method for detecting a material with near-field optics comprises locating a tapered end of an optical fiber within a distance shorter than the light wavelength from the material in order to illuminate the material. A third method of detecting a material using near-field optics comprises locating a sharp tip of a vibrating metal wire within a distance shorter than the light wavelength from the material, and detecting the light emitted from the material with a lock-in method. In all of these methodologies, the material to be detected is located within a distance shorter than the light wavelength from either a tapered end of an optical fiber or a sharp tip of a vibrating metal wire.

Near-field optical spectroscopy is a near-field optical spectroscopic method for detecting chemical compounds and biological materials through their spectroscopic signatures. The present invention is further of near-field optical spectroscopy by increasing the ability to detect any of the following materials: a single molecule, a plurality of molecules, a nanocrystal, DNA, DNA fragments, amino acids, antigen, antibodies, bacteria, bacterial spores, or viruses. The method further comprises obtaining spectroscopic signatures such as electronic, vibrational or rotational spectroscopic signatures. The method can further include an optical process such as photoluminescence, Raman scattering, hyper-Raman scattering, Brouillon scattering, harmonic generation, sum frequency generation, difference frequency generation, and optical Kerr effect.

Near-field optical signals can be enhanced by the nanoparticles of the present invention, be they non-aggregated nanoparticles and/or aggregated nanoparticles. By doping the material to be detected onto a medium that comprises the nanoparticles, near-field optical signals are enhanced. In the method where the light signal is detected through an optical fiber, the medium can be instead deposited onto the input end of the optical fiber. Furthermore, the microcavity of the present invention can enhance near-field optical spectroscopy of a material when that material is located in the vicinity of the microcavity. By combining the doped medium with the microcavity and locating the medium in the vicinity of the microcavity, near-field optical spectroscopy can also be enhanced. In the case where the light signal is detected through the optical fiber, the medium could be instead deposited onto the input end of the optical fiber.

The invention is additionally of an optical sensing enhancing material (and corresponding method of making) comprising: a medium, the medium comprising a plurality of aggregated nanoparticles comprising fractals; and a microcavity, wherein the medium is located in a vicinity of the microcavity. In the preferred embodiment, the invention additionally comprises an analyte deposited with the medium in the vicinity of the microcavity by laser ablation, particle deposition, or lithography, and a non-reactive surface coating is placed over the analyte and the medium.

The invention is further of an optical sensor and sensing method comprising: providing a doped medium, the medium comprising a plurality of aggregated nanoparticles comprising fractals, with the material; locating the doped medium in the vicinity of (for purposes of the specification and claims, this includes inside) a microcavity; exciting the doped medium with a light source; and detecting light reflected from the doped medium. In the preferred embodiment, Raman or photoluminescence (both linear and nonlinear) signals are detected. Analytes may be placed in direct contact with the doped medium or located remotely from the medium. The lights source can comprise two counterpropogating light sources. The microcavity is preferably a silica microsphere or deformed silica microsphere, a quartz tube or quartz rod.

The invention is yet further of a method of detecting a material comprising: exciting both the material and a medium in a vicinity of a microcavity, the medium comprising a plurality of aggregated nanoparticles comprising fractals, with at least one light source; and detecting spectroscopic data of the material. In the preferred embodiment, Raman or photoluminescence (both linear and nonlinear) signals are detected and the material is any one or more of the following items: chemical and biological warfare agents, chemical and biological contaminants of the environment, explosive agents, controlled substances, chemical and biological agents in manufacturing process streams, and chemical and biological agents in a substrate selected from the group consisting of blood, blood byproducts, urine, saliva, cerebral spinal fluid, tears, semen, uterine secretions, fecal matter, respiratory gases, lung secretions, skin, and aqueous humor of the eye.

The invention is also of a method of detecting contaminants of the environment resulting from natural disasters (e.g., fires) and various anthropogenic activities. These pollutants include fly ash and smoke lofted into the atmosphere by fires, soot aggregates formed during the process of incomplete combustion of hydrocarbon fuels, sulfate and carbonaceous soot aggregates (both of which have an important anthropogenic component and are the dominant tropospheric aerosol components), metal colloid aggregates released into the atmosphere during metallurgical processes, and also produced by metal evaporation, accompanying, for example, explosions and fires. A number of biological and chemical pollutants, such as acid rains, chemical smog, sulfate aerosols, toxic and carcinogenic urban aerosols can also be detected using the invention. Many of toxic chemical and biological materials and soot aggregates are organized into fractal structures and can be scavenged in the atmosphere by liquid microdroplets, which form very efficient microcavities. This can result in optical enhancement and make easier the optical detection of the environmental pollutants. All the pollutants mentioned above are major factors in a variety of environmental problems, including global warming due to increases in greenhouse gases, an atmosphere cooling effect (resulting from an increase in scattering, which may partially offset the effect of global warming), acid rain, photochemical smog, visibility concerns, and cloud characteristics (e.g., soot aggregates are responsible for the significant increase in cloud cover observed in the northern hemisphere during the last century). The aerosols are also responsible for observed changes in cloud droplet number concentrations with important consequences for visibility and pollution control. The toxic and carcinogenic characteristics of urban aerosols constitute an important public health concern and can be efficiently detected using optical detection provide by the current invention.

The present invention is of an optical enhancing material comprising a medium, the medium comprising a semicontinuous metal film of randomly distributed metal particles and their clusters at approximately their percolation threshold. In the preferred embodiment, the metal comprises at least one metal selected from silver, gold, copper, platinum, nickel, and aluminum. The metal particles have an average width between approximately 1 and 1000 nanometers. The metal particles and their clusters have lengths varying from the widths of individual metal particles to a lateral size of the metal film. The semicontinuous metal film has an average thickness between approximately 1 and 100 nanometers. The semicontinuous metal film has a metal-filling factor p over a range between $p_c-(\epsilon_{dielectric}/|\epsilon_{metal}|)^{0.36}$ and $p_c+(\epsilon_{dielectric}/|\epsilon_{metal}|)^{0.36}$, where $p_c$ is a metal-filling factor at the percolation threshold, $\epsilon_{dielectric}$ is a dielectric function, permittivity, of a dielectric component of the semicontinuous metal film, and $\epsilon_{metal}$ is a dielectric function, permittivity, of a metal component of the semicontinuous metal film. The semicontinuous metal film is manufactured via at least one technique from ion exchange, thermal evaporation, pulsed laser deposition, laser ablation, electron-beam deposition, ion-beam deposition, sputtering, radio-frequency glow discharge, and lithography. The material provides optical enhancement at light wavelengths between approximately 10 and 100,000 nanometers, most preferably between approximately 200 and 20,000 nanometers. An analyte may be placed proximate the medium, such as at least one of the following: atoms, molecules, nanocrystals, nanoparticles, and biological materials. The analyte can be chiral. A non-reactive surface coating may be placed over the analyte, the medium, or both. The material may additionally comprise a microcavity/microresonator made of one or more materials selected from dielectric and semiconductor materials. The microcavity may be a sphere, a deformed sphere, a spheroid, a rod, or a tube. The microcavity may be a semiconductor laser cavity. The medium may be located at one or more surfaces of the microcavity (inner and/or outer surfaces). The medium may be an integrated component of the microcavity.

The invention is also of an optical sensor comprising: a medium, the medium comprising a semicontinuous metal film of randomly distributed metal particles and their clusters at approximately their percolation threshold; a light source incident on the medium; and one or more detectors of light emitted from the medium. In the preferred embodiment, the detector detects at least one signal selected from fluorescence, spontaneous emission, Raman scattering, Rayleigh scattering, Brillouin scattering, and/or nonlinear optical processes selected from the group consisting of stimulated Raman scattering, hyper-Raman scattering, hyper-Rayleigh scattering, multi-photon anti-Stokes emission, harmonic generation, sum-frequency generation, difference-frequency generation, optical parametric processes, multi-photon absorption, three- and four-wave mixing, and phase conjugation. The optical sensor may additionally comprise a microcavity/microresonator.

The invention is additionally of an optical sensing method comprising the steps of: providing a doped medium, the medium comprising a semicontinuous metal film of randomly distributed metal particles and their clusters at approximately their percolation threshold; locating the doped medium proximate a medium; exciting the doped medium with a light source; and detecting light emitted from the doped medium. In the preferred embodiment, detecting comprises detecting at least one signal selected from: fluorescence, spontaneous emission, Raman scattering, Rayleigh scattering, Brillouin scattering, and/or nonlinear optical processes selected from the group consisting of stimulated Raman scattering, multi-photon anti-Stokes emission, hyper-Raman scattering, hyper-Rayleigh scattering, harmonic generation, sum-frequency generation, difference-frequency generation, optical parametric processes, multi-photon absorption, three- and four-wave mixing, and phase conjugation. A microcavity/microresonator may be employed in an additional step.

The invention is further of a method of detecting an analyte material, comprising: exciting both the analyte material and a medium in a vicinity of the analyte material, the medium comprising a semicontinuous metal film of randomly distributed metal particles and their clusters at approximately their percolation threshold, with at least one light source; and detecting light emitted from the material and medium. In the preferred embodiment, detecting comprises detecting at least one signal selected from: fluorescence, spontaneous emission, Raman scattering, Rayleigh scattering, Brillouin scattering, and/or nonlinear optical processes selected from the group consisting of stimulated Raman scattering, multi-photon anti-Stokes emission, hyper-Raman scattering, hyper-Rayleigh scattering, harmonic generation, sum-frequency generation, difference-frequency generation, optical parametric processes, multi-photon absorption, three- and four-wave mixing, and phase conjugation. A microcavity/microresonator may be employed in an additional step. The analyte material is preferably selected from: atoms; molecules (including but not limited to chiral molecules); nanoparticles; chemical agents in water and atmosphere; biological agents in water and atmosphere; contaminations and environment hazards in the air, in water, in soil, at or near manufacturing sites, or at waste dumps; explosives; controlled substances; residual chemicals in foods; food poison; and chemical and biological agents in a body, bodily fluids, and wastes of humans and animals.

The invention is yet further of a gratingless spectrometer comprising: a medium, the medium comprising a semicontinuous metal film of randomly distributed metal particles and their clusters at approximately their percolation threshold; a light source incident on the medium; and one or more near-field detectors of light emitted from the medium. The medium can also include a microcavity/microresonator along with semicontinuous metal film.

The invention is still further of a gratingless spectroscopy method comprising: providing a medium, the medium comprising a semicontinuous metal film of randomly distributed metal particles and their clusters at approximately their percolation threshold; exciting the medium with a light source; and detecting light emitted from the doped medium in the near-field zone. The medium can also include a microcavity/microresonator along with semicontinuous metal film.

The invention is additionally of a device for cryptography, coding and decoding information comprising: a medium, the medium comprising a semicontinuous metal film of randomly distributed metal particles and their clusters at approximately their percolation threshold; a light source incident on the medium; one or more near-field detectors of light emitted from the medium; and a logic component that compares a detected light pattern with an expected pattern. The medium can also include a microcavity/microresonator along with semicontinuous metal film.

The invention is also of a method for cryptography, coding and decoding information comprising: providing a medium, the medium comprising a semicontinuous metal film of randomly distributed metal particles and their clusters at approximately their percolation threshold; exciting the medium with a light source; detecting light emitted from the medium in the near-field zone; and comparing a detected light pattern with an expected pattern. The medium can also include a microcavity/microresonator along with semicontinuous metal film.

The invention is further of an enhanced optical limiting material and device comprising: a medium, the medium comprising a semicontinuous metal film of randomly distributed metal particles and their clusters at approximately their percolation threshold; and an optical limiting material placed proximate the medium.

The invention is yet further of a microlaser comprising: a medium, the medium comprising a semicontinuous metal film of randomly distributed metal particles and their clusters at approximately their percolation threshold; an optically active material; a light source incident on the medium and the optically active material; and a microcavity.

The invention is still further of an optical amplifier comprising: a medium, the medium comprising a semicontinuous metal film of randomly distributed metal particles and their clusters at approximately their percolation threshold; and a light source incident on the medium. In the preferred embodiment, the optical amplifier additionally comprises a layer of coating material selected from molecules, nanocrystals, and nanoparticles placed proximate the medium. The optical amplifier preferably additionally comprises a microcavity/microresonator.

The invention is also of an optical amplification method comprising: providing a medium, the medium comprising a semicontinuous metal film of randomly distributed metal particles and their clusters at approximately their percolation threshold; providing an input signal; and exciting the medium with a light source. In the preferred embodiment, a layer of coating material selected from molecules, nanocrystals, and nanoparticles is placed proximate the medium. A microcavity/microresonator is also preferably provided.

The invention is additionally of an optical switch comprising: a medium, the medium comprising a semicontinuous metal film of randomly distributed metal particles and their clusters at approximately their percolation threshold; and a light source incident on the medium. In the preferred embodiment, a layer of optical switching material selected from molecules, nanocrystals, and nanoparticles is placed proximate the medium. A microcavity/microresonator is also preferably provided.

The invention is further of an optical switching method comprising: providing a medium, the medium comprising a semicontinuous metal film of randomly distributed metal particles and their clusters at approximately their percolation threshold; providing an input signal; and exciting the medium with a light source. In the preferred embodiment, a layer of coating material selected from molecules, nanocrystals, and nanoparticles is placed proximate the medium. A microcavity/microresonator is also preferably provided.

The invention is yet further of a super density optical recording device comprising: a medium, the medium comprising a semicontinuous metal film of randomly distributed metal particles and their clusters at approximately their percolation threshold; a layer of photosensitive materials placed proximate the medium; a light source incident on the medium; and one or more near-field detectors of light emitted from the medium and the layer of photosensitive materials.

The invention is still further of a super density optical recording method comprising: providing a medium, the medium comprising a semicontinuous metal film of randomly distributed metal particles and their clusters at approximately their percolation threshold; providing a layer of photosensitive materials placed proximate the medium; exciting the medium and photosensitive materials with a light source; and detecting light emitted from the medium and photosensitive materials in a near-field zone.

The invention is also of a photochemical enhancing device comprising: a medium, the medium comprising a semicontinuous metal film of randomly distributed metal particles and their clusters at approximately their percolation threshold; and a photochemical agent placed proximate the medium. In the preferred embodiment, there may be an additional component comprising a highly porous dielectric matrix.

The invention is additionally of a photochemical enhancing method comprising: providing a medium, the medium comprising a semicontinuous metal film of randomly distributed metal particles and their clusters at approximately their percolation threshold; providing a photochemical agent placed proximate the medium; and exciting the medium and photochemical agent with a light source. In the preferred embodiment, there may be an additional step of providing a highly porous dielectric matrix.

The invention is further of a photobiological enhancing device comprising: a medium, the medium comprising a semicontinuous metal film of randomly distributed metal particles and their clusters at approximately their percolation threshold; and a photobiological agent placed proximate the medium. In the preferred embodiment, there may be an additional component comprising a highly porous dielectric matrix.

The invention is yet further of a photobiological enhancing method comprising: providing a medium, the medium comprising a semicontinuous metal film of randomly distributed metal particles and their clusters at approximately their percolation threshold; providing a photobiological agent placed proximate the medium; and exciting the medium and photobiological agent with a light source. In the preferred embodiment, there may be an additional step of providing a highly porous dielectric matrix.

The invention is further of sub-femtosecond pulse generation device comprising: a medium, the medium comprising a semicontinuous metal film of randomly distributed metal particles and their clusters at approximately their percolation threshold; a light source, selected from the group of femtosecond pulses and white-light, incident on said medium; and one or more near-field detectors of light emitted from said medium.

The invention is yet further of a method of sub-femtosecond pulse generation comprising: providing a medium, the medium comprising a semicontinuous metal film of randomly distributed metal particles and their clusters at approximately their percolation threshold; exciting the medium with a light source selected from the group of femtosecond pulses and white-light; and detecting the sub-femtosecond pulses using one or more near-field detectors.

A primary object of the present invention is to enhance optical emission of molecules by placing such molecules on or near fractals, and locating them within or on a surface of a microcavity for still further enhancement.

Another object of the present invention is to enhance optical emission of nano-sized particles, quantum dots, by placing the nanoparticles on or near fractals located within or on a surface of a microcavity.

A primary advantage of the present invention is the observed enhanced optical emission and lasing of molecules, or nanoparticles, placed on or near fractals located within or on a surface of a microcavity.

Another advantage of the present invention is the observed surface-enhanced Raman scattering, and other linear and non-linear optical processes of molecules, or quantum dots, placed on or near fractals located within or on a surface of a microcavity.

Another advantage of the present invention is the enhanced optical emission of dye molecules placed on or near fractals located within or on a surface of a microcavity.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIGS. 16–28 adopt the following reference numerals: 10', a medium comprising a semicontinuous metal film of randomly distributed metal particles and their clusters; 12', a light source; 14', a detector located at the same side of the light source; 16', an alternative detector located at the opposite side of the light source; 18', additional layer or layers for structural support and other purposes; 24', a near-field detector located at the same side of the light source; 26', an alternative near-field detector located at the opposite side of the light source; 32', a computerized logic component that compares a detected light pattern with an expected pattern; 42', a layer of optical limiting materials; 52', a microcavity; 54', an energy source; 62', a layer of optical materials such as Raman materials; 64', a layer of optical materials such as Kerr materials; 66', a layer of photosensitive materials; 72', a photochemical agent; 82', a photobiological agent; and 92' a light source selected from the group of femtosecond pulses and white-light.

Figure 1:
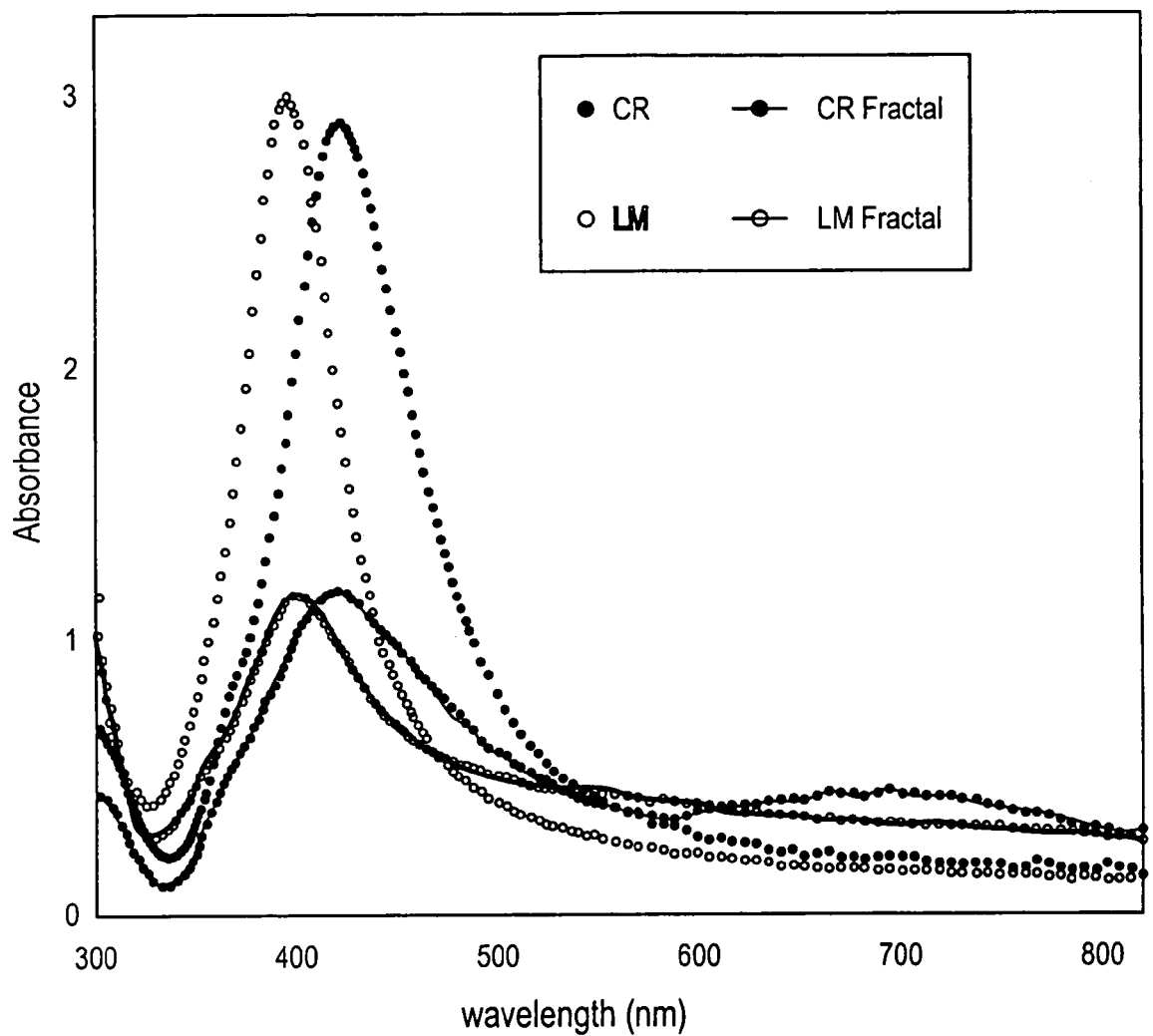
FIG. 1 is an absorption spectrum of a typical bright-yellow colloid solution prepared by the Creighton method, shown by curve CR, and an absorption spectrum prepared according to the Lee and Meisel methods, curve LM, showing the respective absorption spectra of the two.

The detectors 14', 16', 24', 26' may contain polarization selection components (e.g., polarizers), or wavelength discrimination components (e.g., spectrometers), or both polarization selection and wavelength discrimination components.

The optical layers 42', 62', 64', 66', 72', 82' may be located on top of the semicontinuous metal films 10' as shown in FIGS. 6 and 8–12, located under the semicontinuous metal films, or mixed together with the semicontinuous metal films.

DESCRIPTION OF THE PREFERRED EMBODIMENTS

(BEST MODES FOR CARRYING OUT THE INVENTION)

As used throughout the specification and claims, the term "microcavity" means cavity, microcavity, microresonator, and the like.

Throughout the specification and claims, whenever an apparatus, device or method employs the medium of non-aggregated nanoparticles, aggregated nanoparticles, aggregated nanoparticles comprising fractals, semicontinuous films, and/or a semicontinuous metal film of randomly distributed metal particles and their clusters at approximately their percolation threshold, any fractal material may be substituted for the named medium, and the terms "fractal" and "fractal medium" are intended to include all such embodiments when fractal in nature.

In the present invention, nanoparticles—both non-aggregated and aggregated as fractals, microcavities, and fractal/microcavity composites are used to produce various linear and nonlinear optical effects including surface enhanced Raman scattering (SERS), lasing, and surface-enhanced hyper Raman scattering (SEHRS). In general, a light source such as a laser excites a medium comprising nanoparticles, either non-aggregated nanoparticles and/or aggregated nanoparticles. (Fractals are made up of aggregated nanoparticles, preferably 10 nanoparticles.)

Preferably each nanoparticle is of an average diameter that is less than the optical wavelength of interest, and the microcavity has an exterior dimension that is at least twice that of the optical wavelength of interest. Preferably the fractals have a dimension that is less than the embedding space. The nanoparticles are located in the vicinity of a microcavity to further enhance optical emission. To be in the vicinity of the microcavity, the medium can be within the boundary of the microcavity or within a lightwave length of the surface. Either solid or hollow microcavities can be used and the medium can be located on a surface, or contained or embedded within. The medium is typically contained within a liquid suspension, a gel matrix, or a solid matrix. A variety of applications for the use of nanoparticles and/or microcavities are provided.

The nanoparticle medium can be a metal such as silver, gold, platinum, copper, aluminum, or magnesium; semimetal such as graphite; or semiconductor such as Group IV, Group III-V, and Group II-VI semiconductors. Optically active organic and inorganic molecules can be adsorbed on a surface of the nanoparticles, or located within the light wavelength of the surface of the nanoparticles. When discussed herein the adsorbed species can be any molecules, and the invention is not to be limited to the laser dye or sodium citrate molecules discussed below. Various types of laser dyes can be used such as xanthene, coumarin, pyrromethene, styryl, cyanine, carbon-bridged, naphthofluorescein-type, acridone, quinalone derivative, p-terphenyl, p-quaterphenyl, and 9-aminoacridine hydrochloride dyes. Bacterium, inorganic and organic compounds, nucleic acid, quantum dots, quantum wires and such can also comprise the adsorbed species.

The present invention is also a method of doping a material onto the nanoparticle medium, so that the optical emission of a material can be enhanced. These materials can include anything from a single molecule to a plurality of molecules, a nanocrystal, a solid matrix, DNA, DNA fragments, amino acids, antigen, antibodies, bacteria, bacterial spores, and viruses.

Experiments revealing the enhanced optical emissions gained with the present invention will now be described.

Preparation of Silver Colloid Solution.

Silver colloid and silver fractal solutions were prepared using the Creighton method or the Lee and Meisel method. Such solutions can of course be prepared through other known means. All glassware used for the preparation of such solutions were soaked in sulfur-chromic acid for at least two hours, and thoroughly rinsed several times with deionized water. The preparation of silver colloid and silver fractal solutions also requires that the glassware not have any physical damage, such as scratches, because any contamination or scratch on the glassware would cause the unwanted rapid aggregation of colloid particles.

The colloidal preparative methods are based on the reduction of aqueous silver nitrate solutions. The characteristics, such as uniform size and spherical shape, and stability of the prepared colloid solutions is dependent on the reduction agents used and the rate of reduction. The reduction rate was controlled by varying the temperature of the reacting solutions. Both methods achieve the best results by applying vigorous stirring during the initial stages of the reaction. Absorption spectroscopy was used to characterize the prepared colloid solutions.

The resulting colloid solutions and fractals were characterized using a Hitachi H-7000 transmission electron microscope (TEM) with a magnification up to 100,000. Specimens for TEM were prepared by placing a small volume approximately 2 to 5 µl, on a 3 mm diameter carbon-coated membrane supported on a copper grid. A similar method was used for preparation of scanning electron microscopy (SEM) samples.

Creighton's Method

A $1 \times 10^{-3}$ M aqueous solution of silver nitrate $AgNO_3$ (20 ml) at 0° C. was added drop-wise to a $2 \times 10^{-3}$ M sodium borohydride solution, $NaBH_4$ (60 ml) at 0° C. This method generally produced uniform, spherical colloid particles with an average diameter of about 15 nm. A clear yellow color appeared immediately after mixing both solutions. Vigorous stirring was required during the initial mixing process, approximately 5 minutes, followed by slow and gentle stirring for approximately 20 minutes. The solution was transferred to a clean, brown glass bottle, and permitted to come to room temperature (approximately 4 to 5 hours). The solution was then cooled in a refrigerator until needed. Because optical responses depend on the size and shape of the colloid particles, it is necessary that the colloid solutions have a long shelf life. The shelf life, i.e., the non-aggregation stability of these solutions, were monitored by visible absorption spectra (the color changes as fractals become larger) and TEM micrographs. This data revealed that a well-prepared and adequately stored solution remains unchanged for approximately one year.

FIG. 1 shows the absorption spectrum of a typical bright-yellow colloid solution prepared by the Creighton method, curve CR, with a relatively sharp peak at 400 nm. The location of this peak is characteristic of the average size (15 nm) of the particles, and the width corresponds to the distribution of the particle size in the solution. The narrower the width of the peak, the narrower the size distribution.

Lee and Meisel Method

The method of Lee and Meisel was also used to prepare colloid solutions. A 90 mg sample of silver nitrate, $AgNO_3$, was dissolved in 500 mL of distilled water. The solution was heated to reflux, and 10 mL of a 1% solution of sodium citrate added drop-wise with vigorous stirring. The solution was refluxed for 60 to 90 minutes, that is, until the color of the solution gradually changed from transparent to milky yellow to greenish yellow. The temperature of the heating bath was maintained at approximately 125° C. during the reflux period. This procedure ensured the formation of silver nanoparticles (monomers) with an average diameter of 25 nm. Thus, the average size distribution of the nanoparticles were larger than the nanoparticles prepared by the method of Creighton. The solution was permitted to cool to room temperature, after which the solution was poured into a brown glass bottle and placed in a refrigerator. Visible adsorption spectra of non-aggregated silver colloid solutions prepared by the Lee and Meisel method exhibited a single resonance feature of approximately 420 nm with a width of 80 nm as shown in FIG. 1, curve LM.

Preparation of Fractals

Regardless of the preparation method used, the colloid solutions were quite stable for a reasonably long period of time. However, upon the addition of an adsorbate, such as a fumaric acid (approximately 0.03 M) or a solution of a sodium chloride (approximately 0.5 M), to the "monomer" colloid solution, aggregation of colloidal nanoparticles into fractal clusters was observed. Each fractal was estimated as containing approximately $10^3$ monomers. A typical cluster-cluster aggregation process occurs wherein some fractals comprise more than $10^3$ particles and some fractals comprise smaller clusters on the order of 10 to 300 particles.

Electron microscopic analysis of these aggregates demonstrates that they possess a fractal structure with the fractal dimension D~1.77; cluster-cluster aggregation of particles result in D=1.78 by computer simulations. The fractal dimension was obtained by counting the number of monomers within a given region for several different size fractal clusters consisting of 500 to 3,000 particles, and comparing it to the theoretical formula, $N=(R_C/R_0)^D$ of the scaling theory, where N is the number of monomers in a gyration radius $R_C$ of a fractal cluster, and $R_0$ is a constant of length of the order of the minimum separation between particles. The measured fractal dimension is within 1% of the theoretical one.

Aggregation of the nanoparticles into fractals can be inferred by observing the color change of the solutions from yellow to orange, to pink, to blue and finally to gray as well as the appearance of a broad band in the absorption spectrum extending toward the longer wavelengths. The average lifetime before the precipitation of the aggregates from the colloid solution is about two hours.

Fractal/Microcavity Composites

Fractal/microcavity composites comprise aggregated nanoparticle fractal solutions in various stages of aggregation contained within a quartz tube. Preferably, a hollow, fused quartz, cylindrical microcavity was used to investigate the nonlinear behavior of the fractal/microcavity composites. The outside diameter of the microcavity tube was approximately 1 mm and the inside diameter was approximately 0.7 mm. The invention is not limited to cylindrical microcavities, and alternative geometries and sizes are also possible, for example cylindrical microcavities, spherical microcavities, spheroidal microcavities, polyhedral microcavities, and optical wave guide microcavities can be used in accordance with the invention. Because of the small size of the quartz tube, the colloid solutions, both before and after aggregation, were introduced by capillary action.

Figure 2A:
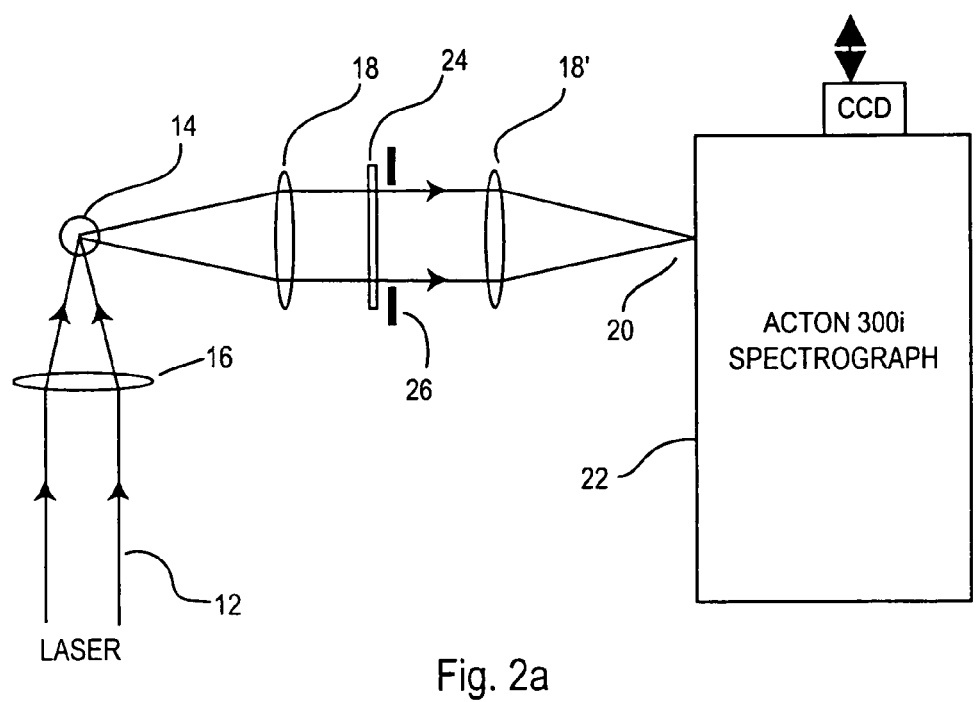
FIG. 2a shows a diagram of the laser optical bench used to measure optical enhancements obtained using the present invention.

Attention is now turned to FIG. 2. FIG. 2a shows a diagram of the laser optical bench used to measure the optical enhancements of the fractal/microcavity. The light source of the invention can be a laser and preferably emits light of wavelengths between approximately 200 and 100,000 nanometers, more preferably between approximately 300 and 2,000 nanometers. The light source power can be anywhere from approximately 1 nanowatt to 100 watts, which can be provided by many types of lasers. In FIG. 2a, one of several continuous wave laser beam light sources, e.g. a He-Ne laser ($\lambda_L$=543.5 nm, 0.75 mW; $\lambda_L$=632.8 nm, 85 mW), or an Argon ion laser ($\lambda_L$=488 nm, 10 mW; $\lambda_L$=514.5 nm, 50 mW) were focused on microcavity 14 containing sample solutions, and used as the pump beam 12. In order to avoid any confusion on data collection due to plasma lines from a laser source, a laser filter with a bandwidth less than 10 nm was used. Pump beam 12 (approximately 2 mm in diameter for a green He-Ne laser and Argon ion laser, 5 mm for a red He-Ne laser) was focused on microcavity 14 by 75 mm focal length lens 16; focal plane beam diameters were 70 μm, 35 μm and 50 μm for Argon lasers $\lambda_L$=488 and 514.5 nm), and for He-Ne lasers ($\lambda_L$=543.5 nm and $\lambda_L$=632.8 nm). The polarization of all pumping sources was vertical along the axis of microcavity 14, and the output radiation was collected at a fixed angle of 90 degrees to the incident radiation by two identical lenses of 100 mm focal length, 18 and 18'. The combination of two identical lenses 18 and 18' makes it possible to collect 1:1 images of excitation spots around a cylindrical microcavity in entrance slit 20 of a 30 cm focal length Acton SpectraPro-300i spectrograph 22.

Figure 2B:
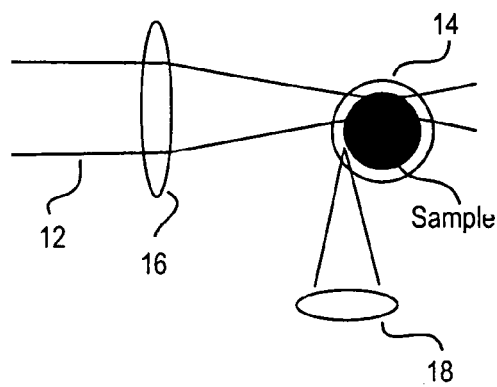
FIG. 2b shows an alternative configuration to that of FIG. 2a when exciting MDRs in the cylindrical microcavity for lasing and hyper-Raman scattering measurements.
Figure 2C:
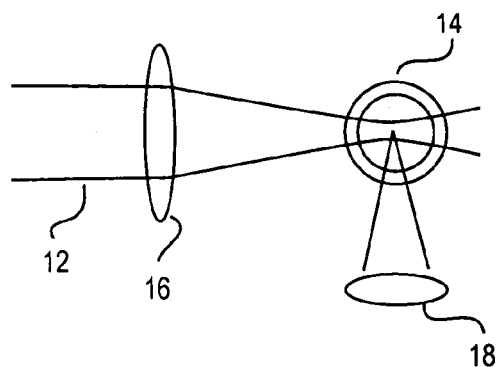
FIG. 2c shows an alternative configuration to that of FIG. 2a when collecting enhancement measurements due only to fractal structures instead of MDR.

Configuration FIG. 2b was used when MDRs were to be excited in the microcavity for both lasing and hyper-Raman scattering measurements. In each case, the position of pump beam 12 was carefully adjusted on the microcavity to excite fractals doped with optically active media such as Rhodamine 6G (R6G) dye molecules for lasing measurements, or sodium citrate molecules for normal and hyper-Raman scattering measurements. The position of pump beam 12 shown in FIG. 2c was used to collect enhancement measurements due only to fractal structures and not the MDR. The ratio of the spectral responses, i.e., with and without the microcavity, is then used to estimate the enhancement factors associated only with the resonant microcavity.

Spectroscopic measurements were performed using an intensified charge coupled device (ICCD) camera (27 μm, 564×384 pixels with Princeton ST-138 controller) mounted to the SpectraPro-300i spectrograph. Two gratings installed in the spectrograph were a 300 groove and an 1800 groove per millimeter grating blazed 500 nm, which provided a spectral resolution of 0.12 nm and 0.04 nm, full width at half maxima (FWHM), respectively. The coarse 300 groove grating was used to obtain a broader range of spectral data, approximately 60 nm around orange range. The finer 1800 groove grating was used to obtain 10 nm or less ranges such that the details of spectra, for example, using this grating, the mode spacing of MDRs could not be obtained.

A set of filters 24 were placed between lenses 18 and 18'. A set of color filters (long pass filters), a few short pass filters, a set of neutral density filters (Oriel) and laser notch filters with optical density 6 at pump laser wavelength were used. For hyper-Raman scattering measurements, a set of metallic density filters (Oriel) ranging from optical density 0.1 to 3 around 500 nm (these filters have a slightly higher optical density in the UV region from 200 to 400 nm) were used. UV-enhanced silica lenses to collect outcoming optical signals were also used. Since optical signals emitted from a microcavity are quite different from one location to another, careful and consistent focusing onto entrance slit 20 is required in order to obtain consistent optical enhancements. Positions of both collecting lenses 18 and 18' were controlled with precision micrometers in order to achieve optimal and consistent optical enhancements from one measurement to another. A set of iris diaphragms shown generally at 26 placed along the collecting path to slit 20 ensured the alignment of the lenses, and eliminated unwanted scattering noises. The width of entrance slit 20 also affected the characteristics of the enhanced optical response. The optimum size of entrance slit 20 is between approximately 10 μm and 50 μm.

Figure 3:
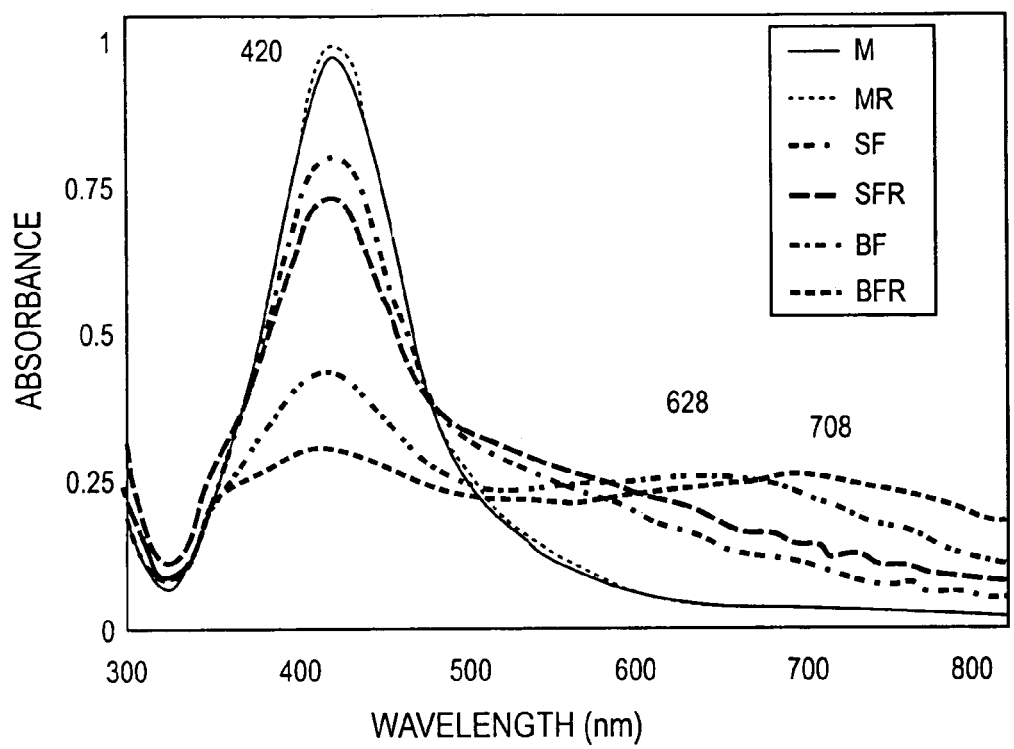
FIG. 3 shows absorption spectra of freshly prepared silver colloid solutions and corresponding fractal aggregates.

Attention is now turned to FIG. 3. Absorption spectra of freshly prepared silver colloid solutions containing non-aggregated particles (M) and non-aggregated particles doped with (5×10$^{-7}$ M) Rhodamine 6G dye molecules (MR) are shown in FIG. 3. The corresponding fractals produced were: small aggregates produced with fumaric acid (SF); large aggregates produced with fumaric acid (BF); small aggregates produced with fumaric acid and doped with R6G (SFR); and large aggregates produced with fumaric acid and doped with R6G (BFR). As shown in FIG. 3, the addition of the dye molecules resulted in a very small change in the absorption spectra, which indicated that the amount of R6G used to optically determine the amount of enhancement caused by the fractal/microcavity composite does not initiate aggregation of the silver colloid particles. Instead, fractals were produced by adding a small amount of an acid solution, such as 0.03 M fumaric acid, citrate acid and so on, or a salt solution. The absorption spectra containing the adsorbate is not significantly dependent upon what adsorbate is used so long as a proper volume ratio for each adsorbate remained constant.

As R6G in methanol is added to the solution of aggregates (SF and BF), an increase in aggregation beyond that initiated by the addition of an adsorbate is observed. See spectra SFR and BFR in FIG. 3. In other words, adding a small amount of R6G, without fumaric acid, to the fresh colloidal solution does not initiate aggregation (see MR), but does promote further aggregation if the acid was initially added (see SFR and BFR).

The order of adding the various components, e.g., acid to dye or dye to acid, does not result in any appreciable difference in the observed absorption spectra, however the lifetime of the samples was affected. For example, when R6G is added prior to the addition of the acid adsorbate a shorter lifetime, and increased rate of fractal precipitation, was observed. Although optical enhancement is similar in both cases, it is preferred that the R6G be added to the adsorbate-produced fractals because the lifetime of the fractal solutions is greater, thus providing more time to record optical response measurements. Also, optimal optical enhancements were observed when R6G was added to a solution approximately thirty minutes after the adsorbate was added.

Lasing of R6G Doped on Fractals in Microcavities.

Lasing experiments were performed with R6G dye/fractal/microcavity composites. A small amount of a $10^{-4}$ M R6G solution in methanol was added to a silver fractal solution; the resulting dye concentrations in the samples ranged from $10^{-5}$ to $10^{-8}$ M. Cylindrical microcavities were fabricated from cylindrical quartz tubes having an inner diameter of 0.7 mm, and an outer diameter, 1.0 mm. The fractal/dye samples were prepared about thirty minutes before the lasing measurement. It is proposed that some time is needed for the dye molecules to become adsorbed on the fractals.

Figure 4:
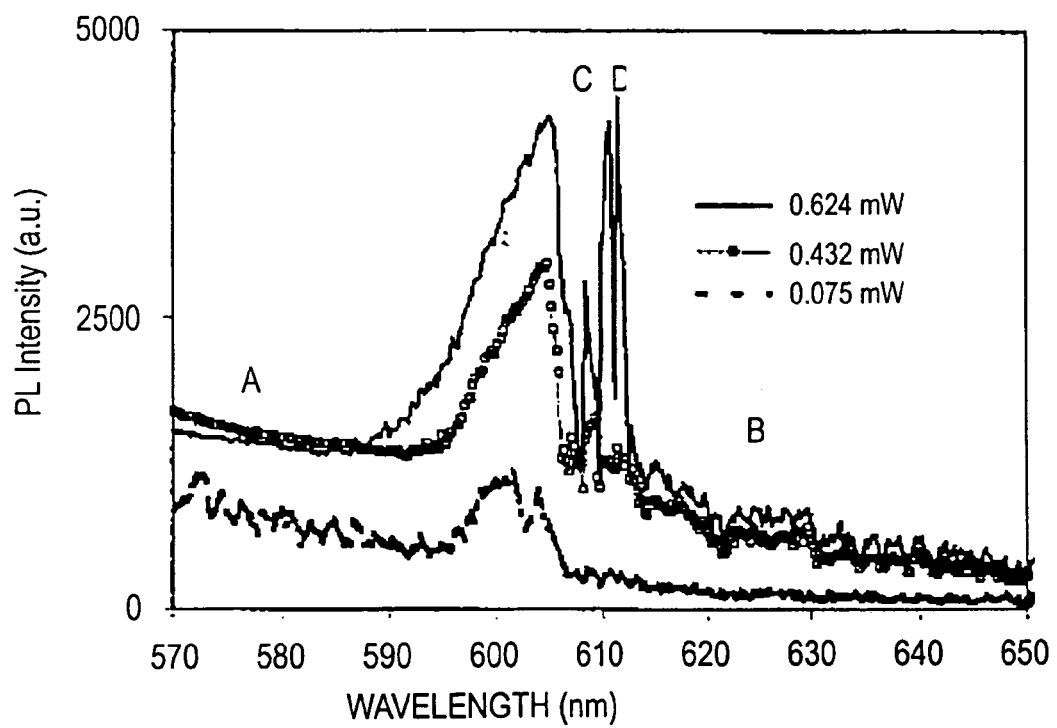
FIG. 4 shows photo luminescence (PL) spectra at different intensities of the pump beam from dye molecules doped on silver particles, wherein luminescence spectra are denoted at A and B, and peaks due to lasing are denoted at C and D.
Figure 5:
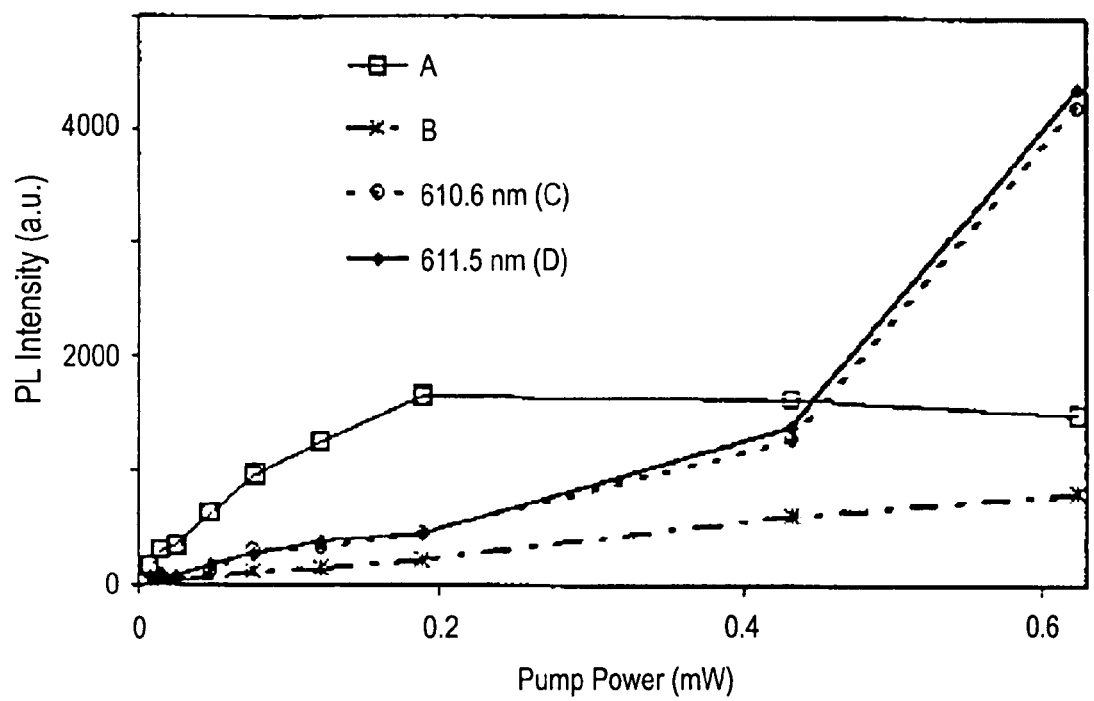
FIG. 5 shows A, B, C, and D of FIG. 4 as a function of pump power.
Figure 6:
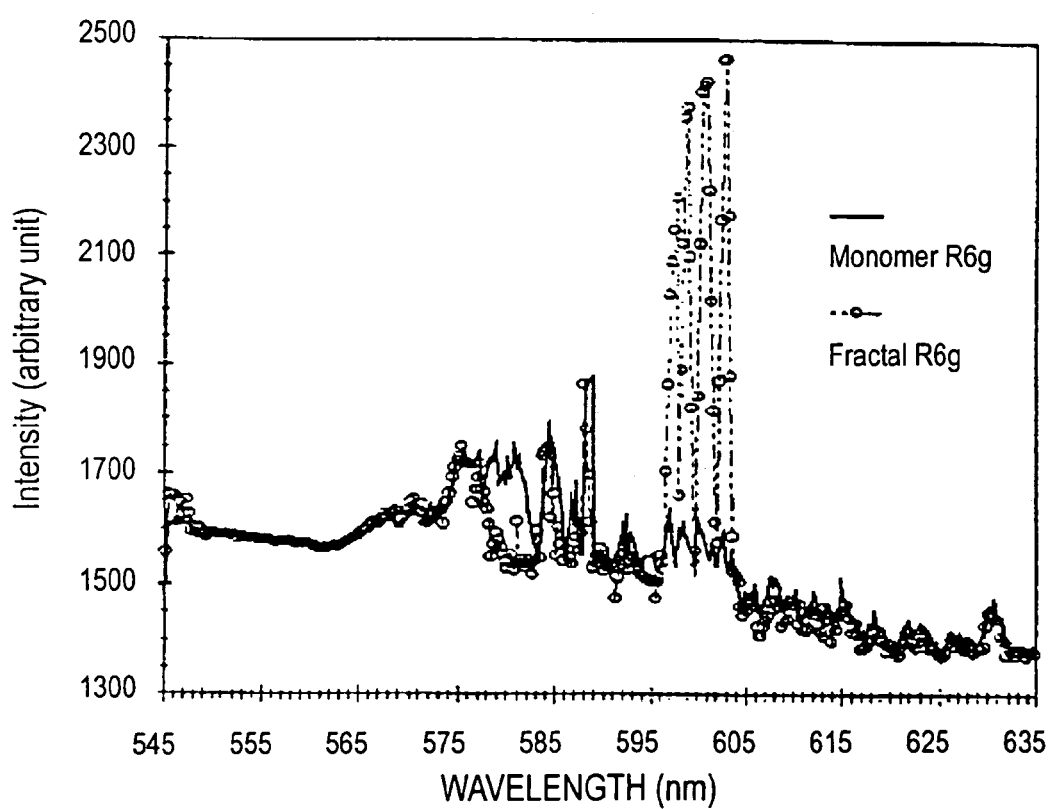
FIG. 6 compares the difference between enhancements in Rhodamine 6G dye molecules adsorbed on silver monomer and fractals.

The emission intensity of different spectral components as a function of the pump intensity were measured. Attention is now turned to FIG. 4. FIG. 4 shows the photoluminescence spectra at different intensities of the pump beam (He-Ne laser; $\lambda_L$=543.5 nm). Luminescence spectra from dye molecules doped on silver particles are denoted as A and B. Peaks C and D corresponds to lasing. Turning to FIGS. 5 and 6; FIG. 5 shows the threshold dependence of the lasing lines and FIG. 6 shows the actual lasing spectrum. For comparison to FIG. 4, FIG. 5 shows the threshold effect for lasing (C and D) as well as the pump power dependence of spectral components A and B. Although a sample containing large fractals was used (1~2 μm size for approximately 3,000 monomers in an average fractal), the spectrum for low intensity irradiation, which is the bottom dashed line in FIG. 5, is quite similar to that of monomers. Note that the luminescence signal from non-aggregated monomers shown in FIG. 6 is quite similar to the bottom spectrum in FIG. 5.

The dependence of luminescence intensity on pump power is linear for low excitation intensities for all spectral components, as shown by FIG. 5. However, when the pump intensity exceeds some critical value in the range between 20 and 50 W/cm$^2$, some peaks grow dramatically, exhibiting a lasing threshold dependence as shown in FIGS. 4 and 5. The threshold power for the $\lambda_L$ which=543.5 nm He-Ne pump laser is as small as $2 \times 10^{-4}$ W. It is noteworthy that the R6G concentration was only $5 \times 10^{-7}$ M which corresponds to a maximum of 230 dye molecules per nanoparticle if all dye molecules adsorbed on the surface of silver particles, which is three orders of magnitude lower than that for conventional dye lasers with an external cavity in the absence of fractals, and three orders of magnitude less than that for a micro-droplet laser without silver fractal aggregates. In contrast, the minimum R6G concentration required for lasing with fractals contained within microcavities is as low as $10^{-8}$ M. Also, the threshold pump intensity used with fractal/microcavities was approximately three orders of magnitude less than a conventional dye laser. These results indicate that the lasing effect is due to dye molecules adsorbed on the surface of silver aggregates.

Therefore, surface-plasmon-enhanced radiation effects in fractal/microcavity composites lead to dramatic lasing effects. This conclusion is supported by the fact that increasing the R6G concentration up to $10^{-5}$ M does not result in additional growth of the lasing peak intensities. In such cases, the greater dye concentration is apparently too large to be adsorbed onto the silver particles, and the additional dye, remaining in solution as free molecules, does not effectively contribute to lasing. Therefore, the presence of metal colloid particle fractals contained within the resonant microcavity is the main contribution to linear and nonlinear optical enhancement.

The placing of R6G dye in a microcavity leads to $10^3$ to $10^5$ enhancement of the dye photoluminescence. By adding non-aggregated silver colloidal particles to the dye solution in a microcavity, further (multiplicative) enhancement is obtained, varying between $10^2$ and $10^3$. Finally, aggregation of the colloidal particles into fractals in the microcavity results in an even greater enhancement, which can be as large as $10^4$. The resultant (multiplicative) enhancement obtained was in the range between $10^9$ and $10^{12}$, on average, and several orders of magnitude more, in the fractal hot spots.

In order to compare the enhancement quantitatively, a set of neutral density filters, with a total optical density between 2 and 3, were placed before the entrance slit of a spectrograph in the case of large fractal measurements. As shown in FIGS. 5 and 6, the photoluminescence of non-aggregated silver colloid particles (monomers) is quite similar to the dashed spectrum, 0.075 mW, in FIG. 4. Thus, the overall emission enhancement resulting from adsorption of the dye molecules on the surface of the fractals in a microcavity can vary between $10^9$ and $10^{12}$. FIG. 6 reveals the difference of the enhancements in Rhodamine 6G dye molecules adsorbed on silver monomers and fractals. As shown, the fractal spectrum (dashed line) was reduced by a factor of $10^3$ because an optical density 3 filter was placed in the path of the collection optics.

The lasing effect depends on both the spontaneous emission rate of the adsorbed dye molecules, as well as the enhancement created by the pump and the generated beams within the microcavity. The spontaneous rate of a particle in a resonator differs from the rate in a vacuum, i.e., the Purcell effect, because the density of photon states is modified by the resonator. The spontaneous emission rate $\Gamma$ is proportional to the photon density of states $\rho(\omega)$, and gives the enhancement factor (Purcell factor $F_p$) in a resonant cavity compared to the emission in vacuum as:

$$F_P = \frac{\Gamma}{\Gamma_0} \sim Q\left(\frac{\lambda}{L}\right)^3, \quad (1)$$

where the subscript 0 denotes the vacuum and L denotes the length of the microcavity. If optically active molecules, such as dye molecules, are adsorbed on the surface of a fractal, additional strong enhancement can be achieved due to enhancement of the zero-point, or vacuum, field fluctuations in fractals. Thus, the combined effect of a microcavity ("conventional" Purcell effect) and the local-field enhancement of zero-point fluctuations due to the plasmon modes in fractals can result in a dramatic modification of the spontaneous emission rate.

With the assumption of low concentration of fractals in the cavity, the surface-enhanced Purcell factor $F^{SE}$ for a dye/fractal/microcavity composite is a product of $F_p$ and the local-field factor:

$$G = \frac{\langle |E(r)^2| \rangle}{|E_0|^2} \text{ as} \quad (2)$$

-continued $$F^{SE} = \frac{\Gamma}{\Gamma_0} = \frac{\langle |d|\rangle^2}{|d_0|^2} \frac{\rho(\omega)}{\rho_0(\omega)} \sim GQ\left(\frac{\lambda}{L}\right)^3 \quad (3)$$

Although the cylindrical microcavity used is too large to observe the conventional Purcell effect, multiplicative enhancements of lasing results from the "classical" enhancement of the pump and generated beams as well as from the "quantum" factor characterizing the predicted modification of spontaneous emission due to the localized plasmon modes in fractals. See equation (1) above.

Photo Initiated Aggregation of Colloid Particles.

A pronounced time-dependent effect was observed when a fresh silver colloid solution was irradiated with a CW, 543.5 nm green He-Ne pump laser at a power of 0.75 mW. Initially, the solution contained non-aggregated silver particles doped with Rhodamine 6G dye molecules. The overall concentration of R6G dye in the solution was $5\times10^{-7}$ M, which is not enough to generate strong lasing emission in a colloid solution. However, after approximately thirty minutes of irradiation, during which time only extremely weak luminescence was observed, strong lasing emission spontaneously appeared from the microcavity.

It is proposed that this time-dependent lasing effect is due to photo-stimulated aggregation, whereby initially non-aggregated, or weekly aggregated, silver colloidal particles undergo in situ aggregation in response to irradiation by a He-Ne pump laser. In such a case, the aggregated particles, or fractals, are "pulled" into high-field regions of the MDRs as a result of electromagnetic gradient forces, and resonant multiplicative enhancement is sufficient to lower the lasing threshold to the level provided by the He-Ne pump laser. As a result, the measured overall enhancement of the light emission due to the combined effects of the resonant microcavity and fractals is between approximately $10^{10}$ and $10^{12}$.

During the photo-initiated aggregation experiment several different procedures were tried in order to investigate how the pump beam influenced aggregation of the colloid solution. What was observed was that the lasing effect was dependent upon the localized position of the light source, or pump beam, on the resonant microcavity. As the pump beam was moved approximately 100 μm away from the initial position where dramatic lasing emissions were observed, the lasing emission disappeared. However, the lasing emissions reappeared at the new position after about forty minutes. After blocking the pump beam for approximately thirty minutes a strong lasing emission at both the new and the original positions were observed. Several measurements confirmed that the approximate time needed for the nanocomposites to migrate and aggregate was between approximately twenty to thirty minutes. The lasing emissions last between approximately one to two hours. After which the silver aggregates grow too large and precipitate out of the solution. In fact, even without the pump beam, an initial colloidal solution becomes transparent, and precipitated aggregates become visible at the bottom of the microcavity after several hours. This indicates that ambient room light is sufficient to photo-aggregate colloidal particles in the microcavity, because fresh colloid solutions in a microcavity can be stored in the dark for up to approximately two months.

Morphology Dependent Resonance with Fractals in Microcavities.

The enhancement factor for Raman scattering of a fractal solution was found to be $10^5$ to $10^7$. However, when that same solution was placed within a microcavity, an additional enhancement factor on the order of $10^3$ to $10^5$ was observed. This demonstrates the unique potential of fractal/microcavity devices in the development of ultra-low threshold microlasers, of linear and nonlinear optical devices for photonics, as well as new opportunities of micro-analysis, including spectroscopic studies of single molecules. Several applications in particular are described in the examples below.

Elastic scattering of a laser beam passing through an outer edge of an empty cylindrical tube exhibits well-defined, MDR angular structure. In contrast, when the beam passes through an inner edge of an empty tube, the MDR intensity is significantly less. Consequently, optimal enhancements were observed using inner edge illumination geometry because it provides the effective optical excitation of fractals within the cavity and their coupling to the MDRs. Filling the tube with a colloidal solution resulted in strong elastic scattering with a clearly resolved MDR angular structure. This indicates that light scattering by colloidal particles facilitates trapping of the radiation in the MDR cavity modes. Elastic scattering by fractals and monomers also contributes to output-coupling of radiation from microcavity MDRs. Scattering, together with absorption, decreases the quality-factor, $Q^{-1}$, of the cavity modes according to $$\frac{1}{Q} = \frac{1}{Q_A} + \frac{1}{Q_{SS}} + \frac{1}{Q_{SV}} \quad (4)$$

where $Q_A^{-1}$, $Q_{sv}^{-1}$ and $Q_{ss}^{-1}$ are losses due to absorption, volume scattering, and surface scattering, respectively.

Figure 7:
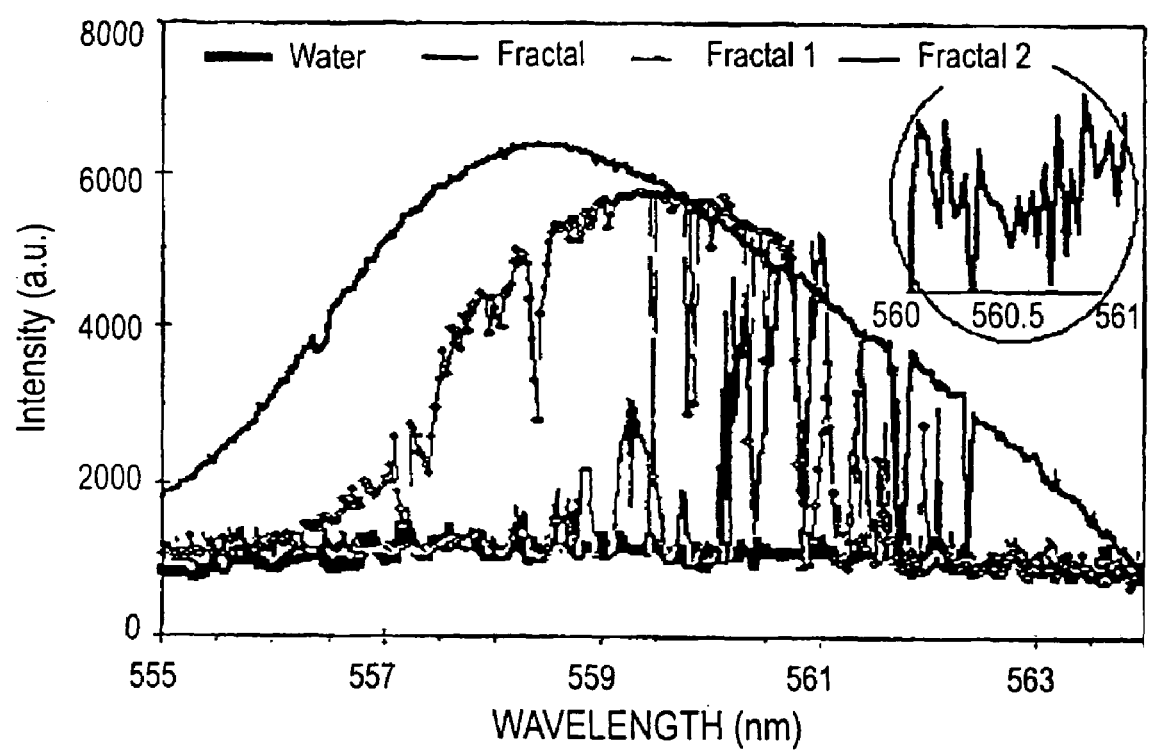
FIG. 7 shows the luminescence spectrum of water and the corresponding fractal enhanced spectra of Rhodamine 6G dyes doped on silver colloid fractals within a microcavity.

FIG. 7 contrasts the luminescence spectrum of a dye solution ($5\times10^{-7}$ M), with and without the presence of fractals in a microcavity ($\lambda_L$=514.5 nm excitation; Argon-ion laser). The volume ratio of water and methanol is 200:1 in both cases. A weak, broad luminescence band is observed with a maximum near 560 nm and a FWHM of 30 nm without colloidal particles or fractals in a microcavity under the $\lambda_L$=514.5 nm excitation. The presence of fractal aggregates of silver colloidal particles results in large peaks in the spectrum with the mode spacing of 0.066 nm. See insert of FIG. 7. This spacing is close to, but somewhat less than the calculated inter-mode spacing, $$\Delta\lambda = \frac{\lambda}{2\pi a} \frac{\tan^{-1}\left(\sqrt{n^2-1}\right)}{\left(\sqrt{n^2-1}\right)} \quad (5)$$

which becomes approximately 0.076 nm for a quartz, refractive index n=1.46, cylinder of radius a=0.5 mm and water as host medium ($n_h$=1.33).

The emission spectrum with 10 mW Argon ion laser pumping of an aggregated silver colloid solution with a R6G concentration of $5\times10^{-7}$ M, differs dramatically from that of the pure R6G solution. A heavy, gray-colored curve denoted "Fractal" in FIG. 7 illustrates the huge increase in peak intensities in a narrow spectral region centered near 561 nm with a bandwidth of approximately 3 nm. The mode structure in this spectral range is approximately the same as for a pure dye solution in a cavity with no fractals. This indicates that the presence of fractals in a microcavity does not appreciably perturb the cavity MDRs. Fractal, Fractal 1, and Fractal 2 spectra in FIG. 7 represent spectra taken with an optical density 2 filter in place and for different CCD detection exposure times, 1, 2, and 3 seconds, respectively. "Water" signals are obtained without the optical density 2 filter, and with 1 second exposure time of the CCD. Simple scaling gives a $10^4$-time enhancement caused by the presence of fractals doped with dye molecules. Thus, the maximum optical enhancement around the 561 nm region may reach up to $10^5$ or $10^7$.

Surface-Enhanced Raman Scattering of Sodium Citrate.

SERS spectra from sodium citrate molecules adsorbed on silver fractal aggregates were obtained under two experimental geometries where MDRs either were, or were not, excited. See the geometries shown in FIGS. 2b and 2c, respectively. Of greater interest is the coupled, multiplicative enhancement factor caused by both fractals and microcavities. By comparing Raman signal levels from sodium citrate adsorbed on silver colloid aggregates with a high concentration sodium citrate solution without colloidal particles, a SERS enhancement of $10^5$ to $10^7$ was observed for the fractal solution. Thus, by adding the SERS enhancement due to the resonant microcavity, the total average enhancement of a fractal/microcavity composite is estimated to be approximately between $10^8$ to $10^{12}$. This large enhancement occurs in spite of the presence of fractals in a microcavity which is expected to decrease its quality-factor as a result of absorption and scattering. Further, since the optical excitations are localized in small nanometer-size hot spots, the local enhancement in these hot spots is expected to exceed the average enhancement factor by 5 to 6 orders of magnitude.

As a result, the maximum local SERS enhancement can be as large as $10^{13}$ to $10^{18}$. These enhancement factors are comparable with, and exceed, the previously reported local enhancements for single molecule SERS of $10^{12}$ to $10^{15}$. Thus, by placing fractal nanostructures in a microcavity or coating them on the outer surface of a microcavity new possibilities exist for optical micro-analysis and detection. In addition, the invention provides for the spectroscopic investigation of lasing and nonlinear optical effects of single molecules, or quantum dots, including semiconductor quantum dots.

Figure 8:
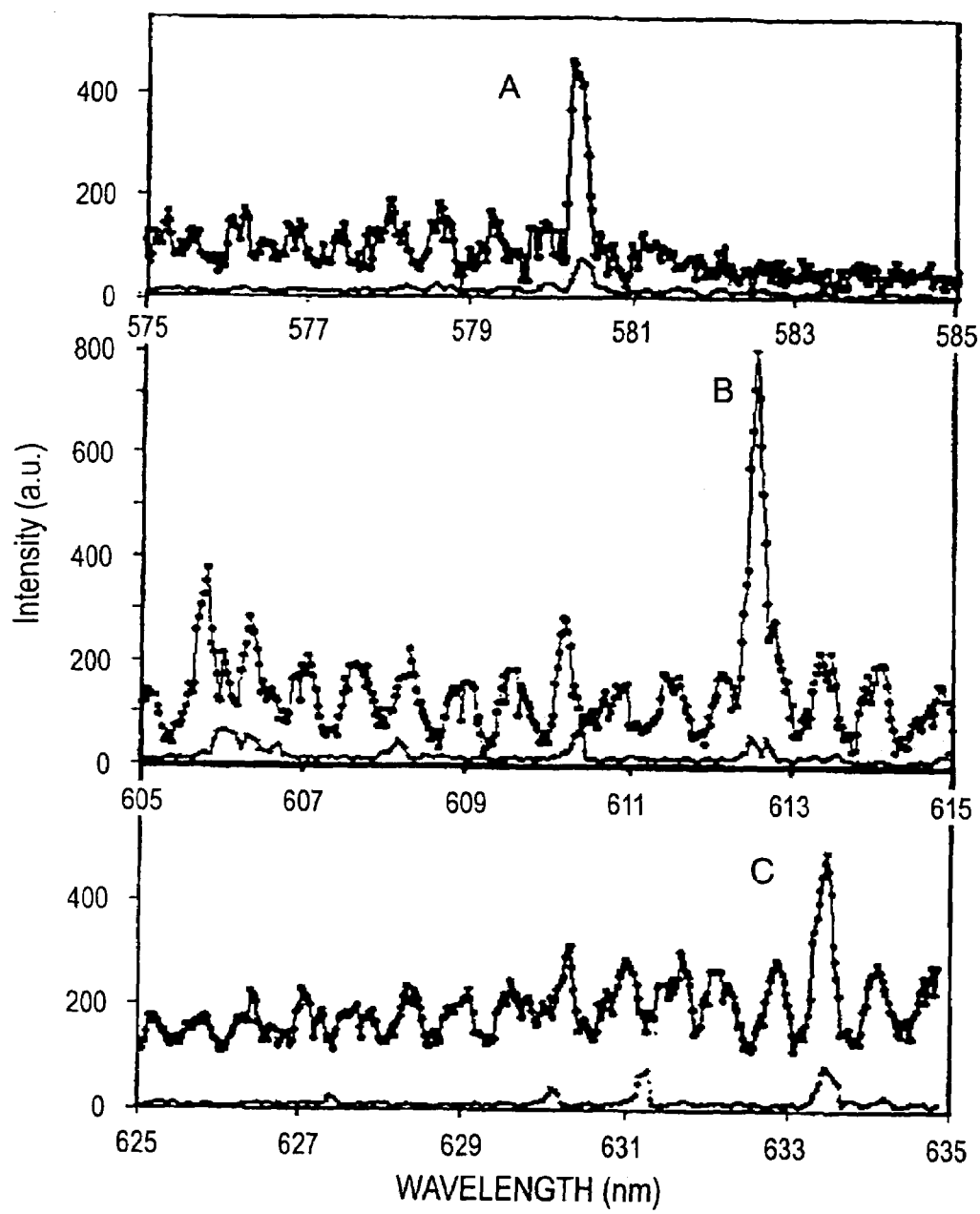
FIG. 8 shows microcavity Raman spectra of aggregated silver monomers without Rhodamine 6G dye under Helium Neon laser excitation.

FIG. 8 shows the difference in microcavity spectra of non-aggregated silver monomers without R6G dye (lower trace), and with fractal aggregates containing a $5\times10^{-7}$ M dye solution (upper trace) under $\lambda_L$=543.5 nm He-Ne excitation. FIG. 8 shows three fragments of this spectrum between 575 nm and 635 nm. The top solid-lines represent spectra of the dye-doped fractals of silver colloid particles; the bottom dashed lines show spectra of non-aggregated colloidal particles without dye molecules doped. Addition of a sodium citrate solution (0.1 M concentration with 1/200 volume ratio) resulted in aggregation of the silver monomers. Analogously to the case of Argon-ion laser excitation, a set of peaks whose minimal spacing is approximately equal to the intermode spacing of the cylindrical microcavity was observed. The observed width of the peaks essentially corresponds to the instrumental width, so that the real peak width is actually smaller than the measured value $\delta\lambda$=0.04 nm. This allows one to estimate a lower bound for the quality factors, $Q>1.5\times10^4$.

Three extremely large amplitude peaks distinguish themselves in the spectra shown in FIG. 8. These peaks at 580.3 (A), 612.6 (B), and 633.4 (C) nm are coincident with spectral features of the luminescence or inelastic light scattering from silver colloid solutions in a microcavity without R6G. The peaks were assigned to the fundamental or combination Raman modes of sodium citrate. The largest peak B at 612.6 nm is the combination Raman mode (1210+850) $cm^{-1}$ of sodium citrate, the peak A at 580.3 nm corresponds to the 1167 $cm^{-1}$ fundamental Raman mode (this mode is usually very weak), and it is proposed that peak C at 633.4 nm is the combination Raman mode (1410+1210) $cm^{-1}$ or (2×850+956) $cm^{-1}$. Interestingly, not all Raman mode of sodium citrate exhibit intense emission. Rather, the presence of MDR modes selects the emission wavelengths to be amplified depending on the spatial location of the emission sources within the cylindrical microcavity.

As stated previously, the local enhancement in the hot spots of fractals in a microcavity is larger than the average enhancement by as many as six orders of magnitude. Using the factor $10^{14}$ for the fractal hot-spot enhancement and taking into account the multiplicative enhancement factor provided by a microcavity, the local enhancement due to the hot spots in a microcavity can be as large as $10^{18}$.

Hyper-Raman Scattering of Sodium Citrate Molecules Attached to Colloid Particles and Their Fractal Aggregates.

Hyper-Raman scattering (HRS) is a nonlinear effect, which results in a scattered photon frequency that is characterized as Raman-shifted relative to the higher order harmonics of the excitation frequency. The shift in frequency provides characteristic vibrational information, such as overtones or combination bands, of the scattering molecules, which cannot be obtained by normal Raman scattering or infrared absorption spectroscopy. SEHRS makes it possible to overcome the practical barriers of the intrinsically low intensity of HRS. Furthermore, additional multiplicative enhancement in MDRs of the fractal/microcavity composites provides information on HRS, two-photon and three-photon processes using weak pump lasers like a conventional, CW He-Ne laser.

Extremely broadband spectra of sodium citrate molecules adsorbed on fractals contained within microcavities from about 200 nm to 800 nm using a He-Ne laser, $\lambda_L$=632.8 nm, pump power between 1 and 50 mW were observed. These peaks consist of fundamental, overtone, and combination band Raman spectra of sodium citrate molecules. Normally, i.e., without the use of fractal/microcavities, it would be only possible to detect multi-photon, hyper-Raman scattering with extremely high intensity pulsed laser sources.

Figure 9:
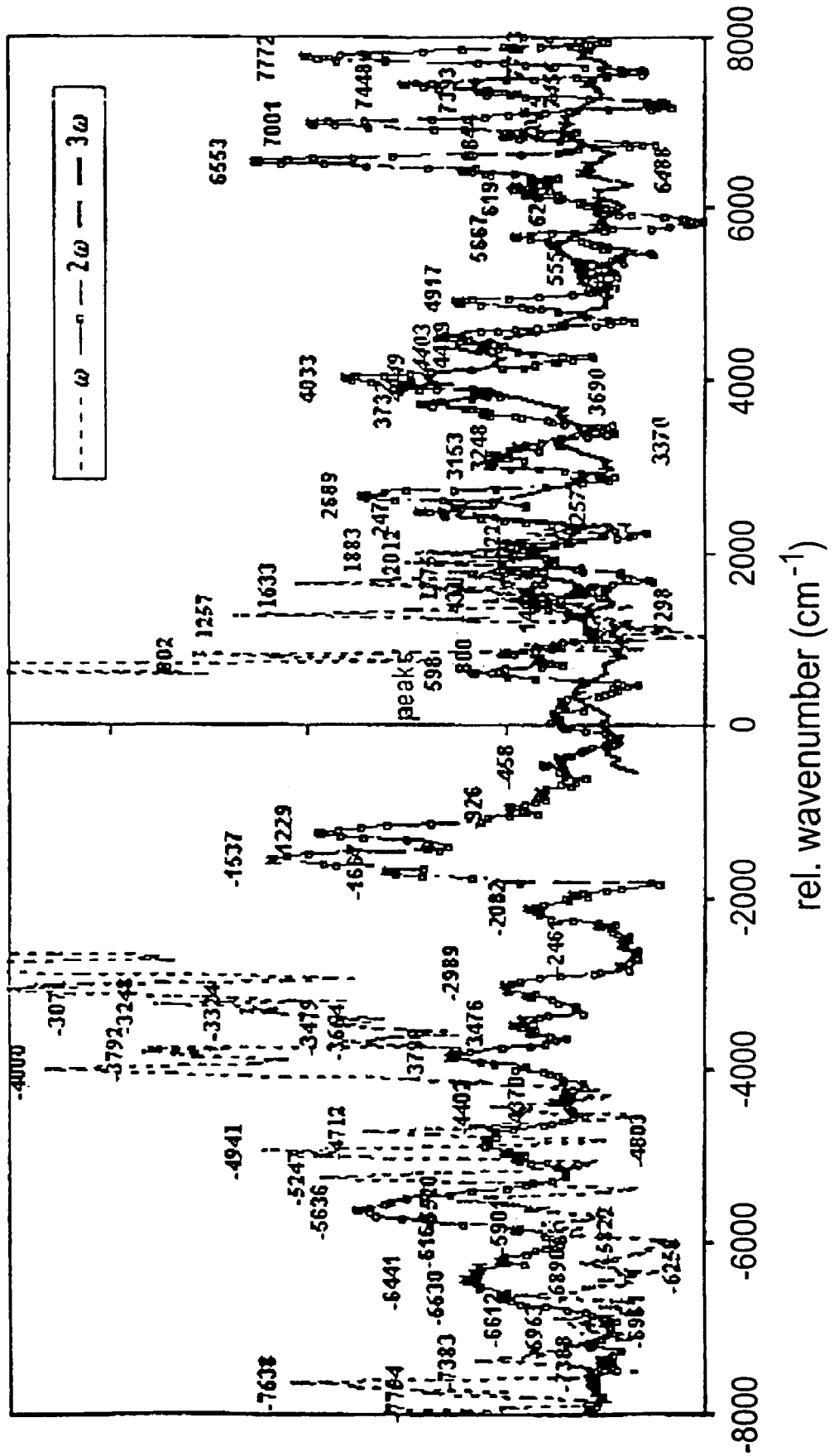
FIG. 9 shows spectra using a conventional Raman-plot for sodium citrate, wherein zero represents the pump frequency; Stokes emissions are plotted on the right and anti-Stokes emissions to the left.

FIG. 9 plots the spectra using a conventional "Raman-plot", where ω denotes the pump frequency, Stokes emissions are plotted to the right, anti-Stokes emissions to the left, and conventional $cm^{-1}$ units are used to denote frequency. The pumps in this plot are: the ω-pump, i.e., the He-Ne laser at 632.8 nm, and the second and third harmonics of the pump laser (the 2ω and 3ω pumps at approximately 316 nm and 211 nm, respectively). FIG. 9 exhibits spectra extending about 8,000 wavenumbers to the Stokes and anti-Stokes sides of the ω, 2ω, and 3ω pump beams. The peaks toward shorter wavelength (2ω and 3ω) regions increase in width since the CCD detector used in this experiment is nearly linear in wavelength, not wavenumber. However, if one accounts for the instrumental error provided by the wavelength separation between adjacent pixels, many sets of Stokes and anti-Stokes Raman bands in the ω, 2ω, and 3ω regions fall within these error margins, i.e., they exhibit the same shifts.

Raman spectra from optically active molecules adsorbed on fractals arise from spatially localized fractal resonance modes, which makes it possible to use less intense pump sources. The enhancement is very large even with fractals not contained within a microcavity. The microcomposites formed by the molecule/fractal/microcavity provides further, multiplicative enhancements of optical responses estimated to be as large as $10^{12}$, for "conventional" Raman and much more for hyper-Raman. For example, the fractal enhancement only for two- and three-photon pumped HRS can be as large as $10^{10}$ and $10^{16}$, respectively. When either the pump or the HRS, or both, waves are coupled to the cavity's MDR, the SEHRS multiplicative enhancement can achieve extremely large values, for example, up to $10^{26}$ for three-photon pumped HRS, provided that both the pump and the HRS waves couple to the MDRs.

Because of this, despite the extremely small hyper-Raman cross-section, the highly nonlinear SEHRS can be obtained in fractal/microcavity composites, even at very low pumps, such as those from He-Ne lasers. The multi-photon hyper-Raman emissions in these systems are fundamental, overtone, and combination scattering of "conventional" Raman bands of the $\omega$, $2\omega$, or $3\omega$ pump light. The $2\omega$ and $3\omega$ light is generated via the processes of two-photon and three-photon absorption in spatially localized regions of fractals contained in cylindrical microcavities.

Sensors of the Invention

Fractal/microcavity composites according to the present invention possess the capability to greatly amplify (by many orders of magnitude) the amplitude of optical signals. As a result, the composites may be used to fabricate extremely sensitive optical sensors. There are two preferred embodiments, depending on whether the optical signal to be amplified is generated on (or within) the composite, or at a point some distance from the composite. In the first configuration, the composite is a contact sensor, and in the second configuration, the composite is a remote sensor.

Contact Sensor

In the contact sensor configuration, light to be amplified is generated on (or within) the composite. Assume that a small number of molecules of a particular type whose presence is to be detected, are adsorbed on the composite. Exciting the composite with light from a suitable laser (such as a pump laser) will cause these molecules to emit characteristic radiation which is then amplified in the composite enabling the presence of extremely small numbers of molecules (including single molecules) to be detected. Photoluminescence and Raman (both linear and nonlinear) emissions are a particularly important source of such radiation because they constitute "fingerprint" emissions from the molecules, enabling both the molecular constituents and their geometric structure to be identified. Because any molecular species adsorbed onto the composite possesses a characteristic photoluminescence and Raman spectrum, the capability of the composite to greatly amplify the photoluminescence and Raman spectrum so that it is easily detectable forms the basis of the universal, highly sensitive contact sensor of the invention.

Figure 12:
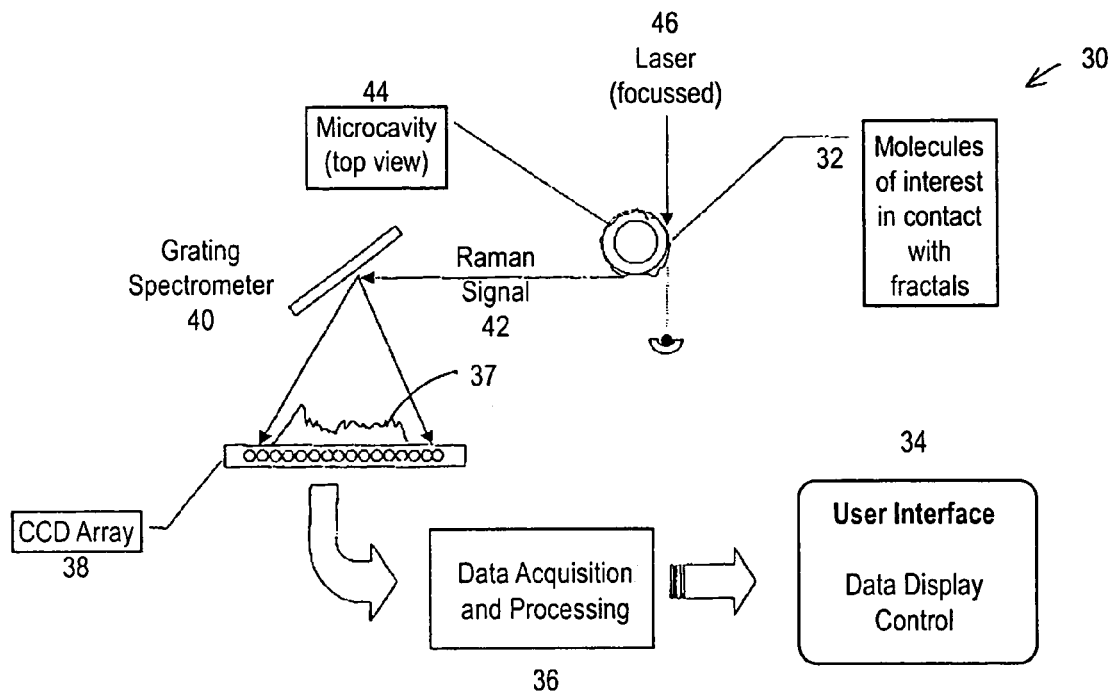
FIG. 12 is a block diagram of the fractal/microcavity composite contact sensor of the invention.
Figure 14:
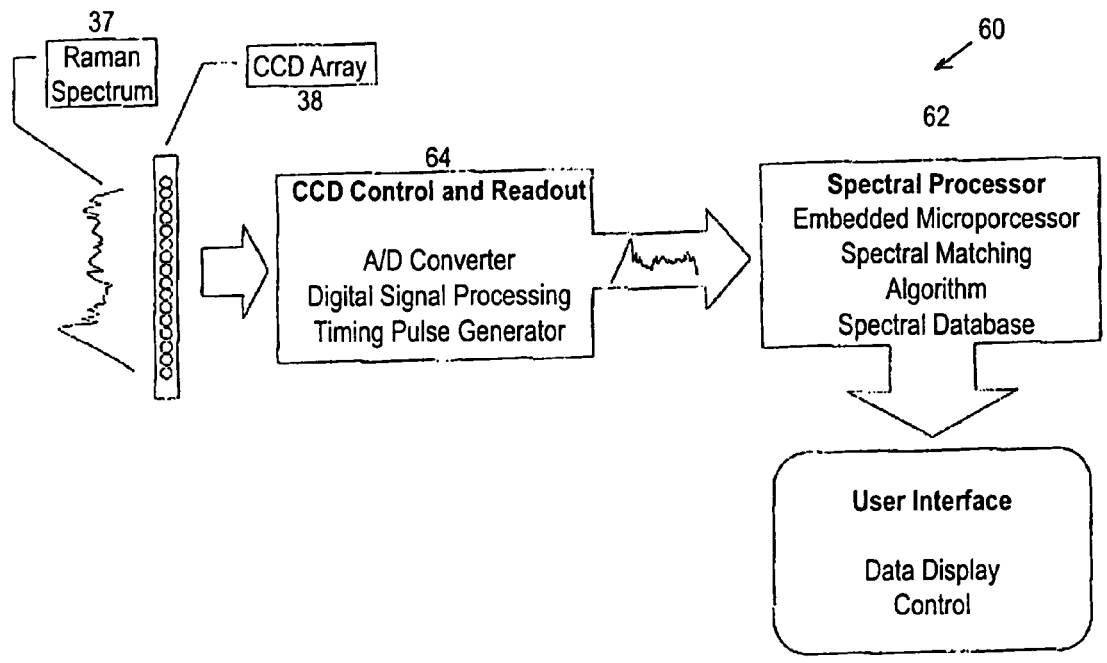
FIG. 14 is a block diagram of data acquisition, processing, and display according to the invention.
Figure 15:
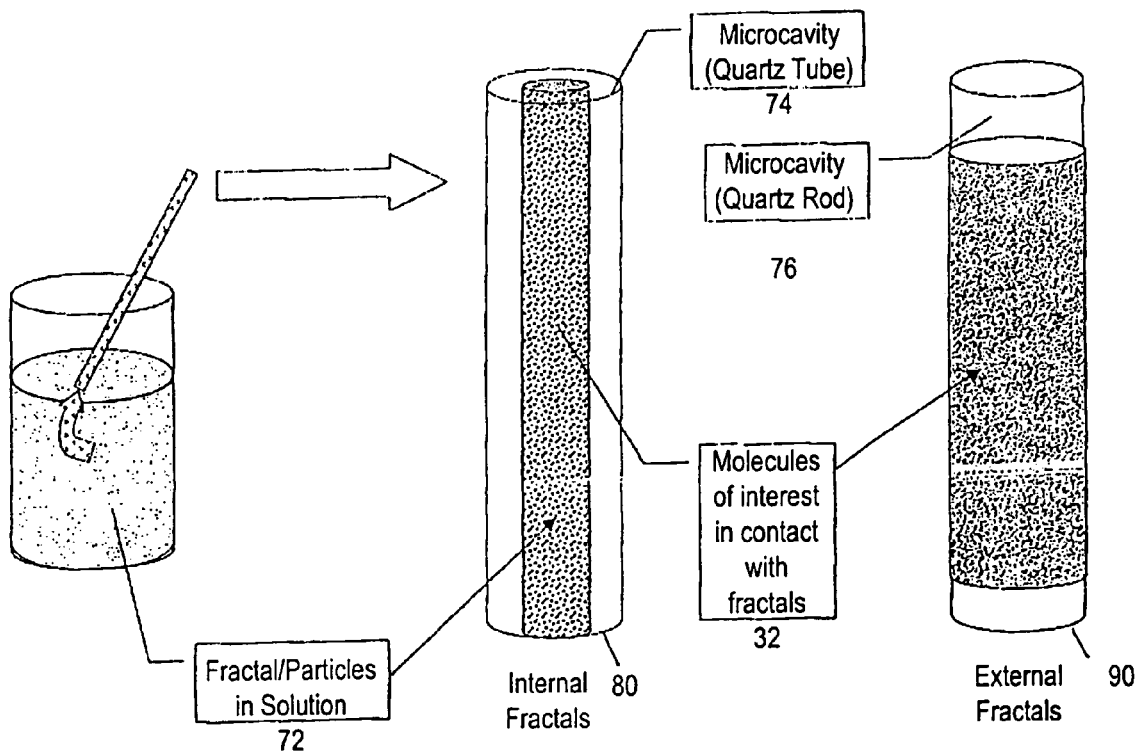
FIG. 15 illustrates preferred embodiments of the fractal/microcavity composite contact sensor of the invention.

FIG. 12 illustrates the preferred contact sensor 30 of the invention. A parent medium is prepared containing the molecules of interest adsorbed onto fractal aggregates 32. A portion of this medium is then deposited either inside the microcavity 44 or as a thin layer on the surface of the microcavity. Referring to FIG. 15 and fractals/particles in solution 72, note that for deposition inside 80, the microcavity (e.g., quartz tube 74) is hollow, whereas for deposition outside 90, the microcavity (e.g., quartz rod 76) need not be hollow. Upon excitation by a suitable laser 46, the molecules emit characteristic fingerprint photoluminescence and Raman emissions 42 which, after being greatly amplified by the composite, permits the number and type of adsorbed molecules to be determined, such as via grating spectrometer 40, CCD array 38, data acqusition and processing apparatus 36, and user inferface and data display and control apparatus 34. As shown in FIG. 14, the data acquisition and processing apparatus preferably comprises CCD control and readout 64, comprising analog-to-digital converter, digital signal processing means, and a timing pulse generator, and spectral processor 62, comprising an embedded microprocessor, spectral matching algorithm means, and a spectral database.

The contact sensor of the invention may usefully be employed to detect chemical or biological warfare agents in or on, e.g., water, air, soil, equipment, structures, agricultural products, and personnel; chemical or biological contaminants of the environment, resulting from natural processes and/or anthropogenic activities, in or on, e.g., water, air, soil, equipment, structures, agricultural products, and personnel; explosive agents; controlled substances (narcotics); chemical or biological agents in manufacturing process streams; and medical and veterinary diagnostic testing for chemical or biological agents in, e.g., blood, blood byproducts, urine, saliva, cerebral spinal fluid, tears, semen, uterine secretions, fecal matter, respiratory gases, and lung secretions.

Remote Sensor

The molecules to be detected and identified are not required to be in contact with the composite. Rather, the light emitted from the molecules needs to interact with the composite, and the remote sensor embodiment of the invention provides such interaction. Assume that the molecules to be detected are at a remote location, not in direct contact with the composite. Characteristic emissions from the molecules (e.g., photoluminescence and/or Raman emissions) excited by a suitable laser falls onto the composite where it the emissions are greatly amplified, permitting the remote detection and identification of the molecules.

The remote sensor configuration exploits an important characteristic of the composites of the invention, namely, as a result of their capability to achieve extremely large amplification of optical signals incident on them, the composites are capable of easily generating so-called "nonlinear" optical emissions. Nonlinear optics is an important area of modern optics, relying on the availability of intense laser pumping sources. However, what makes nonlinear optics in the composites unique is that, as a result of the enormous amplification factors, nonlinear optical effects are easily achieved using extremely weak, low-power lasers. The preferred nonlinear optical process in the context of molecular detection and identification is non-degenerate four-wave mixing (NDFWM). DFWM and NDFWM in composite media possess the characteristic of amplifying any incident optical signal. Accordingly, the combination of the composites of the invention with NDFWM is advantageous for remote sensing applications.

Figure 13:
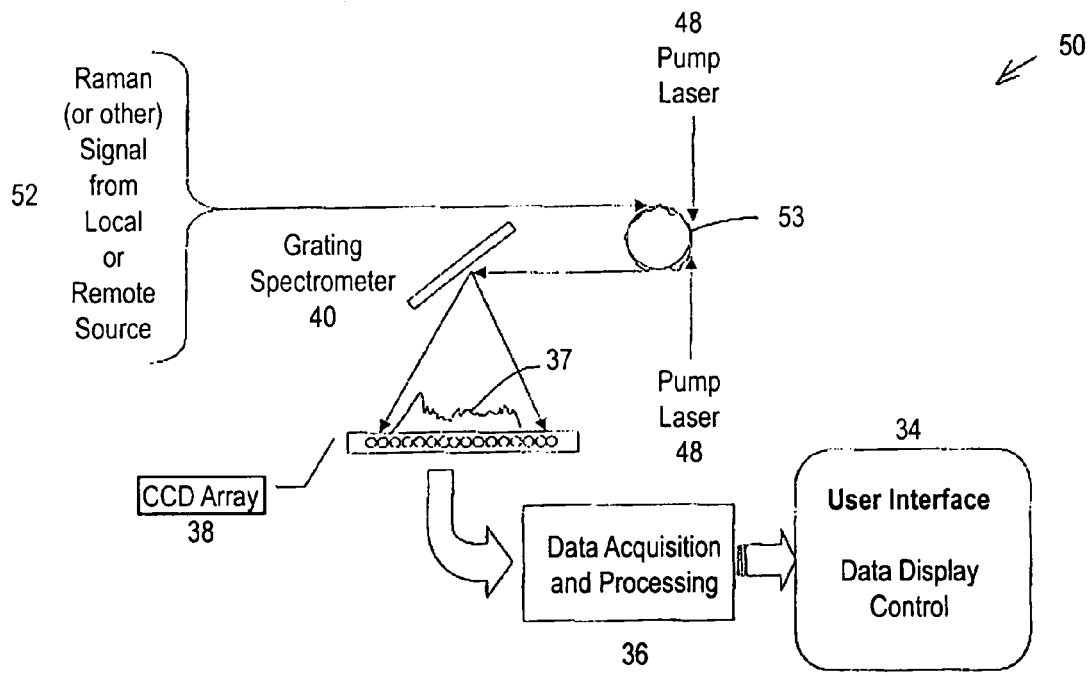
FIG. 13 is a block diagram of the remote sensor/amplifier of the invention utilizing four-wave mixing.

FIG. 13 illustrates the preferred remote sensor 50 of the invention. Photoluminescence ("PL") and/or Raman light 52 from a remotely located collection of molecules falls on the composite 53. In addition, two counterpropagating pump laser sources 48 are incident on the composite. In practice, the pump laser sources may be readily provided by optically separating the light from a single, low-power pump laser into two counterpropagating beams. The presence in the composite of the remotely generated photoluminescence and/or Raman emission and the two counterpropagating pump beams results, via the process of NDFWM, in the generation of greatly amplified photoluminescence and Raman emissions which may be analyzed to detect and identify the unknown molecular species. This analysis may be performed with the aid of an auxiliary spectrometer/CCD detector array or may be directly read from the microcavity emission spectra. The latter method requires calibration of the optical characteristics of the composite and correlation of these characteristics with the observed microcavity emission spectra. In addition to the amplified PL and/or Raman signals, a new beam is generated as a result of the four-wave mixing with the frequency equal to the double of the pump frequency minus the frequency of the PL and/or Raman beams. In some cases, it is easier to detect and analyze this beam, which also bears important information about the PL and Raman signals. It is also important that, provided that frequencies of all the beams are close to each other, the new generated beam has the phase, which is conjugated with respect to the phase of the incoming PL or Raman beams; this fact can be used for restoring information and improving the beam quality. Note that the NDFW can also occur with a single pump beam, provided that the PL and/or Raman beams propagate at the small angle with respect to the pump beam (this is so-called forward propagation four-wave mixing). For practical application, this scheme can be advantageous because of the ease of set-up. The generated signal, in this case, propagates in the same forward direction but from the other side (from the PL or Raman beams) with respect to the pump beam.

Another nonlinear process to employ for a remote detection is difference frequency generation (DFG), the process that is also used in optical parametric oscillators. To occur, this process requires the absence of the inversion symmetry which can be achieved, for example, by depositing fractals on any substrate (which can be a surface of a microcavity) or by using a CD electrical field. The DFG process is due to a second-order optical nonlinearity that can be much larger than the third-order optical nonlinearity required for the four-wave mixing. In the composite materials comprising fractals (alone or in microcavities), the DFG is also dramatically enhanced. Although the enhancement is typically less than in the case of four-wave mixing, the much larger optical nonlinearity of the DFG may result in a bigger signal, in comparison to the NDFW. For the DFG only one pump beam is needed. As a result of the DFG, a light beam at the frequency which is the difference of the pump frequency and the PL or Raman signal frequency is generated, whereas the PL and/or Raman signals are dramatically enhanced. The generated beam propagates in the same direction as the pump and the PL and/or Raman beams, or at the small angle with respect to them.

The remote sensor of the invention may usefully be employed for detection of the items discussed under the contact sensor heading. In particular, the remote sensor may be used in noninvasive medical and veterinary detection of chemical or biological agents, e.g., transdermally, in the aqueous humor of the eye, and in respiratory gases; noninvasive detection of "quality factors" (chemicals) in agricultural products, e.g., water content, pungency factors (e.g., capsaicin in chiles), acids, sugars, and starches; and LIDAR applications including chemical and biological agent defense and satellite applications.

Microcavity Deposition Techniques

The contact and remote sensor configurations differ in that, in the former, molecules to be detected must be in contact with the fractal/microcavity composite whereas, in the latter, only light from the molecules must reach the composite. These requirements may be satisfied by placing the fractal medium within a hollow microcavity or on the microcavity surface (in this case, the microcavity need not be hollow). However, placing the fractals on the microcavity surface results in improved sensor performance for two reasons: first, stronger coupling occurs between the pump laser and the fractal/microcavity composite; and, second, the microcavity resonance modes are of higher quality (i.e., they have a higher Q). Since both of these features result in increased amplification and, hence, improved sensor performance, several potential alternative schemes are considered for placing fractals on the outside surface of a microcavity.

The alternative schemes may be described by contrasting them with the method in which the production of metal (e.g., silver), 10–50 nm diameter, colloidal particles and their fractal aggregates are the product of chemical processes. Viewed in this context, the alternative schemes comprise the replacement of some or all of the steps of the chemical process with non-chemical fabrication methods. These schemes include:

Laser ablation techniques used for deposition on microcavities. These represent the greatest change from the preferred method of the invention, facilitating the evaporation of metal atoms which condense first into metal colloidal particles and subsequently into fractal aggregates in a buffer-gas volume above the metal target. The aggregates subsequently precipitate onto the outer surface of the microcavity where adsorption of, or interaction with light emitted by, molecules to be studied occurs. Fabrication of metal particles in a narrow size range and subsequent aggregation of the particles into fractals requires careful control of the ablation parameters.

Particle deposition techniques. There are several methods of depositing metal particles onto a substrate (for example, the outer surface of a microcavity). The particles may be added to the deposition apparatus (thereby necessitating that they be pre-grown, using, for example, chemical methods), or they may fabricated in the gas phase and then deposited directly onto the substrate. Particles can also be deposited on a substrate from a water solution of non-aggregated colloids so that the following aggregation of particles on the surface of the substrate results in formation of a cluster of particles. In these schemes, if the particles are deposited onto the substrate in a non-fractal geometric pattern, the final fabrication of fractals occurs on the substrate; fractal aggregation on the substrate may be facilitated by optical, chemical, or thermal means. The aggregation of particles can also occur because of diffusion of particles on the surface and can be reinforced by using the substrates where the diffusion of metal nanoparticles is strong, for example, by using the substrates with poor adherence of metal nanoparticles.

Lithographic techniques. These techniques also represent a large modification in the preferred chemical method because they generally involve the direct fabrication of fractal aggregates on the microcavity surface. In these schemes, using either chemical or laser-based etching techniques, fractal media are formed directly from a metal layer covering the microcavity surface. The limiting factor in these techniques is the minimum achievable scale size of the individual fabricated metal particles. In order to duplicate chemically-grown fractal aggregates, particle sizes in the 20 nm range are needed.

Industrial Applicability:

The invention is further illustrated by the following non-limiting examples.

EXAMPLE 1

LIDAR

Light detection and ranging (LIDAR) systems are versatile optical instruments that are currently used in a variety of atmospheric applications. LIDARs may be used to obtain: concentrations of a variety of atmospheric constituents such as chemical compounds, dust, volcanic ash, and water vapor; wind velocity and atmospheric turbulence profiles; and ultra-precise geodesy information. All LIDARs operate in a similar manner; a light source, usually a laser, is directed into the atmosphere through transmitter optics such as an optical telescope where it interacts with the atmospheric constituents. Some of the light produced by this interaction is collected by an optical receiver (typically, the transmitter telescope itself where, for some applications, it is spectrally analyzed, and then input to an optical detector. Optical detectors used in LIDAR systems are typically solid-state photodetectors; although having fairly good optical gain, they are susceptible to noise both from the ambient atmosphere and from the pump laser itself.

The novel characteristics of fractal/microcavity systems discussed above therefore have application to LIDARs. Specifically, light incident on a fractal/microcavity composite is greatly amplified through interactions with either the non-aggregated or aggregated nanoparticles and also with the microcavity resonance modes. In other words, the fractal/microcavity composite of the present invention provides an extremely sensitive optical detector. Raman spectroscopy experiments have repeatedly revealed these sensitive detection properties. In these experiments, extremely weak Raman emission is generated in the fractal/microcavity composite. This emission may be amplified and detected by allowing it to interact with a second optical signal tuned to the same wavelength as the Raman light. Various nonlinear optical interactions may be exploited in this interaction; in these experiments, the process of stimulated resonance Rayleigh scattering was used. However, other nonlinear processes suggest themselves such as four-wave mixing and multi-photon absorption.

In order to realize the process described above with respect to a LIDAR system, the light generated by the atmospheric constituents is input onto a fractal/microcavity composite, irradiated by a suitable pump laser chosen to interact with this light to generate, via a suitable nonlinear process, a light signal to be detected. For the example discussed above, radiation is emitted by an atmospheric constituent, and the pump tuned to this radiation generates enhanced stimulated resonance Rayleigh scattering emission as described above.

Furthermore, a "micro-LIDAR" device has use in a variety of applications. Because of the extremely small size of the fractal/microcavity medium, the micro-LIDAR device can be a hand-held device detecting emissions from a variety of chemical constituents of interest including biological and chemical agents, outgassing from drug and explosive devices, and the presence of poisonous gases such as carbon monoxide.

EXAMPLE 2

OPO

Optical parametric oscillators (OPOs) are useful laser devices that may be tuned in wavelength over a wide range, typically through the visible and near-infrared range. The OPO depends on the nonlinear optical characteristics of materials together with the resonant characteristics of optical cavities. A pump beam is input to a nonlinear optical crystal where it is separated into two beams, a signal beam and an idler beam, wherein the signal is at shorter wavelengths than the pump, and the idler is at longer wavelengths. Under any given operating conditions, the sum of the signal and idler frequencies equals the pump frequency. If the signal or idler beam is input to an optical cavity, the resulting output has all of the characteristics of ordinary laser emission.

To apply the present invention, the nonlinear crystal is replaced by the fractal medium, and the optical cavity is replaced by the microcavity. An incident pump beam excites the signal and idler waves which are greatly amplified by the fractal/composite medium. Coupling the signal and idler beams to microcavity resonance modes (MDRs) produces the output laser emission.

Current OPOs are large, expensive, require high-power pump lasers, are very sensitive to thermal and mechanical effects, and are difficult to keep in proper alignment. An OPO based on the fractal/microcavity system is very small (the size of a microcavity), can be pumped with a very low power pump laser, e.g., a HeNe or diode laser, which is very inexpensive being on the order of a few hundred to a few thousand dollars, has excellent thermal and mechanical stability, and will be virtually alignment-free, because MDRs require no alignment. The OPO is of modest power since the pump power will be small, but for many applications, this is not important; for example, laboratory spectroscopy, chemical, biological, and biomedical analysis, some LIDAR applications such as short-range pollution monitoring, and possibly telecommunications.

EXAMPLE 3

Optical Data Storage

Improvement in data storage capacity is of great importance in computer and video disk technology. Given the fact that the optical gain in fractal media is localized in sub-wavelength regions (hot spots) of the fractal, and different wavelengths are amplified in spatially distinct regions of the fractal, the present invention has further application in data storage technology. By irradiation of the fractal with polychromatic, i.e. multi-wavelength light, a distribution of hot spots is generated in the fractal with a different distribution generated for each wavelength. However, if the radiation at a given wavelength has an intensity greater than some threshold value, the so-called photomodification threshold, then the distribution of hot spots in the fractal medium associated with that wavelength becomes "photomodified." This means that a particular distribution of nanoparticles comprising the fractal medium is physically altered. The consequences of this photomodification for the optical emission is that the absorption of the fractal medium is altered. Moreover, this alteration in absorption is permanent, and a so-called "spectral hole" is burned into the fractal medium at this wavelength. This hole burning effect has use as an optical memory device. The fractal medium "remembers" that a particular wavelength physically altered its fractal structure and not some other wavelength. Because of the sub-wavelength dimension of the hot spots and because of the fact that different wavelengths burn holes in spatially distinct regions of the fractal, the density of information stored in the fractal medium is large, enabling high capacity optical data storage.

EXAMPLE 4

Near-Field Optical Spectroscopy

Near-field optics is an optical measurement method which can achieve spatial resolution much higher than the conventional optical microscopy. The spatial resolution for a conventional optical microscope is limited to approximately one half of the light wavelength, which is several hundred nanometers in the visible spectrum. Near-field optics can achieve 1 nanometer spatial resolution.

There are several successful methods to achieve the superior spatial resolution in near-field optics. M. A. Paesler and P. J. Moyer, *Near-Field Optics: Theory, Instrumentation, and Applications* (Wiley, N.Y., 1996). One method locates the material within a distance shorter than the light wavelength from a tapered end of an optical fiber and detects the light emitted from the material through the optical fiber. Another method uses a tapered end of an optical fiber, located within a distance shorter than the light wavelength from the material, to illuminate the material. Yet another method locates a sharp tip of a vibrating metal wire within a distance shorter than the light wavelength from the material and the light emitted from the material is detected employing a lock-in method. In all of these methodologies, the material to be detected must be located within a distance shorter than the light wavelength from either a tapered end of an optical fiber or a sharp tip of a vibrating metal wire.

Near-field optical spectroscopy is a near-field optical spectroscopic method, which detects chemical compounds and biological materials through their spectroscopic signatures. The material can be any of the following: a single molecule, a plurality of molecules, a nanocrystal, DNA, DNA fragments, amino acids, antigen, antibodies, bacteria, bacterial spores, or viruses. The spectroscopic signatures obtained can be either electronic, vibrational, or rotational spectroscopic signatures, which are often available through published literature. Several types of optical processes can be involved in the near-field optical spectroscopic method including photoluminescence, Raman scattering, hyper-Raman scattering, Brouillon scattering, harmonic generation, sum frequency generation, difference frequency generation, and optical Kerr effect.

Figure 10:
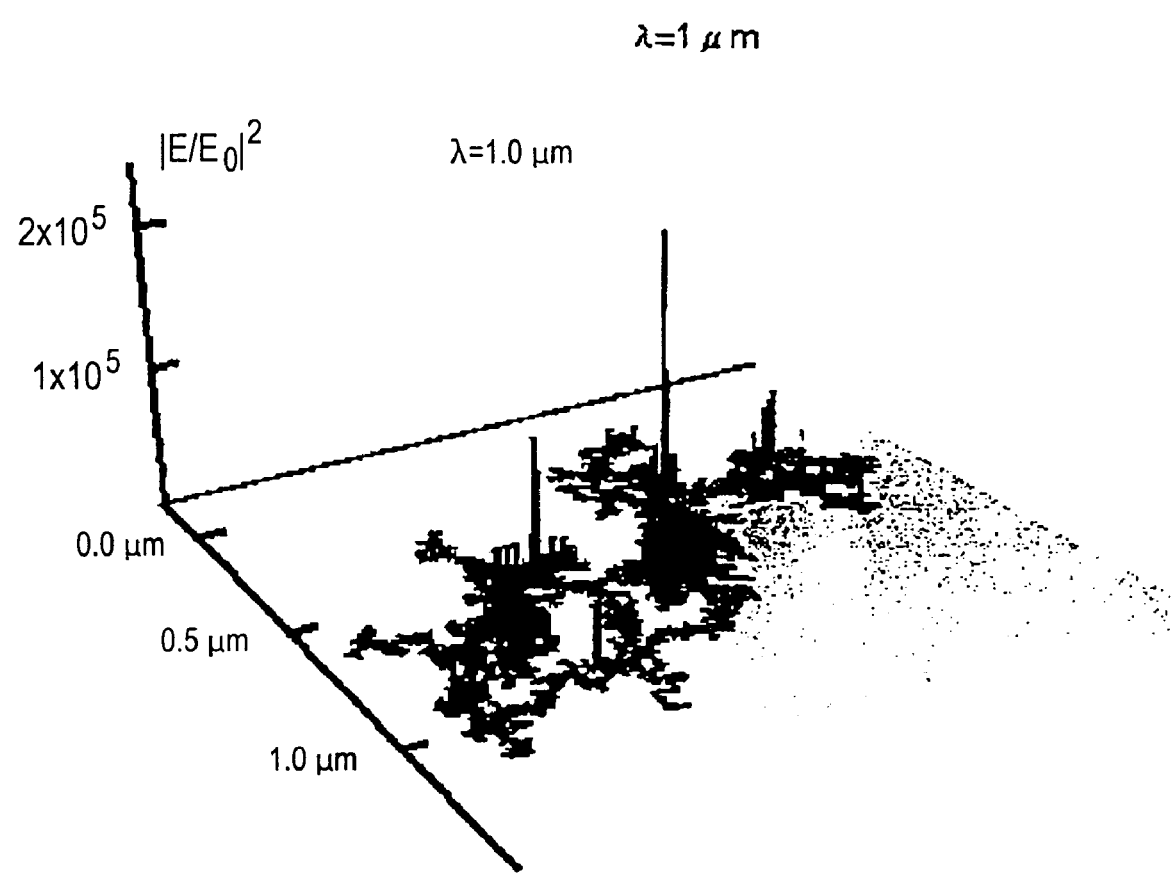
FIG. 10 shows theoretical prediction for enhancement, by factors of up to 100,000, of linear optical intensity for a fractal of silver nanoparticles.
Figure 11A:
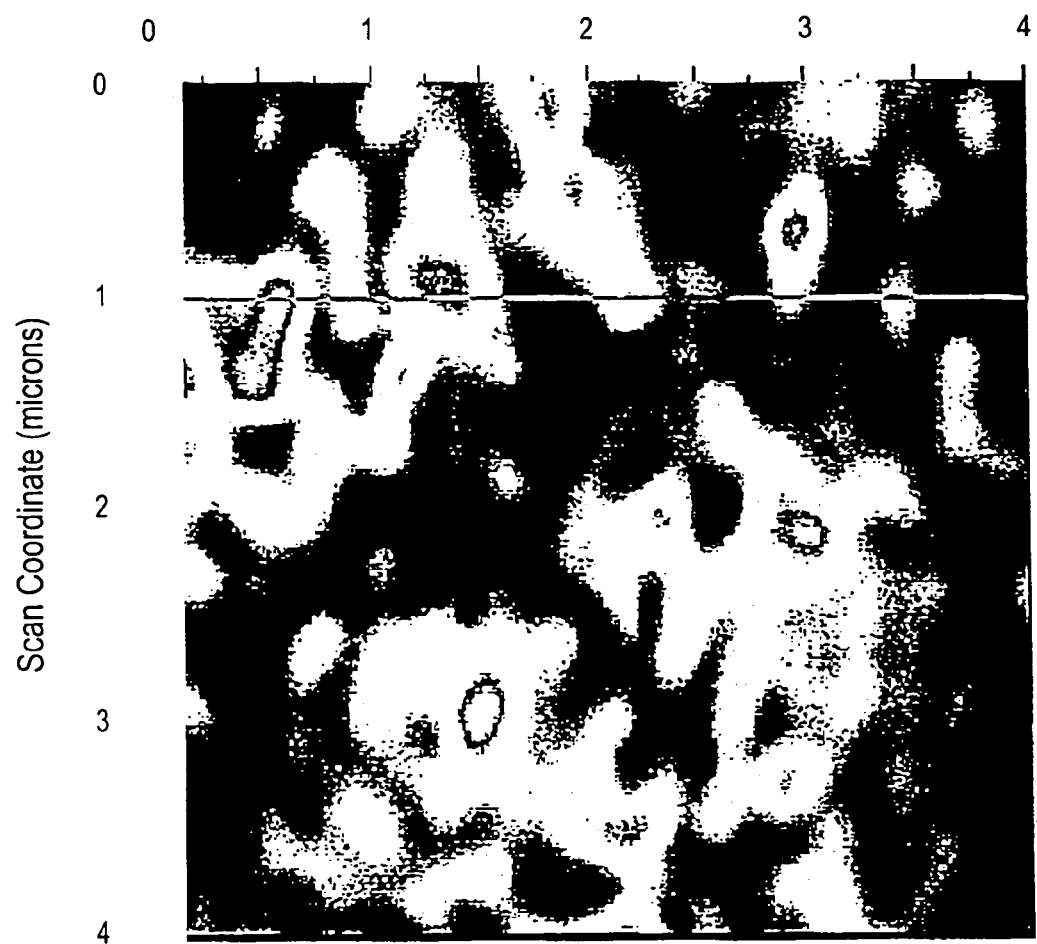
FIGS. 11a–b show experimental data of linear optical intensity for fractals of silver nanoparticles, collected through an optical fiber, the tapped end of which was located within the light wavelength from the fractals.
Figure 11B:
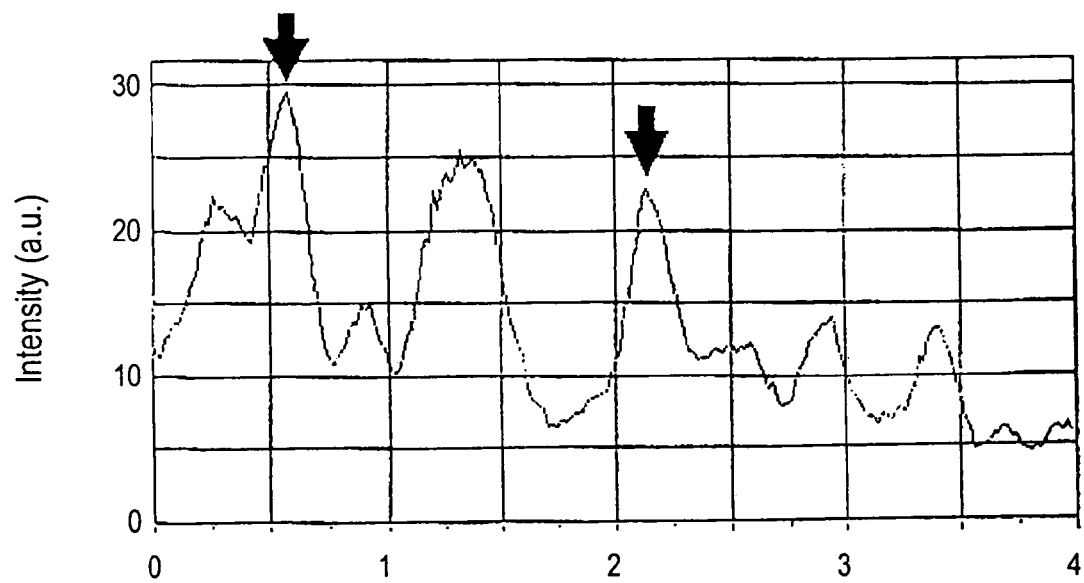

Near-field optical signals can be enhanced by non-aggregated nanoparticles as well as by aggregated nanoparticles (fractals). FIG. 10 shows a theoretical prediction for the enhancement (by factors of up to $10^5$ or 100,000) of linear optical intensity for a fractal of silver nanoparticles. FIG. 11 shows experimental data of linear optical intensity for fractals of silver nanoparticles. The data shown in FIG. 11 were collected through an optical fiber, whose tapped end was located within the light wavelength from the fractals.

Non-aggregated nanoparticles and aggregated nanoparticles, the medium, can enhance near-field optical spectroscopy of a material, when the material is doped onto the medium. In the case where the light signal is detected through the optical fiber, there is an alternative wherein the medium is deposited onto the input end of the optical fiber instead.

Furthermore, a microcavity can enhance near-field optical spectroscopy of a material, where located in the vicinity of the microcavity. A combination of the medium and a microcavity can also enhance near-field optical spectroscopy of a material, where located in the vicinity of the microcavity. The material is doped onto the medium, or, in the case where the light signal is detected through the optical fiber, the medium is deposited onto the input end of the optical fiber.

EXAMPLE 5

Optical Amplifiers

Fractals, microcavities, and fractal/microcavity composites can be utilized for optical amplification. Physical processes that optically amplify include but are not limited to, stimulated emission, optical parametric processes, stimulated Raman processes, stimulated Brilluoin processes, and phase conjugation processes. The utilization of the aforementioned processes for optical amplification are discussed in standard texts.

Optical amplifiers that utilize nonlinear optical processes require an optical pump source and a source of signal photons to be amplified. In conventional nonlinear optical amplifiers one of the following is required for efficient operation: very high pump intensity, very long interaction length, a high quality factor resonator or a combination of those three features.

For example, Yariv in "Quantum Electronics" $3^{rd}$ Ed. pp. 466–467 calculates a stimulated Raman gain coefficient, $g_R = 2 \times 10^{-8} I_p$ cm$^{-1}$, where $I_p$ represents the pump intensity in watt/cm$^2$, this requires a pump intensity of 1 MW/cm$^2$ to achieve a gain coefficient of a mere 2% per cm. In fiber Raman amplifiers the pump powers are kept at the level of a few watts while the interaction length is spread out over tens of kilometers to achieve an amplifier gain of 1000, (see "Analysis of counter-pumped small-signal fibre Raman amplifiers," by S. R. Chinn, Electronics Letters, Vol. 33, No. 7, pp. 607–608, Mar. 27, 1997). Conventional high quality factor resonators are typically expensive and it is also difficult to couple light into these resonators efficiently.

The fractal, microcavity, and fractal/microcavity systems described herein have the advantages of reducing the required pump power or interaction length by five or more orders of magnitude. For example, a simple 100-micron long single pass fractal/sodium citrate single pass amplifier has generated a gain of 1000 when pumped with a 10 mW source. The Raman small signal gain coefficient for this fractal/sodium citrate amplifier was measured, $g_R = 0.5 I_p$ cm$^{-1}$, and this is clearly over seven orders of magnitude greater than the gain coefficient calculated by Yariv above, thus the low pump power (10 mW) and short interaction length (100 microns) compared to conventional systems. Lastly, the fractal, microcavity, and fractal/microcavity systems eliminate the need for complicated high quality factor cavities.

The advantages described above of the fractal stimulated Raman amplifier are discussed in comparison to the conventional stimulated Raman amplifier. While reference is made explicitly to the stimulated Raman amplifier, comparable results are achieved for the microcavity stimulated Raman amplifier and amplifiers that utilize other nonlinear optical gain proceses. Furthermore, larger enhancements are expected when a fractal/microcavity system is utilized for amplification over any of the other amplification processes mentioned above.

EXAMPLE 6

Wavelength Translation Devices

Fractals, microcavities, and fractal/microcavities can be utilized for optical wavelength translation devices. The wavelength translation occurs via one of the following processes: stimulated Raman and stimulated hyper-Raman scattering, Stimulated Brouillon scattering, harmonic generation, optical parametric processes, multi-photon emission, four-wave mixing and/or phase conjugation. The utilization of several of the aforementioned processes for optical frequency translation are discussed in standard texts.

Optical wavelength translation devices that utilize nonlinear optical processes require one or more optical wavelength beams be sent into the nonlinear device. For example optical harmonic generation only requires that a single beam enter and several harmonic frequencies may exit along with part of the original pump wavelength, while in a four-wave mixing device up to three pump wavelengths may be sent into the nonlinear medium and one signal wavelength exit. In conventional nonlinear optical wavelength translation devices one of the following is required for efficient operation: very high pump intensity, very long interaction length, a high quality factor resonator or a combination of the three features. Just as was the case for the optical amplification one or more of the following advantages will occur, the optical threshold will be reduced by five or more orders of magnitude, the device size may be decreased by five or more orders of magnitude, and the conversion efficiency will be significantly increased. These results apply for all of the wavelength translation processes. The advantages of the fractal, microcavity, and fractal/microcavity for wavelength translation devices based upon the Raman and hyper-Raman emissions are discussed in detail earlier in the sections entitled "Surface-Enhanced Raman Scattering in Sodium Citrate" and "Hyper-Raman Scattering of Sodium Citrate Molecules Attached to Colloid Particles and Their Fractal Aggregates".

While particular optical processes are described above, additional optical processes can be provided when exciting the medium of the present invention and include: photoluminescence, Raman scattering, hyper-Raman scattering, Brouillon scattering, harmonic generation, sum frequency generation, difference frequency generation, optical parametric processes, multi-photon absorption, optical Kerr effect, four-wave mixing, and phase conjugation.

The preceding examples can be repeated with similar success by substituting the generically or specifically described reactants and/or operating conditions of this invention for those used in the preceding examples.

Semicontinuous Metal Films

The present invention is also of a method of fabricating semicontinuous metal films and of applications and optical methods for structures comprising semicontinuous metal films.

Semicontinuous metal films are preferably produced by depositing metal atoms and/or ions onto insulator or semiconductor substrate, especially those types of substrate where the metal does not "wet." In the preferred deposition process, small and isolated metal islands are formed first. As the metal coverage increases, the islands coalesce, forming irregularly shaped clusters in random geometry on the substrate. The cluster size increases as the film grows further and diverges as the film approaches the percolation threshold, where an insulator-to-metal transition occurs. A metal film at or near its percolation threshold is semicontinuous. A quasi-continuous film, with voids of irregular shapes, is formed at a metal coverage substantially higher than the percolation threshold.

Metal deposition can be realized using physical or chemical methods. The former comprises thermal evaporation, pulsed laser deposition, electron-beam deposition, ion-beam deposition, sputtering, radio-frequency glow discharge, and lithography. The lithography may use uv light, x-ray, an electron beam, or an ion beam. An example of chemical methods is ion exchange. The average metal coverage can be measured using a quartz film-thickness measurement device. The percolation threshold can be determined accurately and reproducibly using electric and/or optical methods. At the percolation threshold, the DC electric conductivity increases sharply and light transmittance, absorption and reflection exhibit anomalous behavior. A. K. Sarychev and V. M. Shalaev, *Physics Reports* 335, p. 275 (September 2000). Morphology of semicontinuous metal films can be characterized using electron microscopy and/or atomic force microscopy.

Depending on (a) choice of metal, (b) choice of dielectric or semiconductor substrate, and (c) growth conditions, the average thickness of the film may vary from 0.1 to 100 nm while the average width of the metal cluster branches in the surface plane may vary from 1 to 1000 nm, and the lengths of the metal cluster branches in the surface plane vary widely from the lateral width of the metal cluster branches to the size of the whole film. A typical value for film thickness is 5 to 10 nm; and a typical lateral width of metal particles is somewhat larger (10 to 50 nm). The space between the metal clusters can be filled with a dielectric or semiconductor material, or left unfilled. Filling the space between the metal clusters with a dielectric or semiconductor material leads to a smoother top surface of the film. Covering the whole film with a thin layer of a dielectric, semiconductor, or organic material smoothens the film's top surface and protects the metal from chemical reactions and degradation.

Figure 16:
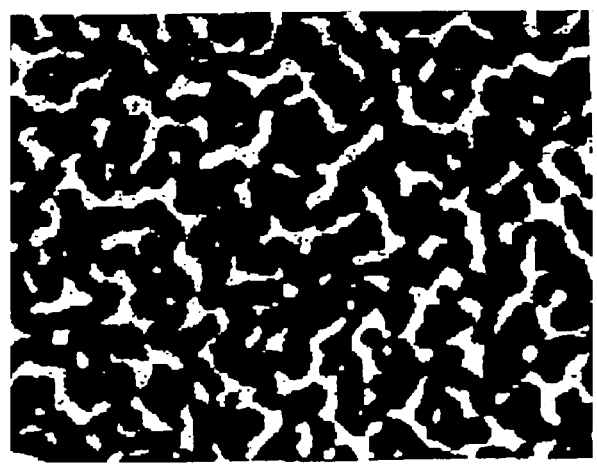
FIG. 16 is an electron microscopy image (400×500 nm) of a semicontinuous metal film near percolation.

FIG. 16 shows an electron microscopy image (top view) of a semicontinuous metal film fabricated using a pulsed laser deposition (PLD) technique. In the fabrication process, a silver target was placed in a vacuum chamber back-filled with argon, which acted as a buffer gas. A nanosecond Nd:YAG laser was used as the light source. Silver atoms, ions and small clusters ejected from the silver target surface by laser irradiation were deposited onto a glass or other substrate placed near the silver target. The dark features in the image above represent clusters of metal (silver in this case). The white areas are voids. This particular film appears very close to the percolation threshold.

Figure 17:
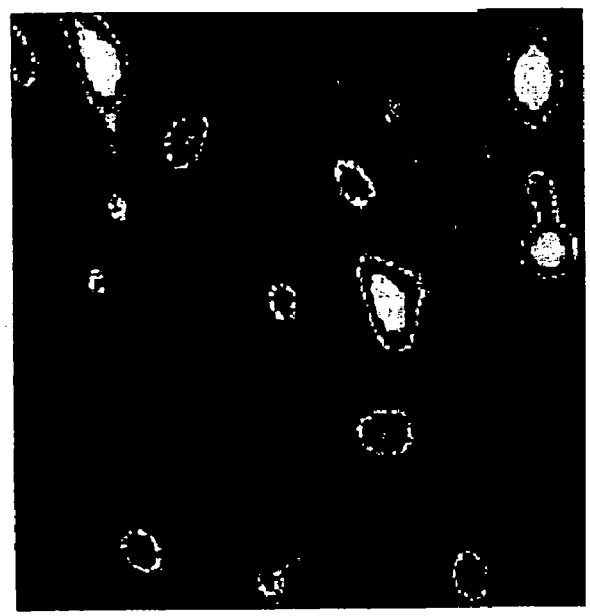
FIG. 17 is a near-field optical image (5×5 μm) of a semicontinuous metal film near the percolation threshold; the white areas have much greater local light intensity than the dark areas.

The local field at a semicontinuous metal film can be detected employing near-field optical method (M. A. Paesler and P. Moyer, *Near-Field Optics: Theory, Instrumentation, and Applications* (Wiley, N.Y., 1996)). The near-field optical instrument may use tapped optical fiber (straight or bent), sharpened metal wire, solid immersion lens and other technologies. FIG. 17 shows a near-field optical image of a semicontinuous silver metal film near the percolation threshold. The white areas have much greater local light intensity than the dark areas.

While both semicontinuous metal films and fractal aggregates of metal nanoparticles provide enhancement of local optical fields, they have different geometries and different properties. Semicontinuous metal films have several technical advantages over fractal aggregates of metal nanoparticles, especially those made in a chemical way. (a) Semicontinuous metal films are made under vacuum with well-controlled environment and parameters, leading to better quality control. (b) The real-time and in-situ determination of percolation threshold can be achieved accurately and reproducibly using electric and/or optical methods. (c) The structure of a semicontinuous metal film, being a network of highly interconnected metal clusters, is more robust than a fractal aggregate of metal nanoparticles, being a collection of loosely linked nanoparticles. (d) A semicontinuous metal film near the percolation threshold has, on average, a higher density and a more uniform distribution of hot spots than a fractal aggregate of metal nanoparticles. This result is associated with the fact that a semicontinuous metal film has roughly equal metal and insulator areas of uniform distribution on average, while a fractal aggregate has a number of voids of large and small areas. (e) Deposition of a semicontinuous metal film onto the surface of any substrate or a device is straightforward, simply by placing the substrate or device in a deposition chamber.

Combining the energy-concentrating effect in semicontinuous metal films with other means for producing strong resonances can result in truly gargantuan local fields. For example, morphology-dependent resonances (MDRs) in dielectric or semiconductor microcavities (or microresonators) produce large intensity enhancements in the resonances that can lead to lasing. R. K. Chang and A. J. Campillo, eds, *Optical Processes in Microcavities* (World Scientific, Singapore, 1996). These resonances have extremely high quality factors ($Q=10^5$ to $10^{10}$) that result from confinement of the radiation within the microcavities by multiple total internal reflections. Light emitted or scattered from a source at the microcavity may couple to the high-Q MDRs in its spectral bandwidth, leading to enhancement of the spontaneous and/or stimulated optical emissions. Hence, coating microresonators with semicontinuous metal films will further increase, multiplicatively, the local fields leading to enhancement of optical and other photoinduced processes.

Figure 18:
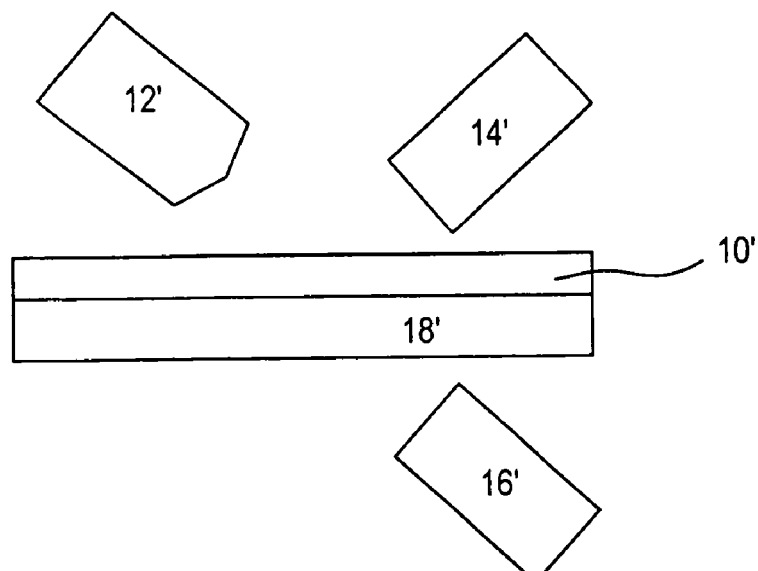
FIG. 18 is a schematic representation of an optical sensor employing a semicontinuous metal film (one or more detectors may be used).

For example, FIG. 18 shows an optical sensor according to the invention which employs a semicontinuous metal film. The sensor preferably comprises a medium 10' comprising a semicontinuous metal film of randomly distributed metal particles and their clusters, a light source 12', one or more detectors 14' located at the same side of the medium as the light source, and an additional layer 18' for structural support and other purposes. The sensor optionally comprises one or more detectors 16' located at the opposite side of the medium from the light source.

Microcavities are optical resonators, with many possible shapes and dimensions. Examples of microcavity shapes include sphere, ellipsoid, polyhedron, and cylinders of various cross sectional geometry such as circle, ellipse, bow-tie and polygon. R. K. Chang, et al., eds., *Optical Processes in Microcavities* (World Scientific, Singapore, 1996); E. Gornik, *Science* 280, p. 1544 (1998). Microcavities can be either solid (e.g., a solid sphere) or hollow (e.g., a cylindrical tube). A solid spherical microcavity or a cylinder of circular cross section has quite uniform distribution of electric field. A cylinder of deformed circular or bow-tie cross section allows light emission in narrow angles. Optical fiber can be treated as a microcavity of cylindrical shape of circular cross section.

The three dimensions of a microcavity need not be the same. Usually at least one of the three dimensions of a microcavity is equal or greater than one half of the light wavelength of interest and at least one of the three dimensions is smaller than 1000 times of the light wavelength.

Semicontinuous metal films can be deposited onto the outer surface of a microcavity simply by placing the microcavity in a deposition chamber.

The present invention also has applications in conjunction with chiral molecules. A number of molecules, especially organic molecules and biomolecules, are chiral. Chiral molecules have two enantiomers (also named stereoisomers) with different handedness. The molecules that produce clockwise rotation of linearly polarized light are called positive (+) or dextrorotatory (d), while the molecules that produce counter clockwise rotation of linearly polarized light are called negative (−) or levorotatory (l). An alternative notation system for chiral molecules is based on geometric arrangement of the substituents of a chiral molecule. A chiral molecule is in the rectus (R) configuration if, with the lowest-ranked substituent pointing away, the order of decreasing precedence of the three highest-ranked substituents is clockwise. Otherwise, it is in the sinister (S) configuration.

A classical example of chiral organic molecules is bromochlorofluoromethane (BrClFCH). In the biological systems on the Earth, the d enantiomer of sugars and the l enantiomer of amino acids dominate.

While the usual physical properties such as mass, density, melting temperature are identical for both enantiomers of a chiral material, enantiomers can have striking differences in their properties that depend on the arrangement of the atoms in space. Two enantiomers cause rotation of linearly polarized light in different directions. Biologically, (l)-nicotine, for example, is much more toxic than (d)-nicotine, and (l)-adrenaline is less active in the construction of blood vessels than (d)-adrenaline. (l)-Thyroxine is an amino acid of the thyroid gland, which speeds up metabolism and causes nervousness and loss of weight, while (d)-thyroxine exhibits none of these effects but is used to lower cholesterol level of patients.

There are over 500 chiral substances that are produced synthetically and used as prescription and over-the-counter drugs. Most of them are synthesized and administered as racemic mixtures even thought the desired therapeutic activity resides usually in one of the enantiomers. For example, the S enantiomer is responsible for the pain relief of ibuprofen, which is normally sold as a racemic mixture. Several antihistamine drugs, including Allegra®, Claritin® and Zyrtec®, have one of the enantiomers providing the desired therapeutic benefits of allergy treatment while the other causes side effects. When the racemic mixture of thalidomide was used in Europe four decades ago as a sedative and antinausea drug, due to (R)-thalidomide, the S enantiomer in the drug led to many cases of serious birth defects in children born to women who took the drug while pregnant.

The local fields in the hot spots exhibit optical activities; the locations of hot spots for a given semicontinuous metal film, when irradiated by light of different helicities (i.e., right- and left-elliptically or circularly polarized light), are usually different. The effect occurs because resonant plasmon modes in semicontinuous metal films, which have neither center nor plane of symmetry, have handedness in spatial distribution of their amplitudes. In contrast to chiral molecules, where the chiral substituents are usually much smaller than the light wavelength, the local chiral structures supporting localized plasmon oscillations in semicontinuous metal films can be comparable in size with the wavelength, so that the optical activity in these films can be much greater than in chiral molecules.

The chirality of the local field at a semicontinuous metal film can be detected employing near-field optical method (M. A. Paesler and P. Moyer, *Near-Field Optics: Theory, Instrumentation, and Applications* (Wiley, N.Y., 1996)) with the film irradiated by light of different helicities. The near-field optical instrument may use tapped optical fiber (straight or bent), sharpened metal wire, solid immersion lens and other technologies.

Optical activity can be used to distinguish the enantiomers from each other, which is very important because the chemical, biological and therapeutic effects of the enantiomers are often very different. Different enantiomers respond to a hot spot of a given handedness differently. Use of semicontinuous metal films as media for optical activity measurements can achieve much higher sensitivity while at the same time using a much smaller quantity of sample than the traditional techniques. The semicontinuous metal films serve as amplifiers that enhance optical signal. It is believed that measurements can be performed at the single molecular level.

All current techniques of optical detections of chiral materials can be combined with semicontinuous metal films, which provide signal enhancement. These comprise of polarimetry, circular dichroism (both electronic circular dichroism and vibrational circular dichroism) and nonlinear optical circular dichroism (e.g., second harmonic generation circular dichroism).

The present invention thus offers a super-sensitive probe of chiral purity without using an enantiomer separation procedure (e.g., chiral chromatography). Such a probe will be beneficial in development, synthesis, and manufacture of chiral molecules of enantiomeric purity.

Industrial Applicability:

The invention is further illustrated by the following non-limiting examples.

EXAMPLE 7

Super-Sensitive Optical Spectroscopy and Detection

Semicontinuous metal films or semicontinuous-metal-film/microcavity composites can be used for super-sensitive optical spectroscopy. Both linear and nonlinear optical processes are possible. Examples of linear optical processes include fluorescence, Raman scattering, Brillouin scattering. Examples of nonlinear optical processes include stimulated Raman scattering, hyper-Raman scattering, multi-photon anti-Stokes emission, harmonic generation, sum-frequency generation, difference-frequency generation, optical parametric processes, multi-photon absorption, three- and four-wave mixing, and phase conjugation. R. W. Boyd, *Nonlinear Optics* (Harcourt Brace, 1992). It is interesting to note that, in contrast to conventional situations, where fluorescence is typically quenched, the local-field enhancement on the semicontinuous metal films or semicontinuous-metal-film/microcavity composites is so large that the rate of the radiative channel is greater than a non-radiative energy transformation. Accordingly, fluorescence and other optical processes are not quenched but rather dramatically enhanced.

The highly enhanced linear and nonlinear optical processes allow super-sensitive optical spectroscopy of a large number of objects, which may include atoms, molecules, nanocrystals, nanoparticles, and biological materials. These include but are not limited to detection and spectroscopical analysis of contaminations and environment hazards in the air, in water, in soil, at or near manufacturing sites, or at waste dumps; explosives; controlled substances; residual chemicals in foods; chemical and biological agents (including but not limiting to metal ions, proteins, DNA, DNA fragments, antigens, antibodies, bacteria and viruses) in the body, various body fluids and wastes of human and animals. An object to be examined should be placed in contact with or in a close proximity of a semicontinuous metal film or semicontinuous-metal-film/microcavity composite. The giant enhancement offered by a semicontinuous metal film alone or by a combination of a semicontinuous-metal-film/microcavity composite makes possible of detection of chemical, biological and physical materials in a very minute quantity, possibly down to single molecular level.

The optical spectroscopy employs far-field and/or near-field optical methods. R. W. Boyd, *Nonlinear Optics* (Harcourt Brace, 1992); M. A. Paesler, et al., *Near-Field Optics: Theory, Instrumentation, and Applications* (Wiley, N.Y., 1996). The near-field instrument may use tapped optical fiber (straight or bent), sharpened metal wire, solid immersion lens and other technologies.

While the term of optical spectroscopy implies of optical measurements at multiple light wavelengths, detection of chemical, biological and physical materials can often be made using a single incident light wavelength. Therefore, semicontinuous metal films or semicontinuous-metal-film/microcavity composites can be used for super-sensitive optical detections of a large number of objects mentioned above, utilizing both linear and nonlinear optical processes and employing far-field and/or near-field optical methods. The ability of super-sensitive detection of minute-quantity materials is very important for areas such as chemical studies, environmental monitoring, DNA analysis, and express medical diagnostics.

Employing semicontinuous metal films and near-field optical methods, optical spectroscopy can be achieved using neither a grating nor a prism. The heart of an optical spectrometer used today is a grating, which consists of a large number of parallel and periodic grooves, or a prism made of a transparent material. The grating or prism disperses light of different wavelengths into different directions. A semicontinuous metal film directs light of different wavelengths into different locations of hot spots. Since the hot-spot locations of a given semicontinuous metal film at various light wavelengths and/or polarizations are predetermined, the film can be used to perform optical spectroscopy of unknown light sources. The recording can be achieved employing a near-field optical method of either scanning or imaging using a solid immersion lens. Such a gratingless spectrometer can be used for chemical studies, environmental monitoring, DNA analysis, and express medical diagnostics.

Figure 19:
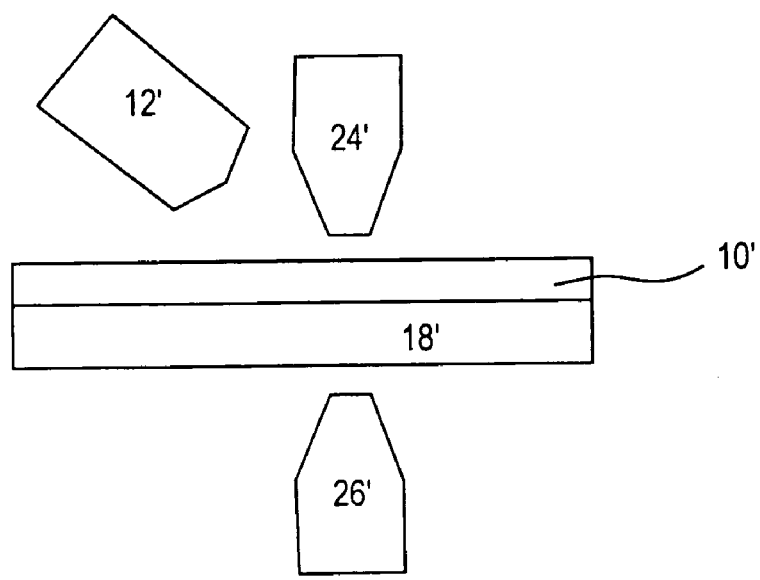
FIG. 19 is a schematic representation of a gratingless spectrometer employing a semicontinuous metal film (one or more near-field detectors may be used).

FIG. 19 illustrates a gratingless spectrometer employing a semicontinuous metal film according to the invention. The spectrometer preferably comprises a medium 10' comprising a semicontinuous metal film of randomly distributed metal particles and their clusters, a light source 12', an additional layer 18' for structural support and other purposes, and one or more near-field detectors 24' located on the same side of the medium as the light source. The spectrometer optionally comprises one or more near-field detectors 26' located on the opposite side of the medium from the light source.

EXAMPLE 8

Coding and Decoding Information

A semicontinuous metal film can be also used as a device for writing and reading security codes and for cryptography. In this case, a match of a particular light source of single or multiple wavelengths at a particular polarization configuration and a particular pattern for a given semicontinuous metal film is required for the coding and positive identification. This is possible because a light with a given wavelength and polarization for any particular semicontinuous metal film induces unique field distribution, which practically cannot be reproduced with a different film and/or different light characteristics. This unique property can be used for secure coding, for example, in bank operations and in sending and processing secret information.

The advantages of optical detection using semicontinuous metal films or semicontinuous-metal-film/microcavity composites include super sensitivity, unique local field distribution, lower pumping power, smaller sizes, and lower weights than other designs.

Figure 20:
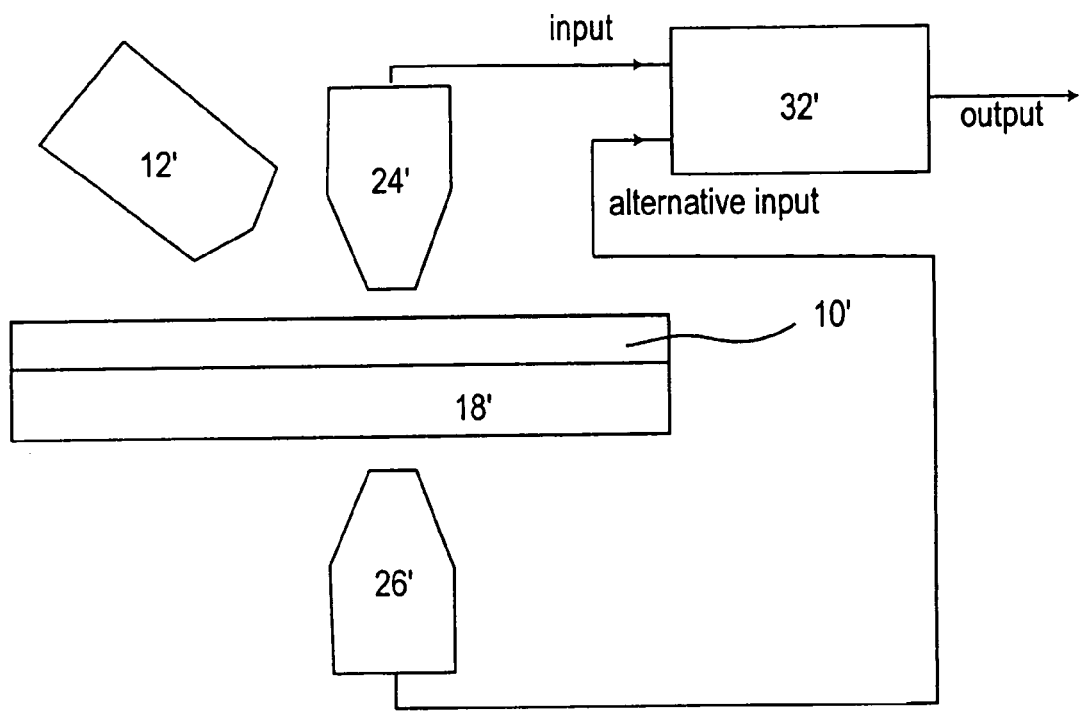
FIG. 20 is a schematic representation of a device for cryptography, coding and decoding information employing a semicontinuous metal film (one or more near-field detectors may be used).

FIG. 20 illustrates a device for cryptography, coding, and decoding information employing a semicontinuous metal film according to the invention. The device preferably comprises a medium 10' comprising a semicontinuous metal film of randomly distributed metal particles and their clusters; a light source 12', one or more near-field detectors 24' located on the same side of the medium as the light source, and a computerized logic component 32' that compares a detected light pattern with an expected pattern. The device optionally comprises one or more near-field detectors 26' on the opposite side of the medium from the light source.

EXAMPLE 9

Optical Limiting

Semicontinuous metal films can be used as media for optical limiting, which dramatically decreases light transmittance above a threshold of incident light intensity. There are a number of optical-limiting materials (e.g., molecules with reverse saturable absorption). R. Crane, et al., eds., *Materials for Optical Limiting* (Materials Research Society, Pittsburgh, 1995); P. Hood, et al., eds., *Materials for Optical Limiting II* (Materials Research Society, Pittsburgh, 1995). A mixture of semicontinuous metal film with traditional optical-limiting materials can dramatically increase sensitivity of such an optical limiter and decrease the operational threshold level.

Figure 21:
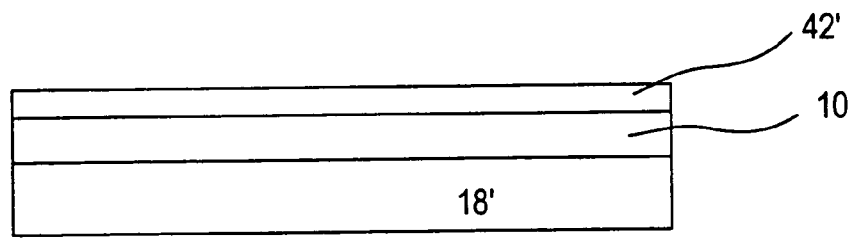
FIG. 21 is a schematic representation of an enhanced optical limiting device employing a semicontinuous metal film.

FIG. 21 illustrates an enhanced optical limiting device employing a semicontinuous metal film according to the invention. The device preferably comprises a medium 10' comprising a semicontinuous metal film of randomly distributed particles and their clusters, an additional layer 18' for structural support and other purposes, and a layer of optical limiting materials 42'.

EXAMPLE 10

Microlasers

Semicontinuous metal films or semicontinuous-metal-film/microcavity composites can be used for microlasers. In order to achieve directional emission, a microcavity of a cylinder of deformed circular or bow-tie cross section allows laser emission in narrow angles. Another possibility is incorporation of semicontinuous metal films into semiconductor lasers, including the traditional semiconductor lasers and the recently developing Vertical Cavity Surface Emitting Lasers (VCSELs) in order to shift laser output wavelength and achieve laser output at multiple wavelengths. The advantages of microlasers with semicontinuous metal films or semicontinuous-metal-film/microcavity composites, which provide field enhancement, include lower pumping power, smaller sizes, and lower weights than other designs. Another important property of semicontinuous metal films that is important for their use for developing novel microlasers is their very broad amplification band, from the near ultra-violet to the far infrared.

Figures 22A, 22B:
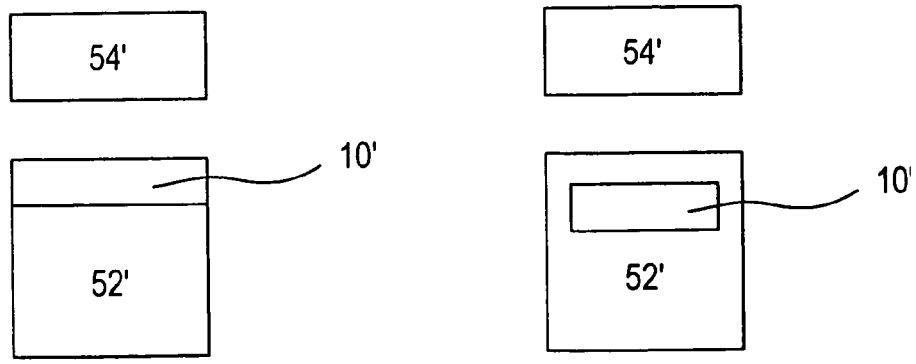
FIG. 22 is a schematic representation of a microlaser employing a semicontinuous metal film; the film can be either (A) located at the surface of a microcavity or (B) integrated together with the microcavity; there is an optically active material (not shown), which could stand alone or be integrated together with either the semicontinuous metal film or microcavity; the energy source may be either optical or electrical.

FIG. 22 illustrates a microlaser employing a semicontinuous metal film according to the invention. The microlaser preferably comprises a medium 10' comprising a semicontinuous metal film of randomly distributed metal particles and their clusters, an energy source 54', and a microcavity/microresonator 52'. The film can be either (A) located at the surface of the microcavity or (B) integrated together with the microcavity. There is also an active medium (not shown), which could stand alone, or integrated together with either the semicontinuous metal film or microcavity. The energy source can be either optical or electrical.

EXAMPLE 11

Optical Amplifiers and Switches

Semicontinuous metal films or semicontinuous-metal-film/microcavity composites can be used for super-sensitive optical amplification and switching, which utilize one or more of linear and nonlinear optical processes as mentioned above. Raman scattering, stimulated Raman scattering, and hyper Raman scattering are particularly suitable for optical amplification. The optical Kerr effect, with Femtosecond response time, is ideal for optical switching. The advantages of optical amplifiers and switches with semicontinuous metal films or semicontinuous-metal-film/microcavity composites include lower pumping power, smaller sizes, and lower weights than other designs.

Figure 23A:
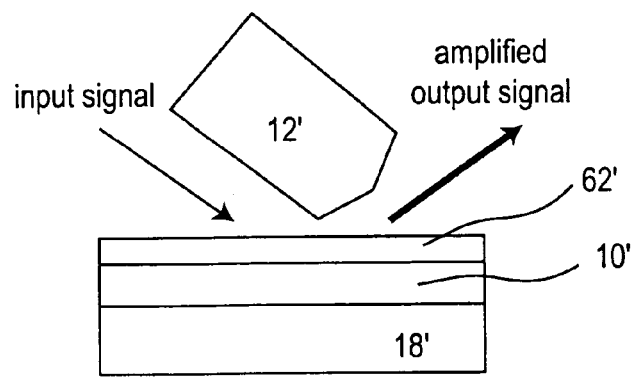
FIG. 23 is a schematic representation of an optical amplifier employing a semicontinuous metal film; the amplifier (A) may or (B) may not have an additional coating layer of optical materials such as Raman materials; the output is preferably amplified.
Figure 23B:
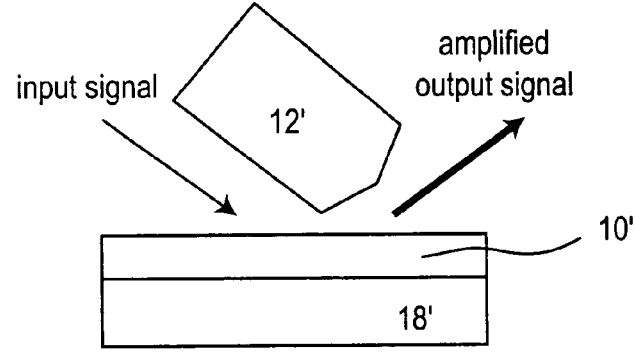

FIG. 23 illustrates an optical amplifier employing a semicontinuous metal film according to the invention. The optical amplifier preferably comprises a medium 10' comprising a semicontinuous metal film of randomly distributed metal particles and their clusters, a light source 12', an additional layer 18' for structural support and other purposes, and a layer of optical materials 62' such as Raman materials. The amplifier (A) may or (B) may not have an additional coating layer of optical materials such as Raman materials. The output is preferably amplified in comparison to the input.

Figure 24A:
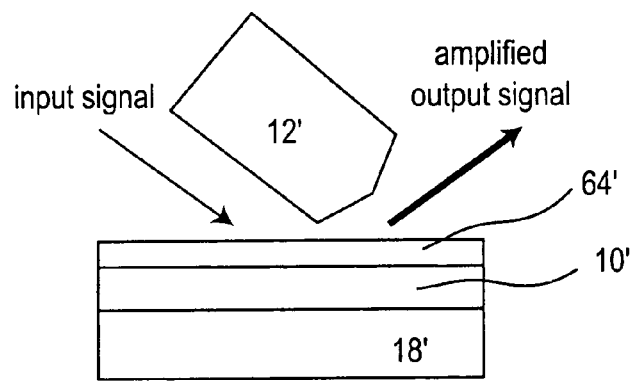
FIG. 24 is a schematic representation of an optical switch employing a semicontinuous metal film; the switch (A) may or (B) may not have an additional coating layer of optical materials such as Kerr materials; the input and output are at different wavelengths.
Figure 24B:
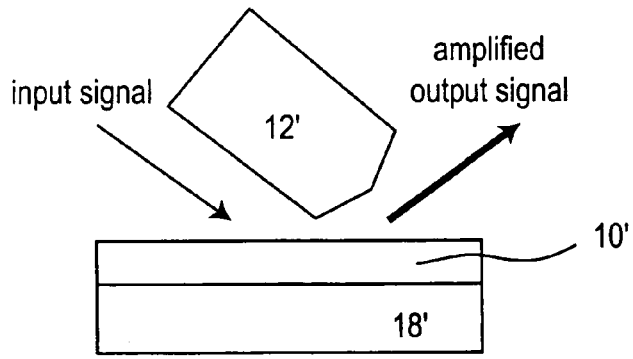

FIG. 24 illustrates an optical switch employing a semicontinuous metal film according to the invention. The optical switch preferably comprises a medium 10' comprising a semicontinuous metal film of randomly distributed metal particles and their clusters, a light source 12', an additional layer 18' for structural support and other purposes, and a layer of optical materials 64' such as Kerr materials. The amplifier (A) may or (B) may not have an additional coating layer of optical materials such as Kerr materials. The input and output are preferably at different wavelengths.

EXAMPLE 12

Super-density Optical Recording

Semicontinuous metal films can be used as a medium for super-dense optical recording of information. The size of a hot spot is on the order of 10 nm. By varying the light wavelength and polarization of the incident beam one can excite any given spot of the size 10×10 $nm^2$. Adding one or more thin layers of a photosensitive material allowing optical recording of information, one can reach information density as large as $10^{12}$ $bit/cm^2$, which is 1200 times greater than the density of DVD-9, single-sided double-layer DVD that holds 8.5 GB information.

Locations of hot spots at a semicontinuous metal film depend on light wavelength, polarization, and even angle of incidence. Use of multiple light wavelength, polarization, and/or angle of incidence allows several bits of information in the same area, effectively achieving multi-layer information storage.

All photosensitive materials that are currently in use or in investigation can be used together with semicontinuous metal films for super-dense optical recording. Examples of photosensitive materials include magneto-optic layers (e.g., TbFeCo), solid films exhibiting crystal-amorphous phase transitions (e.g., GeSbTe), dye molecules, and molecules with long life-time triplet states (e.g., polymers allowing the trans-cis photoisomerization). The semicontinuous metal layer increases the signal-noise ratio through hot spots, provides a natural patterning of the recording surface of ~10 nm in dimensions, and allows storage of multiple bits of information in the same area.

Data reading and writing will employ near-field optical method. M. A. Paesler, et al., *Near-Field Optics: Theory, Instrumentation, and Applications* (Wiley, N.Y., 1996. The instrument may use tapped optical fiber (straight or bent), sharpened metal wire, solid immersion lens and other technologies.

Figure 25:
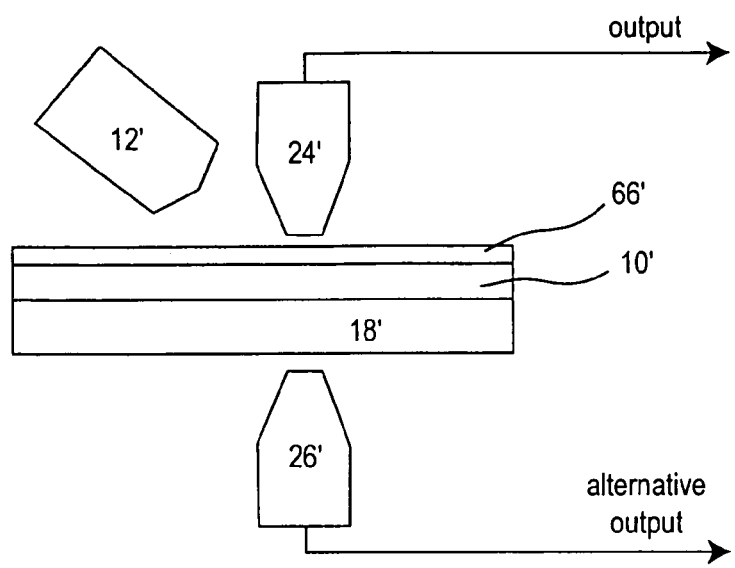
FIG. 25 is a schematic representation of a super-density optical recording device employing a semicontinuous metal film (one or more near-field detectors may be used).

FIG. 25 illustrates a super-density optical recording device according to the invention using a semincontinuous metal film. The device comprises a medium 10' comprising a semicontinuous metal film of randomly distributed metal particles and their clusters, a light source 12', an additional layer 18' for structural support and other purposes, one or more near-field detectors 24' located on the same side of the medium as the light source, and a layer of photosensitive materials 66'. The device optionally comprises one or more near-field detectors 26' located on the opposite side of the medium from the light source.

EXAMPLE 13

Enhancement of Photochemistry and Photobiology

Semicontinuous metal films can also be used as media for enhancing photochemistry and photobiology. There are numerous chemical reactions and biological processes that are initiated or accelerated by light irradiation. N. J. Turro, *Modern Molecular Photochemistry* (Univ. Science Books, 1997); N. Serpone, et al., eds., *Photocatalysis: Fundamentals and Applications* (Wiley, N.Y. 1989); E. Kohen, *Photobiology* (Academic Press, 1995). A classical example of photobiology is light absorption by chlorophyll, the biomolecule that initiates the photosynthesis process. Light absorption by chlorophyll is inefficient; only a few photons are absorbed by a chlorophyll molecule in a leaf under normal conditions. By employing the enhancement provided by semicontinuous metal films and by microcavities coated with the films one can dramatically increase the efficiency of photosynthesis, as well other photobiological and photochemical processes. The intense local optical intensity in the hot spots promotes chemical reactions and biological processes, allowing single- and multi-photon reactions and processes to proceed at sufficient large rates even at relatively low incident light intensities.

Enhancement of photochemistry and photobiology can be even greater when a semicontinuous metal film is deposited on the internal surface of a highly porous dielectric matrix. An example of such matrix material is zeolites, which typically have pores of sizes from 10 to 100,000 nm, so that the effective internal surface can be as large as 10 $m^2$ for a zeolite of volume of 1 $cm^3$. The semicontinuous metal film can be deposited on the internal surface of a zeolite by various methods of chemical deposition, e.g., ion exchange method is used for this purpose. V. Petranovskii, et al., *Complex Mediums II: Beyond Linear Isotropic Dielectrics*, SPIE Proc. 4467, p. 377 (2001). Semicontinuous metal films on the internal surface of highly porous dielectric matrix enhance photochemistry and photobiology reactions of gaseous and liquid reagents located in the porous of the matrix.

Figure 26:
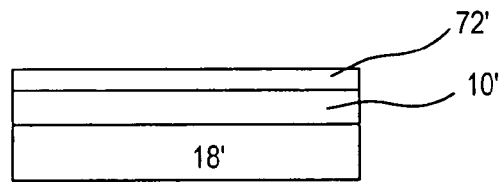
FIG. 26 is a schematic representation of a photochemical enhanced device employing a semicontinuous metal film.
Figure 27:
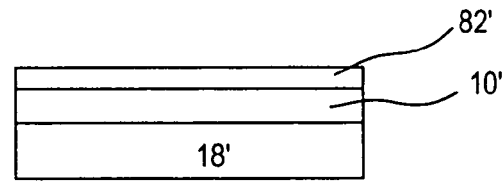
FIG. 27 is a schematic representation of a photobiological enhanced device employing a semicontinuous metal film.

FIGS. 26 and 27 illustrate photochemical and photobiological enhanced devices employing a semicontinuous film according to the invention, respectively. The devices preferably comprise a medium 10' comprising a semicontinuous metal film of randomly distributed metal particles and their clusters, an additional layer 18' for structural support and other purposes, and a photochemical agent 72' or a photobiological agent 82'.

EXAMPLE 14

Generation of Attosecond Pulses

Semicontinuous metal films or semicontinuous-metal-film/microcavity composites can be used for generation of ultra-short pulses with pulse duration shorter than a light cycle, including sub-femtosecond or attosecond pulses. This is possible because of the extremely broad spectrum of the normal modes (eigenmodes) in a semicontinuous metal film. These modes cover a spectral range from the near-ultraviolet to the mid-infrared. The sub-femtosecond pulses can be locally produced in the nanometer-sized hot spots, using excitation pulses that have a broad spectral range. The excitation pulses with the pulse duration in the range between 1 to 1000 femtoseconds can excite modes in a semicontinuous metal film over a broader spectral range. This can occur because the spectral wings of the excitation pulse can excite the modes with much larger enhancement so that the resultant spectrum of the radiating modes can be broader than the spectrum of the excitation pulse. As a result, the local field intensity in the hot spots can experience sub-femtosecond fluctuations. These fluctuations can be detected by using a near-field scanning optical method. Another possible means of the local excitation of sub-femtosecond pulses is to use the white light, which is a supercontinuum of incoherent modes in a very broad spectral range, including the visible and infrared parts of the spectrum. The white light can be generated in a large variety of materials by using femtosecond pulses. When irradiated with the white light, modes from a very broad spectral range are excited on a semicontinuous metal film. The mode self-phasing that can occur in this case results in attosecond fluctuations in the hot spots.

Figure 28:
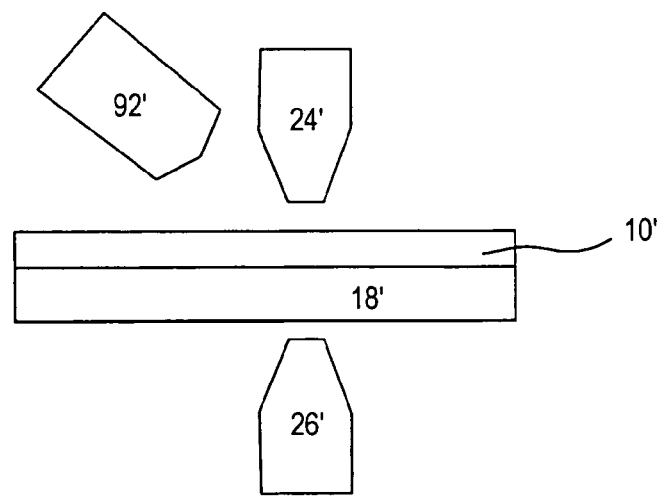
FIG. 28 is a schematic representation of a sub-femtosecond pulse generation device employing a semicontinuous metal film.

FIG. 28 illustrates a sub-femtosecond pulse generation device employing a semicontinuous metal film according to the invention. The device preferably comprises a medium 10' comprising a semicontinuous metal film of randomly distributed metal particles and their clusters, a light source 92' selected from the group of femtosecond pulses and white-light, an additional layer 18' for structural support and other purposes, and one or more near-field detectors 24' located on the same side of the medium as the light source. The device optionally comprises one or more near-field detectors 26' located on the opposite side of the medium from the light source.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A light emitting apparatus comprising:
   at least one light source;
   a fractal medium; and
   a microcavity, wherein said medium is located in the vicinity of said microcavity.

2. The light emitting apparatus of claim 1 wherein said medium comprises aggregated nanoparticles comprising fractals.

3. The light emitting apparatus of claim 1 wherein said medium comprises a semicontinuous metal film of randomly distributed metal particles and their clusters at approximately their percolation threshold.

4. The light emitting apparatus of claim 1 wherein said microcavity comprises a solid microcavity, and said medium is embedded within said solid microcavity.

5. The light emitting apparatus of claim 1 wherein said microcavity comprises a hollow microcavity, and said medium is located within said hollow microcavity.

6. The light emitting apparatus of claim 1 wherein said medium comprises individual nanoparticles each of an average diameter that is less than the optical wavelength of interest.

7. The light emitting apparatus of claim 1 wherein said microcavity comprises an exterior dimension that is at least twice that of the optical wavelength of interest.

8. The light emitting apparatus of claim 2 further comprising at least one molecule selected from the group consisting of optically active organic and inorganic molecules, adsorbed on a surface of said nanoparticles.

9. The light emitting apparatus of claim 8 wherein said at least one molecule comprises at least one molecule selected from the group consisting of laser dye and sodium citrate molecules.

10. The light emitting apparatus of claim 2 further comprising at least one molecule selected from the group consisting of optically active organic and inorganic molecules, located within the light wavelength of the surface of said nanoparticles.

11. The light emitting apparatus of claim 10 wherein said at least one molecule comprises at least one molecule selected from the group consisting of laser dye and sodium citrate molecules.

12. A method of enhancing the optical emission of a material comprising the steps of:
   providing a fractal medium;
   doping the medium with the material;
   locating the doped medium in the vicinity of a microcavity; and
   exciting the doped medium with at least one light source.

13. The method of claim 12 wherein the providing step comprises providing aggregated nanoparticles comprising fractals.

14. The method of claim 12 wherein the providing step comprises providing a semicontinuous metal film of randomly distributed metal particles and their clusters at approximately their percolation threshold.

15. The method of claim 12 wherein doping the medium with the material comprises doping with at least one material selected from the group consisting of a single molecule, a plurality of molecules, a nanocrystal, a solid matrix, DNA, DNA fragments, amino acids, antigen, antibodies, bacteria, bacterial spores, and viruses.

16. The method of claim 12 wherein the locating step comprises embedding the medium within a solid microcavity.

17. The method of claim 12 wherein the locating step comprises locating the medium within a hollow microcavity.

18. The method of claim 12 wherein the step of doping further comprises doping with at least one molecule selected from the group consisting of optically active organic and inorganic molecules located within the light wavelength of the surface of the medium.

19. The method of claim 18 wherein the at least one molecule comprises at least one molecule selected from the group consisting of laser dye and sodium citrate molecules.

20. An amplifying apparatus having a gain greater than 1.2, said apparatus comprising:
at least one light source;
a microcavity; and
a fractal medium, said medium located in the vicinity of said microcavity.

21. The amplifying apparatus of claim 20 wherein said medium comprises aggregated nanoparticles comprising fractals.

22. The amplifying apparatus of claim 20 wherein said medium comprises a semicontinuous metal film of randomly distributed metal particles and their clusters at approximately their percolation threshold.

23. A method of amplification comprising the steps of:
providing a fractal medium;
locating the medium in the vicinity of a microcavity to amplify optical emission; and
exciting the medium with at least one light source.

24. The method of claim 23 wherein the providing step comprises providing aggregated nanoparticles comprising fractals.

25. The method of claim 23 wherein the providing step comprises providing a semicontinuous metal film of randomly distributed metal particles and their clusters at approximately their percolation threshold.

26. A wavelength translation apparatus comprising:
at least one light source;
a fractal medium; and
a microcavity, wherein said medium is located in the vicinity of said microcavity.

27. The wavelength translation apparatus of claim 26 wherein said medium comprises aggregated nanoparticles comprising fractals.

28. The wavelength translation apparatus of claim 26 wherein said medium comprises a semicontinuous metal film of randomly distributed metal particles and their clusters at approximately their percolation threshold.

29. A method of wavelength translation comprising the steps of:
providing a fractal medium;
locating the medium in the vicinity of a microcavity; and
exciting the medium with at least one light source.

30. The method of claim 29 wherein the providing step comprises providing aggregated nanoparticles comprising fractals.

31. The method of claim 29 wherein the providing step comprises providing a semicontinuous metal film of randomly distributed metal particles and their clusters at approximately their percolation threshold.

32. The method of claim 29 wherein locating the medium in the vicinity of a microcavity further comprises amplifying optical emissions via at least one process selected from the group of processes consisting of stimulated emission of photons, stimulated Raman scattering, stimulated hyper-Raman scattering, stimulated Brouillon scattering, optical parametric amplification, multi-photon emission, four-wave mixing, and phase conjugation.

33. An optical parametric oscillator comprising:
at least one light source;
a cavity; and
a fractal medium, said medium located in the vicinity of said cavity.

34. The optical parametric oscillator of claim 33 wherein said medium comprises aggregated nanoparticles comprising fractals.

35. The optical parametric oscillator of claim 33 wherein said medium comprises a semicontinuous metal film of randomly distributed metal particles and their clusters at approximately their percolation threshold.

36. The optical parametric oscillator of claim 33 wherein said cavity comprises a microcavity.

37. A light detection and ranging system comprising:
a transmitter light source;
a receiver to receive light produced from the interaction of the transmitter light with constituents;
a fractal medium; and
a microcavity, wherein said medium is located in the vicinity of said microcavity to amplify the received light.

38. The light detection and ranging system of claim 37 wherein said medium comprises aggregated nanoparticles comprising fractals.

39. The light detection and ranging system of claim 37 wherein said medium comprises a semicontinuous metal film of randomly distributed metal particles and their clusters at approximately their percolation threshold.

40. A method of optical data storage comprising the steps of:
providing a fractal medium;
locating the medium in the vicinity of a microcavity;
irradiating the medium with polychromatic light; and
generating hot spots in the medium due to intensity differences of different wavelengths, and spectral hole burning the medium due to photomodification, thereby creating high density storage capabilities.

41. The method of claim 40 wherein the providing step comprises providing aggregated nanoparticles comprising fractals.

42. The method of claim 40 wherein the providing step comprises providing a semicontinuous metal film of randomly distributed metal particles and their clusters at approximately their percolation threshold.

43. A method of detecting a material, wherein the material is a material selected from the group consisting of chemical compounds and biological materials, using near-field optical spectroscopy, the method comprising the steps of:

providing a fractal medium;
locating the material within a distance shorter than the light wavelength from a near-field optical detector; and
recording spectroscopic data of the material.

44. The method of claim 43 wherein the providing step comprises providing aggregated nanoparticles comprising fractals.

45. The method of claim 43 wherein the providing step comprises providing a semicontinuous metal film of randomly distributed metal particles and their clusters at approximately their percolation threshold.

46. The method of claim 43 further comprising the step of locating the medium in the vicinity of a microcavity.

47. The method of claim 46 wherein the exciting step further comprises exciting the microcavity.

48. The method of claim 43 further comprising the step of adsorbing the material on the surface of the medium.

49. The method of claim 43 further comprising the step of depositing the medium onto the detector.

50. The method of claim 43 wherein the locating step comprises locating the material within a distance shorter than the light wavelength from the input end of an optical fiber.

51. The method of claim 50 wherein in the locating step the input end is tapered.

52. The method of claim 43 wherein the locating step comprises locating the material within a distance shorter than the light wavelength from a sharp tip of a vibrating metal wire.

53. The method of claim 43 wherein the exciting step comprises exciting both the material and the medium with a light source through an optical fiber.

54. The method of claim 53 wherein the exciting step comprises exciting both the material and the medium with a light source through an end of an optical fiber.

55. The method of claim 54 wherein in the exciting step the end of the optical fiber is tapered.

56. The method of claim 54 wherein the exciting step further comprises locating the end of the optical fiber within a distance shorter than the light wavelength from the material.

57. The method of claim 43 wherein recording spectroscopic data comprises recording at least one data selected from the group consisting of electronic, vibrational, and rotational spectroscopy data of the material.

58. The method of claim 43 further comprising the step of doping the medium with the material.

59. An optical sensing enhancing material comprising:
a fractal medium; and
a microcavity, wherein said medium is located in a vicinity of said microcavity.

60. The optical sensing enhancing material of claim 59 wherein said medium comprises a semicontinuous metal film of randomly distributed metal particles and their clusters at approximately their percolation threshold.

61. A method of making an optical sensing enhancing material, the method comprising the steps of:
providing a microcavity; and
locating a fractal medium in a vicinity of the microcavity.

62. The method of claim 61 wherein the locating step comprises locating a semicontinuous metal film of randomly distributed metal particles and their clusters at approximately their percolation threshold in a vicinity of the microcavity.

63. An optical sensor comprising:
a fractal medium;
a microcavity, wherein said medium is located in a vicinity of said microcavity;
a light source incident on said medium; and
a detector for detecting light reflected from said medium.

64. The optical sensor of claim 63 wherein said medium comprises a semicontinuous metal film of randomly distributed metal particles and their clusters at approximately their percolation threshold.

65. The optical sensor of claim 63 wherein at least one analyte is placed in direct contact with said medium.

66. The optical sensor of claim 63 wherein at least one analyte is remote from said medium.

67. The optical sensor of claim 63 wherein said light source comprises two counterpropogating light sources.

68. The optical sensor of claim 63 wherein said microcavity is selected from the group consisting of quartz tubes and quartz rods.

69. An optical sensing method comprising the steps of:
providing a doped fractal medium with a material;
locating the doped medium in the vicinity of a microcavity;
exciting the doped medium with a light source; and
detecting light reflected from said doped medium.

70. The method of claim 69 wherein in the providing step the medium comprises a semicontinuous metal film of randomly distributed metal particles and their clusters at approximately their percolation threshold.

71. The optical sensing method of claim 69 additionally comprising the step of placing at least one analyte in direct contact with the doped medium.

72. The optical sensing method of claim 69 additionally comprising the step of locating at least one analyte remotely from the medium.

73. The optical sensing method of claim 69 wherein in the exciting step the light source comprises two counterpropogating light sources.

74. The optical sensing method of claim 69 wherein in the locating step the microcavity is selected from the group consisting of quartz tubes and quartz rods.

75. A method of detecting a material, the method comprising the steps of:
exciting both the material and a fractal medium in a vicinity of a microcavity with at least one light source; and
detecting spectroscopic data of the material.

76. The method of claim 75 wherein in the exciting step the medium comprises a semicontinuous metal film of randomly distributed metal particles and their clusters at approximately their percolation threshold.

77. An optical enhancing material comprising a fractal medium and a microcavity, wherein the medium is located in the vicinity of the microcavity.

78. The optical enhancing material of claim 77 wherein said medium comprises aggregated nanoparticles comprising fractals.

79. The optical enhancing material of claim 77 wherein said medium comprises a semicontinuous metal film of randomly distributed metal particles and their clusters at approximately their percolation threshold.

80. The material of claim 79 wherein said metal comprises at least one metal selected from the group consisting of silver, gold, copper, platinum, nickel, and aluminum.

81. The material of claim 79 wherein said metal particles have an average width between approximately 1 and 1000 nanometers.

82. The material of claim 79 wherein said metal particles and their clusters have lengths varying from the widths of individual metal particles to a lateral size of the metal film.

83. The material of claim 79 wherein said semicontinuous metal film has an average thickness between approximately 1 and 100 nanometers.

84. The material of claim 79 wherein said semicontinuous metal film has a metal-filling factor p over a range between $p_c-(\epsilon_{dielectric}/|\epsilon_{metal}|)^{0.36}$ and $p_c+(\epsilon_{dielectric}/|\epsilon_{metal}|)^{0.36}$, where $p_c$ is a metal-filling factor at the percolation threshold, $\epsilon_{dielectric}$ is a dielectric function, permittivity, of a dielectric component of the semicontinuous metal film, and $\epsilon_{metal}$ is a dielectric function, permittivity, of a metal component of the semicontinuous metal film.

85. The material of claim 79 wherein said semicontinuous metal film is manufactured with at least one method selected from the group consisting of ion exchange, thermal evaporation, pulsed laser deposition, laser ablation, electron-beam deposition, ion-beam deposition, sputtering, radio-frequency glow discharge, and lithography.

86. The material of claim 77 wherein said material provides optical enhancement at light wavelengths between approximately 10 and 100,000 nanometers.

87. The material of claim 86 wherein said material provides optical enhancement at light wavelengths between approximately 200 and 20,000 nanometers.

88. The material of claim 77 additionally comprising an analyte placed proximate said medium.

89. The material of claim 88 wherein said analyte comprises at least one analyte selected from the group consisting atoms, molecules, nanocrystals, nanoparticles, and biological materials.

90. The material of claim 88 wherein said analyte is chiral.

91. The material of claim 88 additionally comprising a non-reactive surface coating placed over a component selected from the group consisting of said analyte, said medium, and both.

92. The material of claim 77 wherein said microcavity comprises one or more materials selected from the group consisting of dielectric and semiconductor materials.

93. The material of claim 77 wherein said microcavity is selected from the group consisting of spheres, deformed spheres, spheroids, rods, and tubes.

94. The material of claim 77 wherein said microcavity is a semiconductor laser cavity.

95. The material of claim 77 wherein said medium is located at one or more surfaces of said microcavity selected from the group consisting of inner and outer surfaces.

96. The material of claim 77 wherein said medium is an integrated component of said microcavity.

97. An optical sensor comprising:
a fractal medium;
a microcavity, wherein the medium is located in the vicinity of the microcavity;
a light source incident on said medium; and
one or more detectors of light emitted from said medium.

98. The optical sensor of claim 97 wherein said medium comprises aggregated nanoparticles comprising fractals.

99. The optical sensor of claim 97 wherein said medium comprises a semicontinuous metal film of randomly distributed metal particles and their clusters at approximately their percolation threshold.

100. The optical sensor of claim 97 wherein said detector detects at least one signal selected from the group consisting of fluorescence, spontaneous emission, Raman scattering, Rayleigh scattering, Brillouin scattering, and nonlinear optical processes selected from the group consisting of stimulated Raman scattering, hyper-Raman scattering, hyper-Rayleigh scattering, multi-photon anti-Stokes emission, harmonic generation, sum-frequency generation, difference-frequency generation, optical parametric processes, multi-photon absorption, three- and four-wave mixing, and phase conjugation.

101. An optical sensing method comprising the steps of:
providing a doped fractal medium;
locating the doped fractal medium proximate a medium;
employing a microcavity, wherein the doped fractal medium is located in the vicinity of the microactivity;
exciting the doped fractal medium with a light source; and
detecting light emitted from said doped fractal medium.

102. The method of claim 101 wherein in the providing step the fractal medium comprises aggregated nanoparticles comprising fractals.

103. The method of claim 101 wherein in the providing step the fractal medium comprises a semicontinuous metal film of randomly distributed metal particles and their clusters at approximately their percolation threshold.

104. The optical sensing method of claim 101 wherein said detecting step comprises detecting at least one signal selected from the group consisting of fluorescence, spontaneous emission, Raman scattering, Rayleigh scattering, Brillouin scattering, and nonlinear optical processes selected from the group consisting of stimulated Raman scattering, multi-photon anti-Stokes emission, hyper-Raman scattering, hyper-Rayleigh scattering, harmonic generation, sum-frequency generation, difference-frequency generation, optical parametric processes, multi-photon absorption, three- and four-wave mixing, and phase conjugation.

105. A method of detecting an analyte material, the method comprising the steps of:
employing a microcavity;
exciting both the analyte material and a fractal medium in a vicinity of the analyte material with at least one light source; and
detecting light emitted from the material and medium.

106. The method of claim 105 wherein in the exciting step the medium comprises aggregated nanoparticles comprising fractals.

107. The method of claim 105 wherein in the exciting step the medium comprises a semicontinuous metal film of randomly distributed metal particles and their clusters at approximately their percolation threshold.

108. The method of claim 105 wherein said detecting step comprises detecting at least one signal selected from the group consisting of fluorescence, spontaneous emission, Raman scattering, Rayleigh scattering, Brillouin scattering, and nonlinear optical processes selected from the group consisting of stimulated Raman scattering, multi-photon anti-Stokes emission, hyper-Raman scattering, hyper-Rayleigh scattering, harmonic generation, sum-frequency generation, difference-frequency generation, optical parametric processes, multi-photon absorption, three- and four-wave mixing, and phase conjugation.

109. The method of claim 105 wherein the analyte material is selected from the group consisting of atoms; molecules; nanoparticles; chemical agents in water and atmosphere; biological agents in water and atmosphere; contaminations and environment hazards in the air, in water, in soil, at or near manufacturing sites, or at waste dumps; explosives; controlled substances; residual chemicals in foods; food poison; and chemical and biological agents in a body, bodily fluids, and wastes of humans and animals.

110. The method of claim 109 additionally wherein said molecules comprise chiral molecules.

111. A gratingless spectrometer comprising:
a fractal medium;
a microcavity;
a light source incident on said medium; and
one or more near-field detectors for detecting light emitted from said medium;
wherein said medium is located in the vicinity of said microactivity.

112. The gratingless spectrometer of claim 111 wherein said medium comprises aggregated nanoparticles comprising fractals.

113. The gratingless spectrometer of claim 111 wherein said medium comprises a semicontinuous metal film of randomly distributed metal particles and their clusters at approximately their percolation threshold.

114. A gratingless spectroscopy method comprising the steps of:
providing a fractal medium;
locating the fractal medium in the vicinity of a microcavity;
exciting the medium with a light source; and
detecting light emitted from said doped medium in the near-field zone.

115. The method of claim 114 wherein in the providing step the medium comprises aggregated nanoparticles comprising fractals.

116. The method of claim 114 wherein in the providing step the medium comprises a semicontinuous metal film of randomly distributed metal particles and their clusters at approximately their percolation threshold.

117. A device for cryptography, coding and decoding information, said device comprising:
a fractal medium;
a light source incident on said medium;
one or more near-field detectors of light emitted from said medium; and
a logic component that compares a detected light pattern with an expected pattern.

118. The device of claim 117 wherein said medium comprises aggregated nanoparticles comprising fractals.

119. The device of claim 117 wherein said medium comprises a semicontinuous metal film of randomly distributed metal particles and their clusters at approximately their percolation threshold.

120. The device of claim 117 further comprising a microcavity.

121. A method for cryptography, coding and decoding information, the method comprising the steps of:
providing a fractal medium;
exciting the medium with a light source;
detecting light emitted from said medium in the near-field zone; and
comparing a detected light pattern with an expected pattern.

122. The method of claim 121 wherein in the providing step the medium comprises aggregated nanoparticles comprising fractals.

123. The method of claim 121 wherein in the providing step the medium comprises a semicontinuous metal film of randomly distributed metal particles and their clusters at approximately their percolation threshold.

124. The method of claim 121 further comprising the step of providing a microcavity.

125. An enhanced optical limiting material comprising:
a fractal medium;
a microcavity; and
an optical limiting material placed proximate the fractal medium;
wherein said medium is located in the vicinity of said microactivity.

126. The material of claim 125 wherein said medium comprises aggregated nanoparticles comprising fractals.

127. The material of claim 125 wherein said medium comprises a semicontinuous metal film of randomly distributed metal particles and their clusters at approximately their percolation threshold.

128. An enhanced optical limiting device comprising:
a fractal medium;
a microcavity; and
an optical limiting material placed proximate the medium;
wherein said medium is located in the said vicinity of said microcavity.

129. The device of claim 128 wherein said medium comprises aggregated nanoparticles comprising fractals.

130. The device of claim 128 wherein said medium comprises a semicontinuous metal film of randomly distributed metal particles and their clusters at approximately their percolation threshold.

131. A microlaser comprising:
a fractal medium;
an optically active material; and
an energy source applied to said medium and said optically active material; and
a microcavity;
wherein said medium is located on or within said microcavity.

132. The microlaser of claim 131 wherein said medium comprises aggregated nanoparticles comprising fractals.

133. The microlaser of claim 131 wherein said medium comprises a semicontinuous metal film of randomly distributed metal particles and their clusters at approximately their percolation threshold.

134. An optical amplifier comprising:
a fractal medium;
a microcavity, wherein the medium is located in the vicinity of the microcavity; and
a light source incident on said medium.

135. The optical amplifier of claim 134 wherein said medium comprises aggregated nanoparticles comprising fractals.

136. The optical amplifier of claim 134 wherein said medium comprises a semicontinuous metal film of randomly distributed metal particles and their clusters at approximately their percolation threshold.

137. The optical amplifier of claim 134 additionally comprising a layer of coating material selected from the group consisting of molecules, nanocrystals, and nanoparticles placed proximate said medium.

138. An optical amplification method comprising the steps of:
providing a fractal medium;
providing a microcavity; wherein the medium is located in the vicinity of the microcavity
providing an input signal; and
exciting the medium with a light source.

139. The method of claim 138 wherein the step of providing a fractal medium comprises providing aggregated nanoparticles comprising fractals.

140. The method of claim 138 wherein in the step of providing a fractal medium comprises providing a semicontinuous metal film of randomly distributed metal particles and their clusters at approximately their percolation threshold.

141. The optical amplification method of claim 40 additionally comprising the step of providing a layer of coating material selected from the group consisting of molecules, nanocrystals, and nanoparticles placed proximate the medium.

142. An optical switch comprising:
a fractal medium;
a microcavity; and
a light source incident on said medium;
wherein said medium is located in the vicinity of said microcavity.

143. The optical switch of claim 142 wherein said medium comprises aggregated nanoparticles comprising fractals.

144. The optical switch of claim 142 wherein said medium comprises a semicontinuous metal film of randomly distributed metal particles and their clusters at approximately their percolation threshold.

145. The optical switch of claim 142 additionally comprising a layer of optical switching material selected from the group consisting of molecules, nanocrystals, and nanoparticles placed proximate the medium.

146. An optical switching method comprising the steps of:
providing a fractal medium;
providing a microcavity, wherein the medium is located in the vicinity of the microcavity;
providing an input signal; and
exciting the medium with a light source.

147. The method of claim 146 wherein the step of providing a fractal medium comprises providing aggregated nanoparticles comprising fractals.

148. The method of claim 146 wherein in the step of providing a fractal medium comprises providing a semicontinuous metal film of randomly distributed metal particles and their clusters at approximately their percolation threshold.

149. The optical switching method of claim 146 additionally comprising the step of providing a layer of coating material selected from the group consisting molecules, nanocrystals, and nanoparticles placed proximate the medium.

150. A super density optical recording device comprising:
a fractal medium;
a layer of photosensitive materials placed proximate said medium;
a light source incident on said medium; and
one or more near-field detectors for detecting light emitted from said medium and said layer of photosensitive materials.

151. The device of claim 150 wherein said medium comprises aggregated nanoparticles comprising fractals.

152. The device of claim 150 wherein said medium comprises a semicontinuous metal film of randomly distributed metal particles and their clusters at approximately their percolation threshold.

153. The device of claim 150 further comprising a microcavity.

154. A super density optical recording method comprising the steps of:
providing a fractal medium;
providing a layer of photosensitive materials placed proximate the medium;
exciting the medium and photosensitive materials with a light source; and
detecting light emitted from said medium and photosensitive materials in a near-field zone.

155. The method of claim 154 wherein the step of providing a fractal medium comprises providing aggregated nanoparticles comprising fractals.

156. The method of claim 154 wherein in the step of providing a fractal medium comprises providing a semicontinuous metal film of randomly distributed metal particles and their clusters at approximately their percolation threshold.

157. The method of claim 154 further comprising the step of providing a microcavity.

158. A photochemical enhancing device comprising:
a fractal medium;
a microcavity; and
a photochemical agent placed proximate said medium;
wherein said medium is located in the vicinity of said microcavity.

159. The device of claim 158 wherein said medium comprises aggregated nanoparticles comprising fractals.

160. The device of claim 158 wherein said medium comprises a semicontinuous metal film of randomly distributed metal particles and their clusters at approximately their percolation threshold.

161. The device of claim 158 additionally comprising a highly porous dielectric matrix comprising a surface coated by said medium.

162. A photochemical enhancing method comprising the steps of:
providing a fractal medium;
locating the medium in the vicinity of a microcavity;
providing a photochemical agent placed proximate the medium; and
exciting the medium and photochemical agent with a light source.

163. The method of claim 162 wherein the step of providing a fractal medium comprises providing aggregated nanoparticles comprising fractals.

164. The method of claim 162 wherein in the step of providing a fractal medium comprises providing a semicontinuous metal film of randomly distributed metal particles and their clusters at approximately their percolation threshold.

165. The method of claim 162 additionally comprising the step of providing a highly porous dielectric matrix.

166. A photobiological enhancing device comprising:
a fractal medium;
a microcavity; and
a photobiological agent placed proximate said medium;
wherein said medium is located in the vicinity of said microcavity.

167. The device of claim 166 wherein said medium comprises aggregated nanoparticles comprising fractals.

168. The device of claim 166 wherein said medium comprises a semicontinuous metal film of randomly distributed metal particles and their clusters at approximately their percolation threshold.

169. The device of claim 166 additionally comprising a highly porous dielectric matrix comprising a surface coated by said medium.

170. A photobiological enhancing method comprising the steps of:
providing a fractal medium;
providing a microcavity, wherein the medium is located in the vicinity of the microcavity;
providing a photobiological agent placed proximate the medium; and exciting the medium and photobiological agent with a light source.

171. The method of claim 170 wherein the step of providing a fractal medium comprises providing aggregated nanoparticles comprising fractals.

172. The method of claim 170 wherein in the step of providing a fractal medium comprises providing a semicontinuous metal film of randomly distributed metal particles and their clusters at approximately their percolation threshold.

173. The method of claim 170 additionally comprising the step of providing a highly porous dielectric matrix.

174. A sub-femtosecond pulse generation device comprising:
- a fractal medium;
- a microcavity;
- a light source incident on said medium; and
- one or more near-field detectors for detecting light emitted from said medium;
- wherein said medium is located in the vicinity of said microcavity.

175. The device of claim 174 wherein said medium comprises aggregated nanoparticles comprising fractals.

176. The device of claim 174 wherein said medium comprises a semicontinuous metal film of randomly distributed metal particles and their clusters at approximately their percolation threshold.

177. The device of claim 174 wherein said light source is selected from the group of femtosecond pulses and white-light.

178. A method of generation of sub-femtosecond pulses comprising the steps of:
- providing a fractal medium;
- providing a microcavity, wherein the medium is located in the vicinity of the microcavity;
- exciting the medium with a light source; and
- detecting the sub-femtosecond pulses using one or more near-field detectors.

179. The method of claim 178 wherein the step of providing a fractal medium comprises providing aggregated nanoparticles comprising fractals.

180. The method of claim 178 wherein in the step of providing a fractal medium comprises providing a semicontinuous metal film of randomly distributed metal particles and their clusters at approximately their percolation threshold.

181. The method of claim 178 wherein in the exciting step the light source is selected from the group of femtosecond pulses and white-light.

* * * * *